(12) United States Patent
Melanson et al.

(10) Patent No.: US 12,144,508 B2
(45) Date of Patent: *Nov. 19, 2024

(54) DEVICES AND METHODS FOR EXCLUDING THE LEFT ATRIAL APPENDAGE

(71) Applicant: Conformal Medical, Inc., Merrimack, NH (US)

(72) Inventors: David A. Melanson, Hudson, NH (US); Andy H. Levine, Newton Highlands, MA (US); James H. Loper, Wales, MA (US); Michael T. Radford, Nashua, NH (US); Carol Devellian, Topsfield, MA (US); Aaron V. Kaplan, Norwich, VT (US); Ronald B. Lamport, Pelham, NH (US)

(73) Assignee: Conformal Medical, Inc., Merrimack, NH (US)

( * ) Notice: Subject to any disclaimer, the term of this patent is extended or adjusted under 35 U.S.C. 154(b) by 557 days.

This patent is subject to a terminal disclaimer.

(21) Appl. No.: 17/183,160

(22) Filed: Feb. 23, 2021

(65) Prior Publication Data

US 2021/0169500 A1 Jun. 10, 2021

Related U.S. Application Data

(63) Continuation-in-part of application No. 16/782,871, filed on Feb. 5, 2020.
(Continued)

(51) Int. Cl.
*A61B 17/12* (2006.01)
*A61B 17/00* (2006.01)

(52) U.S. Cl.
CPC .. *A61B 17/12181* (2013.01); *A61B 17/12122* (2013.01); *A61B 2017/00632* (2013.01); *A61B 2017/1205* (2013.01)

(58) Field of Classification Search
CPC ........ A61B 17/12181; A61B 17/12122; A61B 2017/00632; A61B 2017/1205
See application file for complete search history.

(56) References Cited

U.S. PATENT DOCUMENTS

| | | | |
|---|---|---|---|
| 3,063,453 | A | 11/1962 | Brecht |
| 3,712,305 | A | 1/1973 | Wennerblom et al. |

(Continued)

FOREIGN PATENT DOCUMENTS

| | | |
|---|---|---|
| CA | 1341519 | 2/2007 |
| CN | 102088927 | 6/2011 |

(Continued)

OTHER PUBLICATIONS

Supplementary Partial European Search Report for Application No. EP 19 79 6112 dated Feb. 21, 2022.
(Continued)

*Primary Examiner* — Sarah A Long
*Assistant Examiner* — Raihan R Khandker
(74) *Attorney, Agent, or Firm* — Knobbe, Martens, Olson & Bear, LLP

(57) ABSTRACT

Systems, devices and methods for occluding the left atrial appendage (LAA). The device excludes the LAA from blood flow. The implantable device is delivered via transcatheter delivery into the LAA and secured within the LAA. The implant comprises an expandable and compliant frame having anchors and an expandable and conformable tubular foam body. A delivery and tether retraction system includes a handle for controlling a pusher and tether. The pusher may be moved a distance away from the implant without changing the orientation of the implant, while the tether is still attached to the implant. A loader includes a conical portion with guides and a reservoir for submerging the foam implant prior to loading and delivery.

23 Claims, 41 Drawing Sheets

Related U.S. Application Data

(60) Provisional application No. 62/803,289, filed on Feb. 8, 2019.

(56) References Cited

U.S. PATENT DOCUMENTS

| | | | |
|---|---|---|---|
| 3,812,856 | A | 5/1974 | Duncan et al. |
| 3,978,855 | A | 9/1976 | McRae et al. |
| 4,061,145 | A | 12/1977 | DesMarais |
| 4,475,911 | A | 10/1984 | Gellert |
| 5,192,301 | A | 3/1993 | Kamiya et al. |
| 5,456,693 | A | 10/1995 | Conston et al. |
| 5,634,936 | A | 6/1997 | Linden et al. |
| 5,670,572 | A | 9/1997 | Ott et al. |
| 5,725,568 | A | 3/1998 | Hastings |
| 5,792,179 | A | 8/1998 | Sideris |
| 5,823,198 | A | 10/1998 | Jones et al. |
| 5,847,012 | A | 12/1998 | Shalaby et al. |
| 5,848,040 | A | 12/1998 | Tanaka |
| 5,861,003 | A | 1/1999 | Latson et al. |
| 5,865,791 | A | 2/1999 | Whayne et al. |
| 5,969,000 | A | 10/1999 | Yang et al. |
| 5,968,091 | A | 11/1999 | Pinchuk |
| 6,152,144 | A | 11/2000 | Lesh et al. |
| 6,162,168 | A | 12/2000 | Schweich et al. |
| 6,231,561 | B1 | 5/2001 | Frazier et al. |
| 6,290,674 | B1 | 9/2001 | Roue et al. |
| 6,398,758 | B1 | 6/2002 | Jacobsen et al. |
| 6,408,981 | B1 | 6/2002 | Smith et al. |
| 6,419,669 | B1 | 7/2002 | Frazier et al. |
| 6,423,252 | B1 | 7/2002 | Chun et al. |
| 6,436,088 | B2 | 8/2002 | Frazier et al. |
| 6,447,539 | B1 | 9/2002 | Nelson et al. |
| 6,458,100 | B2 | 10/2002 | Roue et al. |
| 6,551,303 | B1 | 4/2003 | VanTassel et al. |
| 6,623,450 | B1 | 9/2003 | Dutta |
| 6,641,557 | B1 | 11/2003 | Frazier et al. |
| 6,651,303 | B1 | 11/2003 | Toivanen et al. |
| 6,652,555 | B1 | 11/2003 | VanTassel et al. |
| 6,652,556 | B1 | 11/2003 | VanTassel et al. |
| 6,666,861 | B1 | 12/2003 | Grabek |
| 6,689,150 | B1 | 2/2004 | VanTassel et al. |
| 6,712,804 | B2 | 3/2004 | Roue et al. |
| 6,712,810 | B2 | 3/2004 | Harrington et al. |
| 6,723,108 | B1 | 4/2004 | Jones et al. |
| 6,730,108 | B2 | 5/2004 | Van Tassel et al. |
| 6,881,875 | B2 | 4/2005 | Swenson |
| 6,941,169 | B2 | 9/2005 | Pappu |
| 6,949,113 | B2 | 9/2005 | Van Tassel et al. |
| 6,977,323 | B1 | 12/2005 | Swenson |
| 6,979,344 | B2 | 12/2005 | Jones et al. |
| 6,994,092 | B2 | 2/2006 | Van Der et al. |
| 7,011,671 | B2 | 3/2006 | Welch |
| 7,044,134 | B2 | 5/2006 | Khairkhahan et al. |
| 7,056,294 | B2 | 6/2006 | Khairkhahan et al. |
| 7,115,110 | B2 | 10/2006 | Frazier et al. |
| 7,128,073 | B1 | 10/2006 | Van der Burg et al. |
| 7,152,605 | B2 | 12/2006 | Khairkhahan et al. |
| 7,169,164 | B2 | 1/2007 | Borillo et al. |
| 7,192,439 | B2 | 3/2007 | Khairkhahan et al. |
| 7,226,458 | B2 | 6/2007 | Kaplan et al. |
| 7,291,382 | B2 | 11/2007 | Krueger et al. |
| 7,293,562 | B2 | 11/2007 | Malecki |
| 7,318,829 | B2 | 1/2008 | Kaplan et al. |
| 7,344,543 | B2 | 3/2008 | Sra |
| 7,358,282 | B2 | 4/2008 | Krueger et al. |
| 7,427,279 | B2 | 9/2008 | Frazier et al. |
| 7,549,983 | B2 | 6/2009 | Roue et al. |
| 7,566,336 | B2 | 7/2009 | Corcoran et al. |
| 7,597,704 | B2 | 10/2009 | Frazier et al. |
| 7,695,425 | B2 | 4/2010 | Schweich et al. |
| 7,713,282 | B2 | 5/2010 | Frazier et al. |
| 7,722,641 | B2 | 5/2010 | Van Der et al. |
| 7,727,189 | B2 | 6/2010 | VanTassel et al. |
| 7,735,493 | B2 | 6/2010 | van der Burg et al. |
| 7,747,047 | B2 | 6/2010 | Okerlund et al. |
| 7,780,683 | B2 | 8/2010 | Roue et al. |
| 7,803,395 | B2 | 9/2010 | Datta et al. |
| 7,824,397 | B2 | 11/2010 | Mcauley |
| 7,922,716 | B2 | 4/2011 | Malecki et al. |
| 7,972,359 | B2 | 7/2011 | Kreidler |
| 7,998,138 | B2 | 8/2011 | Mcauley |
| 8,043,329 | B2 | 10/2011 | Khairkhahan et al. |
| 8,052,715 | B2 | 11/2011 | Quinn et al. |
| 8,057,530 | B2 | 11/2011 | Kusleika et al. |
| 8,080,032 | B2 | 12/2011 | van der Burg et al. |
| 8,083,768 | B2 | 12/2011 | Ginn et al. |
| 8,097,015 | B2 | 1/2012 | Devellian |
| 8,142,470 | B2 | 3/2012 | Quinn et al. |
| 8,157,818 | B2 | 4/2012 | Gartner et al. |
| 8,197,496 | B2 | 6/2012 | Roue et al. |
| 8,197,527 | B2 | 6/2012 | Borillo et al. |
| 8,221,445 | B2 | 7/2012 | Van Tassel et al. |
| 8,262,694 | B2 | 9/2012 | Widomski et al. |
| 8,287,563 | B2 | 10/2012 | Khairkhahan et al. |
| 8,313,504 | B2 | 11/2012 | Do et al. |
| 8,323,309 | B2 | 12/2012 | Khairkhahan et al. |
| 8,337,487 | B2 | 12/2012 | Datta et al. |
| 8,361,111 | B2 | 1/2013 | Widomski et al. |
| 8,460,282 | B2 | 6/2013 | Mcauley |
| 8,480,708 | B2 | 7/2013 | Kassab et al. |
| 8,523,897 | B2 | 9/2013 | Van Der et al. |
| 8,535,343 | B2 | 9/2013 | Van Der et al. |
| 8,540,760 | B2 | 9/2013 | Paul, Jr. et al. |
| 8,603,108 | B2 | 12/2013 | Roue et al. |
| 8,636,764 | B2 | 1/2014 | Miles et al. |
| 8,690,911 | B2 | 1/2014 | Miles et al. |
| 8,647,361 | B2 | 2/2014 | Borillo et al. |
| 8,647,367 | B2 | 2/2014 | Kassab et al. |
| 8,663,268 | B2 | 3/2014 | Quinn et al. |
| 8,663,273 | B2 | 3/2014 | Khairkhahan et al. |
| 8,685,055 | B2 | 4/2014 | VanTassel et al. |
| 8,715,302 | B2 | 5/2014 | Ibrahim et al. |
| 8,715,318 | B2 | 5/2014 | Miles |
| 8,740,934 | B2 | 7/2014 | McGuckin, Jr. |
| 8,764,793 | B2 | 7/2014 | Lee |
| 8,784,469 | B2 | 7/2014 | Kassab |
| 8,795,328 | B2 | 8/2014 | Miles et al. |
| 8,801,746 | B1 | 8/2014 | Kreidler et al. |
| 8,828,051 | B2 | 9/2014 | Javois et al. |
| 8,834,519 | B2 | 9/2014 | van der Burg et al. |
| 8,840,641 | B2 | 9/2014 | Miles et al. |
| 8,845,711 | B2 | 9/2014 | Miles et al. |
| 9,011,551 | B2 | 4/2015 | Oral et al. |
| 9,034,006 | B2 | 5/2015 | Quinn et al. |
| 9,089,313 | B2 | 7/2015 | Roue et al. |
| 9,131,849 | B2 | 9/2015 | Khairkhahan et al. |
| 9,132,000 | B2 | 9/2015 | VanTassel et al. |
| 9,161,830 | B2 | 10/2015 | Borillo et al. |
| 9,168,043 | B2 | 10/2015 | Van Der et al. |
| 9,186,152 | B2 | 11/2015 | Campbell et al. |
| 9,351,716 | B2 | 5/2016 | Miles et al. |
| 9,421,004 | B2 | 8/2016 | Roue et al. |
| 9,445,895 | B2 | 9/2016 | Kreidler |
| 9,474,516 | B2 | 10/2016 | Clark et al. |
| 9,554,804 | B2 | 1/2017 | Erzberger et al. |
| 9,592,058 | B2 | 3/2017 | Erzberger et al. |
| 9,592,110 | B1 | 3/2017 | Dan et al. |
| 9,649,115 | B2 | 5/2017 | Edmiston et al. |
| 9,693,780 | B2 | 7/2017 | Miles et al. |
| 9,693,781 | B2 | 7/2017 | Miles et al. |
| 9,700,323 | B2 | 7/2017 | Clark |
| 9,730,701 | B2 | 8/2017 | Tischler et al. |
| 9,743,932 | B2 | 8/2017 | Amplatz et al. |
| 9,763,666 | B2 | 9/2017 | Wu et al. |
| 9,808,253 | B2 | 11/2017 | Li et al. |
| 9,839,431 | B2 | 12/2017 | Meyer et al. |
| 9,849,011 | B2 | 12/2017 | Zimmerman et al. |
| 9,861,370 | B2 | 1/2018 | Clark et al. |
| 9,883,864 | B2 | 2/2018 | Miles et al. |
| 9,883,936 | B2 | 2/2018 | Sutton et al. |
| 9,913,652 | B2 | 3/2018 | Bridgeman et al. |
| 9,943,299 | B2 | 4/2018 | Khairkhahan et al. |
| 9,943,315 | B2 | 4/2018 | Kaplan et al. |
| 10,143,456 | B2 | 12/2018 | Javois |

(56) References Cited

U.S. PATENT DOCUMENTS

| | | |
|---|---|---|
| 10,617,425 B2 | 4/2020 | Kaplan et al. |
| 10,722,240 B1 | 7/2020 | Melanson et al. |
| 11,026,695 B2 | 6/2021 | Melanson |
| 11,109,868 B2 | 9/2021 | Forbes |
| 11,116,510 B2 | 9/2021 | Melanson |
| 11,123,079 B2 | 9/2021 | Andserson |
| 11,123,080 B2 | 9/2021 | Lashinski |
| 11,134,934 B2 | 10/2021 | Rafiee |
| 11,154,303 B2 | 10/2021 | Miles |
| 11,166,703 B2 | 11/2021 | Kassab |
| 11,191,546 B2 | 12/2021 | Gong |
| 11,191,547 B2 | 12/2021 | Deville |
| 11,207,073 B2 | 12/2021 | Clark |
| 11,213,282 B2 | 1/2022 | Maslanka |
| 11,219,462 B2 | 1/2022 | Lashinski |
| 11,224,435 B2 | 1/2022 | Fung |
| 11,241,237 B2 | 2/2022 | Tischler |
| 11,241,239 B2 | 2/2022 | Cao |
| 11,253,241 B2 | 2/2022 | Li |
| 11,253,262 B2 | 2/2022 | Miles |
| 11,266,389 B2 | 3/2022 | Sternik |
| 11,284,871 B2 | 3/2022 | Corcoran |
| 11,284,899 B2 | 3/2022 | Ibrahim |
| 11,291,454 B2 | 4/2022 | Chen |
| 11,317,920 B2 | 5/2022 | Amplatz |
| 11,324,510 B2 | 5/2022 | Morejohn |
| 11,331,104 B2 | 5/2022 | Inouye |
| 11,337,684 B2 | 5/2022 | Zhang |
| 11,344,312 B2 | 5/2022 | Wang |
| 11,344,313 B2 | 5/2022 | Otero |
| 11,344,733 B2 | 5/2022 | Kaiser |
| 11,350,944 B2 | 6/2022 | Liddicoat |
| 11,357,512 B2 | 6/2022 | Fishel |
| 11,369,355 B2 | 6/2022 | Lee |
| 11,369,374 B2 | 6/2022 | Wheeler |
| 11,369,780 B2 | 6/2022 | Rabito |
| 11,389,167 B2 | 7/2022 | Clark |
| 11,399,842 B2 | 8/2022 | Kaplan |
| 11,399,843 B2 | 8/2022 | Lashinski |
| 11,413,047 B2 | 8/2022 | Clark |
| 11,413,048 B2 | 8/2022 | Anderson |
| 11,419,591 B2 | 8/2022 | Liu |
| 11,419,611 B2 | 8/2022 | Sharma |
| 11,426,172 B2 | 8/2022 | Melanson |
| 11,432,809 B2 | 9/2022 | Inouye et al. |
| 11,432,875 B2 | 9/2022 | Camus |
| 11,484,320 B2 | 11/2022 | Kangas |
| 11,484,397 B2 | 11/2022 | Dan et al. |
| 11,497,505 B2 | 11/2022 | Slaughter et al. |
| 11,497,636 B2 | 11/2022 | Xiao et al. |
| 11,512,416 B2 | 11/2022 | Koppe |
| 11,534,174 B2 | 12/2022 | Amplatz et al. |
| 11,534,175 B2 | 12/2022 | Hill |
| 11,534,320 B2 | 12/2022 | Westhoff et al. |
| 11,540,836 B2 | 1/2023 | Wang et al. |
| 11,540,837 B2 | 1/2023 | Edminston et al. |
| 11,540,838 B2 | 1/2023 | Groff et al. |
| 11,547,416 B2 | 1/2023 | Berger et al. |
| 11,547,417 B2 | 1/2023 | Li et al. |
| 11,690,630 B2 | 7/2023 | Centola |
| 11,690,633 B2 | 7/2023 | Min et al. |
| 11,712,249 B2 | 8/2023 | Bales et al. |
| 11,717,303 B2 | 8/2023 | Kaplan et al. |
| 11,737,761 B2 | 8/2023 | Otero et al. |
| 11,779,319 B2 | 10/2023 | Ma |
| 11,786,256 B2 | 10/2023 | Melanson et al. |
| 11,793,524 B2 | 10/2023 | Deville et al. |
| 11,806,019 B2 | 11/2023 | Li et al. |
| 11,806,063 B2 | 11/2023 | Coulombe |
| 11,812,968 B2 | 11/2023 | Li et al. |
| 11,812,969 B2 | 11/2023 | Lee et al. |
| 11,826,050 B2 | 11/2023 | Miller et al. |
| 11,832,828 B2 | 12/2023 | Krivoruchko et al. |
| 11,839,379 B2 | 12/2023 | Amplatz et al. |
| 11,840,779 B2 | 12/2023 | Köppe |
| 11,844,526 B2 | 12/2023 | Fung et al. |
| 11,844,566 B2 | 12/2023 | Fung et al. |
| 2002/0022860 A1 | 2/2002 | Borillo et al. |
| 2002/0049457 A1 | 4/2002 | Kaplan et al. |
| 2002/0072550 A1 | 6/2002 | Brady et al. |
| 2002/0095205 A1 | 7/2002 | Edwin et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111647 A1 | 8/2002 | Khairkhahan et al. |
| 2002/0169377 A1 | 11/2002 | Khairkhahan et al. |
| 2003/0023266 A1 | 1/2003 | Borillo et al. |
| 2003/0045893 A1 | 3/2003 | Ginn |
| 2003/0051735 A1 | 3/2003 | Pavcnik |
| 2003/0120337 A1 | 6/2003 | Van Tassel et al. |
| 2003/0191526 A1 | 10/2003 | Van Tassel et al. |
| 2003/0199923 A1 | 10/2003 | Khairkhahan et al. |
| 2003/0204203 A1 | 10/2003 | Khairkhahan et al. |
| 2003/0220667 A1 | 11/2003 | van der Burg et al. |
| 2004/0044361 A1 | 3/2004 | Frazier et al. |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0215230 A1 | 10/2004 | Frazier et al. |
| 2004/0220610 A1 | 11/2004 | Kreidler et al. |
| 2004/0225212 A1 | 11/2004 | Okerlund et al. |
| 2004/0230222 A1 | 11/2004 | van der Burg et al. |
| 2005/0004652 A1 | 1/2005 | van der Burg et al. |
| 2005/0033287 A1 | 2/2005 | Sra |
| 2005/0038470 A1 | 2/2005 | van der Burg et al. |
| 2005/0049573 A1 | 3/2005 | VanTassel et al. |
| 2005/0070952 A1 | 3/2005 | Devellian |
| 2005/0090857 A1 | 4/2005 | Kusleika et al. |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0177182 A1 | 8/2005 | van der Burg et al. |
| 2005/0203568 A1 | 9/2005 | van der Burg et al. |
| 2005/0228434 A1 | 10/2005 | Amplatz et al. |
| 2005/0234540 A1 | 10/2005 | Peavey et al. |
| 2005/0234543 A1 | 10/2005 | Glaser et al. |
| 2005/0267528 A1 | 12/2005 | Ginn |
| 2006/0009715 A1 | 1/2006 | Khairkhahan et al. |
| 2006/0116709 A1 | 6/2006 | Sepetka |
| 2007/0005147 A1 | 1/2007 | Levine |
| 2007/0083230 A1 | 4/2007 | Javois |
| 2007/0129753 A1 | 6/2007 | Quinn et al. |
| 2007/0135826 A1 | 6/2007 | Zaver et al. |
| 2007/0149988 A1 | 6/2007 | Michler et al. |
| 2007/0149995 A1 | 6/2007 | Quinn et al. |
| 2007/0162048 A1 | 7/2007 | Quinn et al. |
| 2007/0179345 A1 | 8/2007 | Santilli |
| 2007/0270891 A1 | 11/2007 | McGuckin, Jr. |
| 2007/0029393 A1 | 12/2007 | Grewem |
| 2007/0293934 A1 | 12/2007 | Grewe |
| 2008/0033241 A1 | 2/2008 | Peh et al. |
| 2008/0125795 A1 | 5/2008 | Kaplan et al. |
| 2008/0243183 A1 | 10/2008 | Miller et al. |
| 2008/0294175 A1 | 11/2008 | Bardsley et al. |
| 2008/0312664 A1 | 12/2008 | Bardsley et al. |
| 2009/0005760 A1 | 1/2009 | Cartledge |
| 2009/0088836 A1 | 4/2009 | Bishop et al. |
| 2009/0099596 A1 | 4/2009 | McGunkin, Jr. et al. |
| 2009/0112249 A1 | 4/2009 | Miles et al. |
| 2009/0143791 A1 | 6/2009 | Miller et al. |
| 2009/0157118 A1 | 6/2009 | Miller et al. |
| 2009/0264920 A1 | 10/2009 | Berenstein |
| 2009/0287145 A1 | 11/2009 | Cragg et al. |
| 2009/0306685 A1 | 12/2009 | Fill |
| 2009/0326577 A1 | 12/2009 | Johnson et al. |
| 2010/0057192 A1 | 3/2010 | Celermajer |
| 2010/0076463 A1 | 3/2010 | Mavani et al. |
| 2010/0191279 A1 | 7/2010 | Kassab et al. |
| 2010/0228184 A1 | 9/2010 | Mavani et al. |
| 2010/0228279 A1 | 9/2010 | Miles et al. |
| 2010/0228285 A1 | 9/2010 | Miles et al. |
| 2010/0286718 A1 | 11/2010 | Kassab et al. |
| 2010/0324585 A1 | 12/2010 | Miles et al. |

(56) References Cited

U.S. PATENT DOCUMENTS

| | | |
|---|---|---|
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0009853 A1 | 1/2011 | Bertolero et al. |
| 2011/0022079 A1 | 1/2011 | Miles et al. |
| 2011/0022168 A1 | 1/2011 | Cartledge |
| 2011/0054515 A1 | 3/2011 | Bridgeman et al. |
| 2011/0082495 A1 | 4/2011 | Ruiz |
| 2011/0087271 A1 | 4/2011 | Sargent et al. |
| 2011/0178539 A1 | 7/2011 | Holmes, Jr. et al. |
| 2011/0208233 A1 | 8/2011 | McGunkin, Jr. et al. |
| 2011/0218389 A1 | 9/2011 | Gobel |
| 2011/0218566 A1 | 9/2011 | van der Burg et al. |
| 2011/0220120 A1 | 9/2011 | Frigstad et al. |
| 2011/0257674 A1 | 10/2011 | Evert et al. |
| 2011/0264119 A1 | 10/2011 | Bayon et al. |
| 2011/0307003 A1 | 12/2011 | Chambers |
| 2011/0313507 A1 | 12/2011 | Miranda et al. |
| 2012/0010644 A1 | 1/2012 | Sideris et al. |
| 2012/0029553 A1 | 2/2012 | Quinn et al. |
| 2012/0065662 A1 | 3/2012 | van der Burg et al. |
| 2012/0065667 A1 | 3/2012 | Javois et al. |
| 2012/0157916 A1 | 6/2012 | Quinn et al. |
| 2012/0158022 A1 | 6/2012 | Kaplan et al. |
| 2012/0172927 A1 | 7/2012 | Campbell et al. |
| 2012/0221042 A1 | 8/2012 | Schwartz et al. |
| 2012/0239077 A1 | 9/2012 | Zaver et al. |
| 2012/0283585 A1 | 11/2012 | Werneth et al. |
| 2012/0283773 A1 | 11/2012 | VanTassel et al. |
| 2012/0316584 A1 | 12/2012 | Miles et al. |
| 2012/0323262 A1 | 12/2012 | Ibrahim et al. |
| 2012/0323267 A1 | 12/2012 | Ren |
| 2012/0323270 A1 | 12/2012 | Lee |
| 2012/0330342 A1 | 12/2012 | Jones |
| 2013/0006343 A1 | 1/2013 | Kassab |
| 2013/0012982 A1 | 1/2013 | Khairkhahan et al. |
| 2013/0018413 A1 | 1/2013 | Oral et al. |
| 2013/0018414 A1 | 1/2013 | Widomski et al. |
| 2013/0083983 A1 | 4/2013 | Zhong et al. |
| 2013/0110154 A1 | 5/2013 | van der Burg et al. |
| 2013/0116724 A1 | 5/2013 | Clark et al. |
| 2013/0138138 A1 | 5/2013 | Clark et al. |
| 2013/0165965 A1 | 6/2013 | Carlson et al. |
| 2013/0178889 A1 | 7/2013 | Miles et al. |
| 2013/0237908 A1 | 9/2013 | Clark |
| 2014/0005714 A1 | 1/2014 | Quick et al. |
| 2014/0046360 A1 | 2/2014 | van der Burg et al. |
| 2014/0074151 A1* | 3/2014 | Tischler ........... A61B 17/12122 606/200 |
| 2014/0128903 A1 | 5/2014 | Alferness |
| 2014/0135817 A1 | 5/2014 | Tischler et al. |
| 2014/0257320 A1 | 9/2014 | Fitz |
| 2014/0277074 A1 | 9/2014 | Kaplan et al. |
| 2014/0330368 A1 | 11/2014 | Gloss |
| 2014/0336699 A1 | 11/2014 | van der Burg et al. |
| 2014/0364941 A1 | 12/2014 | Edmiston et al. |
| 2014/0371789 A1 | 12/2014 | Hariton et al. |
| 2015/0005810 A1 | 1/2015 | Center et al. |
| 2015/0039021 A1 | 2/2015 | Khairkhahan et al. |
| 2015/0133989 A1 | 5/2015 | Lubock et al. |
| 2015/0196305 A1 | 7/2015 | Meyer et al. |
| 2016/0058539 A1 | 1/2016 | Vantassel et al. |
| 2016/0089151 A1 | 3/2016 | Siegel et al. |
| 2016/0106437 A1 | 4/2016 | van der Burg et al. |
| 2016/0278784 A1 | 9/2016 | Edmiston |
| 2017/0042549 A1* | 2/2017 | Kaplan ........... A61B 17/12145 |
| 2017/0042550 A1 | 2/2017 | Chakraborty et al. |
| 2017/0095238 A1 | 4/2017 | Rudman et al. |
| 2017/0095256 A1 | 4/2017 | Lindgren et al. |
| 2017/0100112 A1 | 4/2017 | Van Der et al. |
| 2017/0135801 A1 | 5/2017 | Delaney, Jr. et al. |
| 2017/0224354 A1 | 8/2017 | Tischler et al. |
| 2017/0281192 A1 | 10/2017 | Tieu et al. |
| 2017/0290594 A1 | 10/2017 | Chakraborty et al. |
| 2017/0340336 A1 | 11/2017 | Osypka |
| 2018/0000490 A1 | 1/2018 | Kaplan et al. |
| 2018/0116678 A1 | 5/2018 | Melanson |
| 2018/0185130 A1 | 7/2018 | Janardhan et al. |
| 2018/0206830 A1 | 7/2018 | Khairkhahan et al. |
| 2018/0250014 A1 | 9/2018 | Melanson et al. |
| 2018/0338824 A1 | 11/2018 | VanTassel et al. |
| 2019/0083075 A1 | 3/2019 | Onushko et al. |
| 2019/0125362 A1 | 5/2019 | Tischler |
| 2019/0336137 A1 | 11/2019 | Chakraborty et al. |
| 2020/0253614 A1 | 8/2020 | Melanson |
| 2020/0269059 A1 | 8/2020 | Kaiser |
| 2021/0275183 A1 | 9/2021 | Amplatz |
| 2021/0282757 A1 | 9/2021 | Manash |
| 2021/0298728 A1 | 9/2021 | Lashinski |
| 2021/0298763 A1 | 9/2021 | Stahmann |
| 2021/0298764 A1 | 9/2021 | Subramaniam |
| 2021/0330333 A1 | 10/2021 | Gray |
| 2021/0346033 A1 | 11/2021 | Horton |
| 2021/0346706 A1 | 11/2021 | Devich |
| 2021/0353354 A1 | 11/2021 | Schuler |
| 2021/0369283 A1 | 12/2021 | O'Halloran |
| 2021/0369284 A1 | 12/2021 | Lashinski |
| 2021/0378679 A1 | 12/2021 | Amplatz |
| 2021/0393271 A1 | 12/2021 | Melanson |
| 2021/0401418 A1 | 12/2021 | Dang |
| 2022/0000488 A1 | 1/2022 | Anderson |
| 2022/0022854 A1 | 1/2022 | Lashinski |
| 2022/0022880 A1 | 1/2022 | Dosta |
| 2022/0031333 A1 | 2/2022 | Zhou |
| 2022/0054117 A1 | 2/2022 | Rafiee |
| 2022/0061829 A1 | 3/2022 | Kassab |
| 2022/0079600 A1 | 3/2022 | Moriyama |
| 2022/0079667 A1 | 3/2022 | Gabay |
| 2022/0087664 A1 | 3/2022 | Maslanka |
| 2022/0087683 A1 | 3/2022 | Fishel |
| 2022/0087684 A1 | 3/2022 | Edminston |
| 2022/0087741 A1 | 3/2022 | Lashinski |
| 2022/0088355 A1 | 3/2022 | Rabito |
| 2022/0096093 A1 | 3/2022 | Centola |
| 2022/0104830 A1 | 4/2022 | Centola |
| 2022/0117555 A1 | 4/2022 | Zarbatany |
| 2022/0117608 A1 | 4/2022 | Tischler |
| 2022/0117764 A1 | 4/2022 | Jiang |
| 2022/0133178 A1 | 5/2022 | Li |
| 2022/0133261 A1 | 5/2022 | Urman |
| 2022/0167989 A1 | 6/2022 | Ibrahim |
| 2022/0175390 A1 | 6/2022 | Lee |
| 2022/0175391 A1 | 6/2022 | Zhou |
| 2022/0192676 A9 | 6/2022 | Kaplan |
| 2022/0202401 A1 | 6/2022 | Isilki |
| 2022/0211386 A1 | 7/2022 | Amplatz |
| 2022/0218355 A1 | 7/2022 | Wedul |
| 2022/0240941 A1 | 8/2022 | Lashinski |
| 2022/0249101 A1 | 8/2022 | Min |
| 2022/0257259 A1 | 8/2022 | Li |
| 2022/0257955 A1 | 8/2022 | Zarbatany |
| 2022/0265280 A1 | 8/2022 | Chamorro |
| 2022/0280144 A1 | 9/2022 | Lee |
| 2022/0287697 A1 | 9/2022 | Roche |
| 2022/0287713 A1 | 9/2022 | Wheeler |
| 2022/0287720 A1 | 9/2022 | Otero |
| 2022/0296306 A1 | 9/2022 | Camus |
| 2022/0313270 A1 | 10/2022 | Inouye et al. |
| 2022/0330948 A1 | 10/2022 | Lee et al. |
| 2022/0331104 A1 | 10/2022 | Rafiee |
| 2022/0331566 A1 | 10/2022 | Rabito et al. |
| 2022/0338877 A1 | 10/2022 | Natesan et al. |
| 2022/0346796 A1 | 11/2022 | Morejohn et al. |
| 2022/0354472 A1 | 11/2022 | Berger et al. |
| 2022/0354501 A1 | 11/2022 | Clark et al. |
| 2022/0361864 A1 | 11/2022 | Liu et al. |
| 2022/0370079 A1 | 11/2022 | Harari et al. |
| 2022/0387043 A1 | 12/2022 | Centola |
| 2022/0387757 A1 | 12/2022 | Wang et al. |
| 2022/0395279 A1 | 12/2022 | Chen et al. |
| 2022/0401109 A1 | 12/2022 | Zarbatany et al. |
| 2022/0401110 A1 | 12/2022 | Dinges et al. |
| 2022/0401112 A1 | 12/2022 | Zhou et al. |
| 2022/0409211 A1 | 12/2022 | Moszner |

(56) References Cited

U.S. PATENT DOCUMENTS

| | | |
|---|---|---|
| 2022/0409255 A1 | 12/2022 | Li et al. |
| 2023/0008857 A1 | 1/2023 | Tu et al. |
| 2023/0010024 A1 | 1/2023 | Chen et al. |
| 2023/0012824 A1 | 1/2023 | O'Halloran et al. |
| 2023/0018512 A1 | 1/2023 | O'Halloran et al. |
| 2023/0032647 A1 | 2/2023 | Kaplan et al. |
| 2023/0071677 A1 | 3/2023 | Melanson et al. |
| 2023/0129101 A1 | 4/2023 | Rabito et al. |
| 2023/0130379 A1 | 4/2023 | Akpinar et al. |
| 2023/0145262 A1 | 5/2023 | Inouye et al. |
| 2023/0149072 A1 | 5/2023 | O'Halloran et al. |
| 2023/0172611 A1 | 6/2023 | Biscarrat et al. |
| 2023/0172625 A1 | 6/2023 | Zickert et al. |
| 2023/0190293 A1 | 6/2023 | Berger et al. |
| 2023/0210537 A1 | 7/2023 | Li et al. |
| 2023/0218303 A1 | 7/2023 | Lee |
| 2023/0248983 A1 | 8/2023 | Zarbatany et al. |
| 2023/0263531 A1 | 8/2023 | Lashinski et al. |
| 2023/0270442 A1 | 8/2023 | Peelukhana et al. |
| 2023/0270500 A1 | 8/2023 | Weber et al. |
| 2023/0285029 A1 | 9/2023 | Yang et al. |
| 2023/0310018 A1 | 10/2023 | Lashinski et al. |
| 2023/0320713 A1 | 10/2023 | Li et al. |
| 2023/0329722 A1 | 10/2023 | Buchbinder et al. |
| 2023/0346360 A1 | 11/2023 | Ditter et al. |
| 2023/0355302 A1 | 11/2023 | Achterhoff et al. |
| 2023/0389931 A1 | 12/2023 | Li et al. |
| 2023/0389932 A1 | 12/2023 | Ozenne et al. |
| 2023/0397912 A1 | 12/2023 | Tillman et al. |
| 2023/0404658 A1 | 12/2023 | O'Halloran et al. |
| 2024/0074766 A1 | 3/2024 | Kaplan et al. |

FOREIGN PATENT DOCUMENTS

| | | |
|---|---|---|
| CN | 102985014 | 3/2013 |
| CN | 104918559 | 9/2015 |
| CN | 205493920 | 8/2016 |
| CN | 106473791 | 3/2017 |
| CN | 106163425 | 1/2022 |
| DE | 102006056283 | 6/2008 |
| EP | 1223890 B1 | 4/2004 |
| EP | 1227770 B1 | 9/2004 |
| EP | 1225843 B1 | 2/2005 |
| EP | 1 347 716 | 4/2008 |
| EP | 2 387 951 | 12/2012 |
| EP | 1469790 B1 | 10/2016 |
| EP | 3085310 A1 | 10/2016 |
| EP | 2872051 B1 | 3/2017 |
| EP | 3 531 926 A2 | 9/2019 |
| JP | 2002-510526 | 4/2002 |
| JP | 2003-512128 | 4/2003 |
| JP | 2003-529384 | 10/2003 |
| JP | 2012-515624 | 11/2012 |
| JP | 2012-530551 | 12/2012 |
| JP | 2014-523764 | 9/2014 |
| JP | 2014-531247 | 11/2014 |
| JP | 2014-534872 | 12/2014 |
| JP | 2015-097821 | 5/2015 |
| JP | 2015-534881 | 12/2015 |
| JP | 2016-518155 | 6/2016 |
| JP | 2016-202905 | 12/2016 |
| JP | 2017-502788 | 1/2017 |
| JP | 2021-522896 | 9/2021 |
| WO | WO 00/27292 | 5/2000 |
| WO | WO 03/063732 | 8/2003 |
| WO | WO 2009/009466 | 1/2009 |
| WO | WO 2010/148246 | 12/2010 |
| WO | WO 2013/067188 | 5/2013 |
| WO | WO 2014/011865 | 1/2014 |
| WO | WO 2014/078531 | 5/2014 |
| WO | WO 2014/164572 | 10/2014 |
| WO | WO2016/033170 | 3/2016 |
| WO | WO 2017/066197 | 4/2017 |
| WO | WO 2017/161283 | 9/2017 |
| WO | WO 2018/081466 A2 | 5/2018 |
| WO | WO 2018/185255 | 10/2018 |
| WO | WO 2018/185256 | 10/2018 |
| WO | WO 2019/033121 | 2/2019 |
| WO | WO 2019/212894 | 11/2019 |
| WO | WO 2020/163507 | 8/2020 |
| WO | WO 2020/185389 | 9/2020 |
| WO | WO 2022/182565 | 9/2022 |

OTHER PUBLICATIONS

International Search Report and Written Opinion from PCT Application PCT/US2017/058600 dated Jun. 13, 2018.

International Search Report and Written Opinion from PCT Application PCT/US2022/016766 dated Jul. 5, 2022.

Möbius-Winkler, S., Sandri, M., Mangner, N., Lurz, P., Dahnert, I., Schuler, G. The Watchman Left Atrial Appendage Closure Device for Atrial Fibrillation. J. Vis. Exp. (60), e3671, DOI : 10.3791/3671 (Feb. 28, 2012).

Extended European Search Report in European Patent Case No. EP 14 77 9640 dated Sep. 30, 2016.

International Search Report and Written Opinion dated Jan. 19, 2017, in International Application No. PCT/US2016/056450.

International Search Report and Written Opinion dated Jul. 3, 2014, in International Application No. PCT/US2014/022865.

International Search Report dated Jul. 10, 2019, in International Application No. PCT/US2019/29364.

International Search Report issued in International Patent Application No. PCT/US2020/016854, dated Jun. 8, 2020.

Saliba et al., "Enhanced Thromboresistance and Endothelialization of a Novel Fluoropolymer-Coated Left Atrial Appendage Closure Device", JACC: Clinical Electrophysiology, May 18, 2023, vol. 9, No. 8, Part 2, pp. 13.

\* cited by examiner

DEVICES AND METHODS FOR EXCLUDING THE LEFT ATRIAL APPENDAGE

CROSS-REFERENCE TO RELATED APPLICATIONS

This application is a continuation-in-part of U.S. patent application Ser. No. 16/782,871, filed Feb. 5, 2020, and titled "Devices and Methods for Excluding the left Atrial Appendage," which claims the priority benefit of U.S. Provisional Patent Application No. 62/803,289, filed Feb. 8, 2019, the entire disclosure of each of which is hereby incorporated by reference herein in its entirety.

BACKGROUND

Field

This development relates generally to systems, devices and methods for excluding the left atrial appendage (LAA). In particular, systems, devices and methods for excluding the LAA using an expandable foam implant with a deployable and compliant frame are described herein.

Description of the Related Art

Atrial fibrillation (Afib) is a condition in which the normal beating of the left atrium (LA) is chaotic and ineffective. The left atrial appendage (LAA) is a blind pouch off the LA. In patients with Afib, blood stagnates in the LAA facilitating clot formation. These clots (or clot fragments) have a tendency to embolize or leave the LAA and enter the systemic circulation. A stroke occurs when a clot/clot fragment embolizes and occludes one of the arteries perfusing the brain. Anticoagulants, e.g. Coumadin, have been shown to significantly reduce the stroke risk in Afib patients. These drugs reduce clot formation but also increase bleeding complications including hemorrhagic strokes, subdural hematoma, and bleeding in the gastrointestinal tract.

There are about eight million people in the US and EU with Afib. About 4.6 million of these patients are at a high risk for stroke and would benefit from anticoagulation. A large portion of these patients cannot take anticoagulants due to an increased bleeding risk, leaving their stroke risk unaddressed. The prevalence of Afib increases with age.

Existing devices for occluding the LAA have drawbacks. Existing devices are offered in many sizes and must be closely matched to the highly variable LAA anatomy. This is difficult to do using fluoroscopy and often requires adjunctive imaging in the form of transesophageal echocardiography (TEE), cardiac CT and MRI, all with three dimensional reconstructions. If the device is significantly oversized, the LAA ostium may become overstretched leading to tearing, resulting in bleeding into the pericardial space. If the device is too small, it will not adequately seal the ostium and may be prone to embolization. Even if sized correctly, the device forces the oval LAA ostium to take the round shape of the device, often resulting in residual leakage at the edges due to poor sealing.

Existing devices require sufficient spring force or stiffness to seal and anchor to surrounding tissue. If too stiff, these devices may lead to leaking of blood through the tissue into the pericardial space which may lead to cardiac tamponade. Furthermore, the geometry of these devices limits repositioning once the implant is fully expanded. Existing devices also complicate delivery by requiring positioning in the LAA coaxial to the axis of the LAA.

There is therefore a need for an improved LAA occlusion device.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for left atrial appendage (LAA) occlusion.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

Devices and methods are described for occluding the LAA (LAA) to exclude the LAA from blood flow to prevent blood from clotting within the LAA and subsequently embolizing, particularly in patients with atrial fibrillation. An LAA occlusion device is delivered via transcatheter delivery into the LAA and anchored using a compliant frame and foam body. The device conforms to the oval shape of the LAA with superior sealing effect, does not require an excessive number of sizes and thus negates the need for extensive pre-procedure imaging, and can be delivered off-axis thereby allowing for simpler delivery procedure, among other advantages.

A foam body, which can be tubular in shape, and a compliant frame inside or within the foam body, are described that are collapsed for delivery and then expand in place within the LAA. The device is anchored by structural anchors of the frame and/or by tissue ingrowth from the left atrium (LA) and LAA into the foam. In one aspect, a conformable left atrial appendage occlusion device is described. The device comprises an expandable tubular body and a self-expandable support. The expandable tubular body has a compressible open cell foam sidewall, a proximal, occlusive end for facing a left atrium following implantation of the device in a left atrial appendage, a distal end for facing into the left atrial appendage following implantation of the device in the left atrial appendage, and a longitudinal axis extending therethrough, the tubular foam body having a mean diameter in an unconstrained expansion. The self-expandable support is carried within the expandable tubular body such that the foam sidewall provides a cushion between the support and the wall of the left atrial appendage following implantation, the support comprising a plurality of struts forming a plurality of apexes. Compression of the device from a diameter of about 35 mm to a diameter of about 20 mm along a minor axis transverse to the longitudinal axis causes no more than about a 5 mm reduction in the mean diameter.

There are various embodiments of the various aspects. For example, compression of the device from a diameter of about 35 mm to a diameter of about 20 mm along a minor axis transverse to the longitudinal axis may cause no more than about a 2 mm reduction in the mean diameter. The support may comprise a plurality of distally facing apexes, and the tubular foam body extends distally beyond the distal apexes to provide an atraumatic distal bumper. The conformable left atrial appendage occlusion device may further comprise at least one anchor. The expandable body may be compressed within a delivery catheter having an inside diameter of no more than about 20 F and self-expand to a diameter of at least about 35 mm when released from the delivery catheter. Application of 0.10 lbs compressive force along a minor axis transverse to the longitudinal axis may produce a compression of at least about 0.25 inches along the minor axis. Application of 0.20 lbs compressive force along the minor axis may produce a compression of at least about 0.5 inches along the minor axis. The side wall may have an uncompressed thickness of at least about 0.5 mm. The side wall may extend in a distal direction beyond a distal end of the support by at least about 2 mm in an unconstrained, expanded state. The foam sidewall may comprise a reticulated, cross linked matrix having at least about 90% void content, an average pore size within the range of from about 250-500 microns, a wall thickness of at least about 2 mm, and wherein a pressure required to compress the foam to 50% strain is at least about 1 psi. The pressure required to compress the foam to 50% strain may be within a range of from about 1 psi to about 2 psi. The self-expandable support may comprise one or more recapture struts extending radially in an unconstrained configuration.

In another aspect, a conformable left atrial appendage occlusion device is described. The device comprises an expandable tubular body and a self-expandable support. The expandable tubular body has a compressible open cell foam sidewall, a proximal, occlusive end for facing a left atrium following implantation of the device in a left atrial appendage, a distal end for facing into the left atrial appendage following implantation of the device in the left atrial appendage, and a longitudinal axis extending therethrough, the tubular foam body having a mean diameter in an unconstrained expansion. The self-expandable support is carried within the expandable tubular body such that the foam sidewall provides a cushion between the support and the wall of the left atrial appendage following implantation, the support comprising a plurality of struts forming a plurality of apexes. Compression of the device from a diameter of about 35 mm to a diameter of about 25 mm along a minor axis transverse to the longitudinal axis causes an elongation of at least about 6 mm along a major axis transverse to the minor axis. In some embodiments, compression of the device from a diameter of about 35 mm to a diameter of about 25 mm along the minor axis may cause an elongation of at least about 8 mm along the major axis.

In another aspect, a conformable left atrial appendage occlusion device is described. The device comprises an expandable tubular body and a self-expandable support. The expandable tubular body has a compressible open cell foam sidewall, a proximal, occlusive end for facing a left atrium following implantation of the device in a left atrial appendage, a distal end for facing into the left atrial appendage following implantation of the device in the left atrial appendage, and a longitudinal axis extending therethrough, the tubular foam body having a mean diameter in an unconstrained expansion. The self-expandable support is carried within the expandable tubular body such that the foam sidewall provides a cushion between the support and the wall of the left atrial appendage following implantation, the support comprising a plurality of struts forming a plurality of apexes. Application of 0.10 lbs compressive force along a minor axis transverse to the longitudinal axis produces a compression of at least about 0.2 inches along the minor axis.

There are various embodiments of the various aspects. For example, application of 0.20 lbs compressive force along the minor axis may produce a compression of at least about 0.5 inches along the minor axis. Application of no more than about 0.30 lbs compressive force along the minor axis may produce a compression of at least about 0.6 inches along the minor axis. The side wall may have an uncompressed thickness of at least about 0.5 mm. The side wall may have an uncompressed thickness of at least about 1.5 mm. The foam sidewall may comprise a reticulated, cross linked matrix having at least about 90% void content, an average pore size within the range of from about 250-500 microns, and a wall thickness of at least about 2 mm, and a pressure required to compress the foam to 50% strain may be at least about 1 psi. The pressure required to compress the foam to 50% strain may be within a range of from about 1 psi to about 2 psi.

In another aspect, a loading system for loading an expandable implant into a deployment catheter is described. The loading system comprises a delivery catheter having a proximal end and a distal end, a tapered chamber located at the distal end of the delivery catheter and having a small diameter proximal end and a large diameter distal end, and a hydraulic loader located at the proximal end of the delivery catheter. Actuation of the hydraulic loader causes the implant to advance proximally through the tapered chamber and into the distal end of the delivery catheter.

There are various embodiments of the various aspects. The hydraulic loader may comprise a first piston actuator configured to advance by applying a first force F1, a second piston actuator in fluid communication with the first piston actuator and configured to receive a second force F2 in response to the applied force F1, and where F1 is less than F2. The hydraulic loader may comprise a first piston actuator having a first cross-sectional area in fluid communication with a second piston actuator having a second cross-sectional area that is greater than the first cross-sectional area, where the second piston actuator is configured to advance proximally in response to manual activation of the first piston actuator. The first piston actuator may comprise a syringe configured to receive a first moveable plunger and the second piston actuator may comprise a barrel configured to couple with a second moveable plunger. The hydraulic loader may comprise a piston actuator having a distal end fixed relative to the delivery system and a proximal end configured to advance proximally relative to the delivery system in response to actuation. The loading system may further comprise an elongate, flexible pusher and a tether extending through the pusher and detachably connected to the implant. The loading system may further comprise a hand piece at a proximal end of the pusher, the hand piece having a control for moving between a first, transvascular navigation configuration in which the implant is held by the tether in close proximity to a distal end of the pusher, and a second, test configuration in which the distal end of the pusher may be moved a distance away from the implant without changing the orientation of the implant, while the tether is still attached to the implant.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

Figure 1:
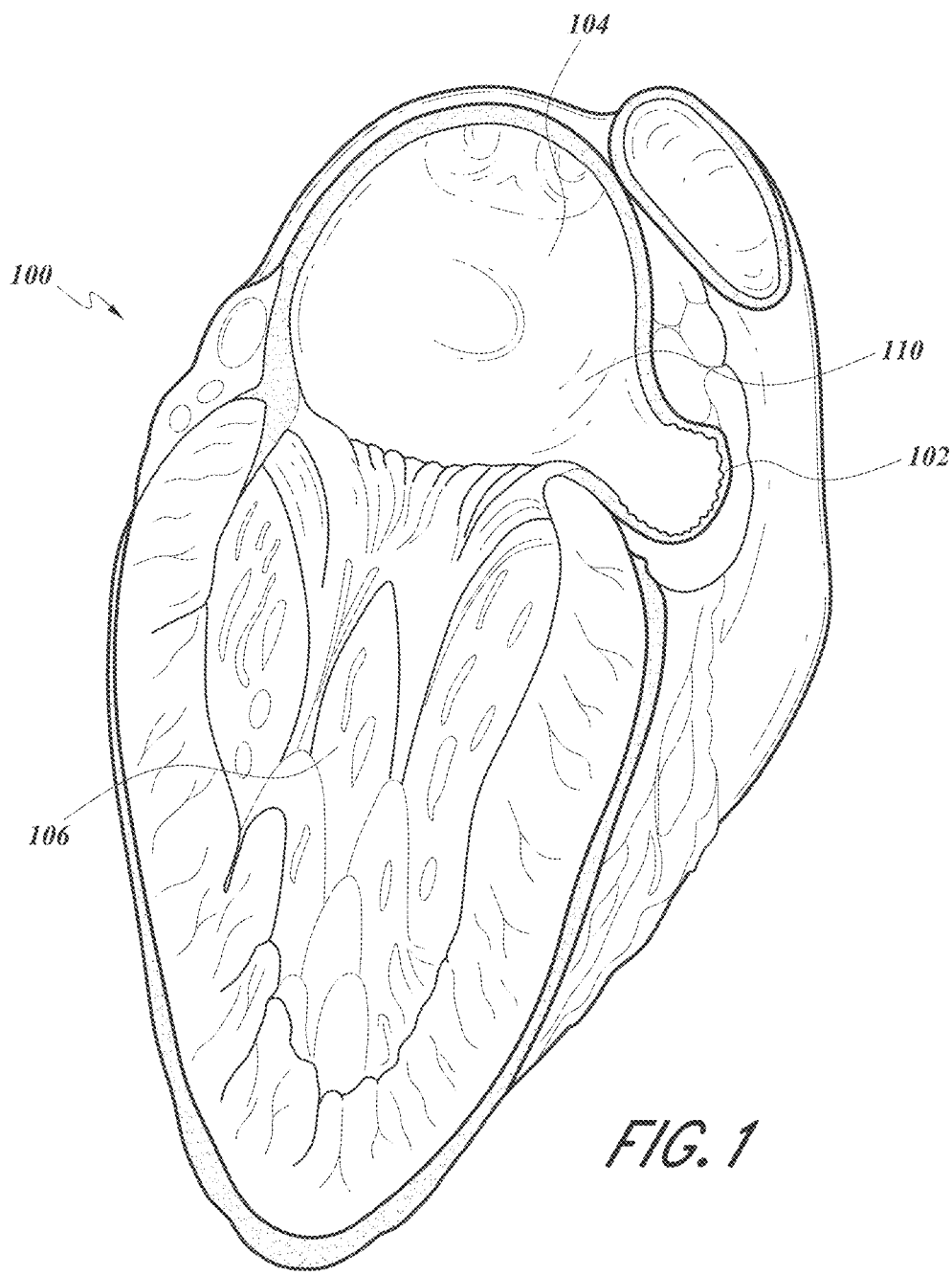
FIG. 1 shows the anatomy of the left atrium (LA) and left atrial appendage (LAA).

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

The devices and related methods are described herein in connection with use in occluding, i.e. excluding, a left atrial appendage (LAA). The various figures show various embodiments of LAA occlusion devices, systems and methods for delivery of the LAA occlusion devices, and/or methods of using the device to occlude a LAA. The various systems, devices and methods described herein may include the same or similar features and/or functionalities as other LAA occlusion systems, devices and methods as described, for example, in U.S. application Ser. No. 14/203,187 entitled "DEVICES AND METHODS FOR EXCLUDING THE LAA" and filed on Mar. 10, 2014, and/or as described in U.S. Provisional Application No. 62/240,124 entitled "DEVICES AND METHODS FOR EXCLUDING THE LAA" and filed on Oct. 12, 2015, the entire disclosure of each of which is incorporated herein by reference for all purposes and forms a part of this specification.

Some embodiments of an LAA occlusion device 3000 include a foam body 3002, a deployable and compliant frame 3040, and a proximal cover 3100, as primarily shown and described for example with respect to FIGS. 3A-8D. Other features and functionalities that the device 3000 may include and employ are shown and described with respect to FIGS. 1-23 and 30-11B.

The heart 100 is shown in FIG. 1 with the left atrial appendage (LAA) 102, which is a cavity emanating from the left atrium (LA) 104. The LAA 102 is quite variable in shape in all dimensions. If the heart is not beating normally, a condition called atrial fibrillation, blood within the LAA becomes stagnant which promotes clot formation. If blood clots within the LAA, the clots may pass from the LAA 102 to the LA 104, to the left ventricle 106 and out of the heart 100 into the aorta. Vessels that bring blood to the brain branch off the aorta. If the clot passes to the brain via these vessels, it may get stuck and occlude a small vessel in the brain which then causes an ischemic stroke. Strokes have severe morbidities associated with them. The opening of the LAA 102 to the LA 104 is called an ostium 110. The ostium 110 is oval, highly variable and dependent on loading conditions, i.e., left atrial pressure. An object of the LAA occlusion devices described herein is to occlude the ostium 110 thereby sealing off the LA 104 from the LAA 102.

Figure 2:
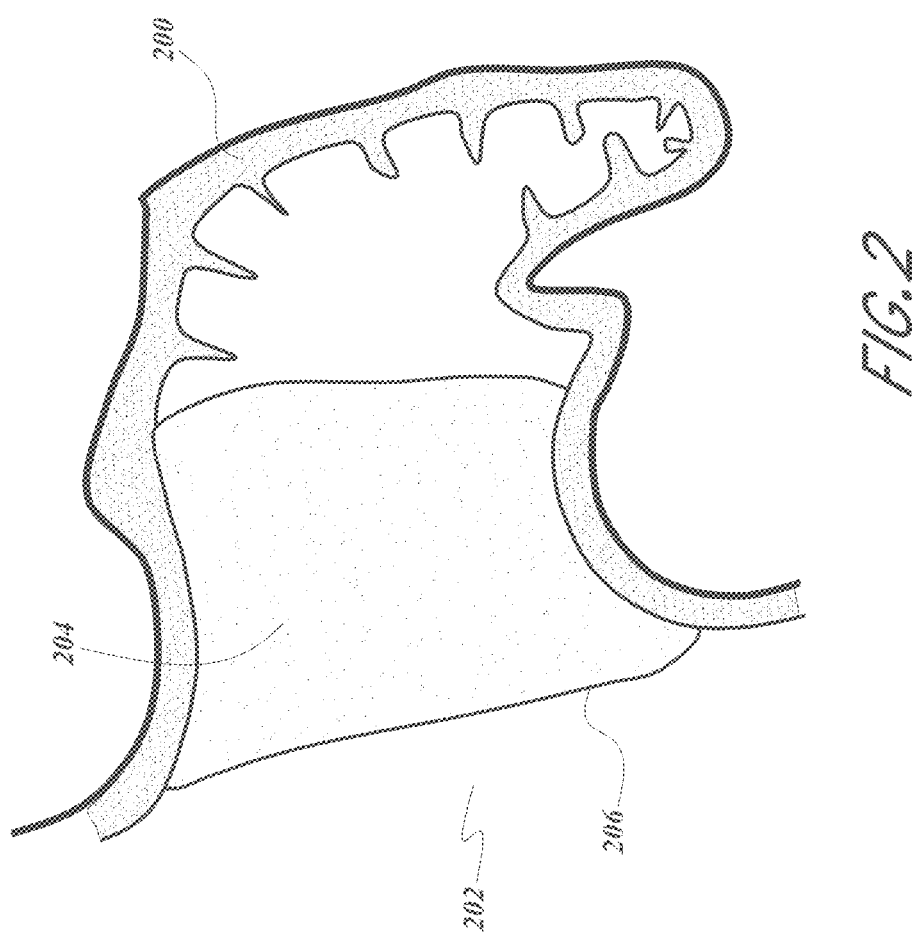
FIG. 2 shows an LAA with an embodiment of an LAA occlusion device implanted in the LAA.

One embodiment of an LAA occlusion device 204 is shown in FIG. 2. The occlusion device 204 is placed within the LAA 200 at its opening to the LA 202. It is understood that the device 204 may have the same or similar features as other implantable "devices" or "implants" described herein, such as the implant 3000, and vice versa. The device 204 may thus have an expandable foam body carrying a support structure or frame with anchors, as described herein, for example with respect to the implant 3000 and FIGS. 3A-8D.

The device 204 may be cylindrical in shape in an unconstrained expansion, but it may also be conical for example with its distal end smaller than the proximal end or reversed. It could also be oval in cross section to better match the opening of the LAA.

The device 204 is oversized radially in an unconstrained expansion to fit snuggly into the LAA and may be 5-50 mm in diameter depending on the diameter of the target LAA. The compliance and thickness of the foam are designed to provide a good seal against the tissue with minimal compression. While other devices require significant oversizing relative to the width of the LAA to obtain a seal, the implants described herein may require only ≤1 mm of oversizing. In some embodiments, the implant may require only ≤2 mm, ≤3 mm, or ≤4 mm, or ≤5 mm. In a free, unconstrained state, the axial length "L" of the plug is less than its outer diameter "D" such that the L/D ratio is less than 1.0. In some embodiments, this ratio may be greater than 1.0. The compliance of the foam material is designed such that it pushes on the walls of the LAA with sufficient force to maintain the device 204 in place but without overly stretching the LAA wall. The foam and/or skin also conforms to the irregular surfaces of the LAA as it expands, to provide a complementary surface structure to the native LAA wall to further enhance anchoring and promote sealing. Thus, the expandable foam implant described herein conforms to the native configuration of the LAA. In one embodiment, the structure of the foam may be fabricated such that squeezing axially on the opposing ends of the foam causes the foam to increase in diameter.

An outer ePTFE layer may be formed as a sheet. The sheet may have a wall thickness between 0.0001" and about 0.001" thick and serves to allow one to collapse and pull on the device 204 without tearing the foam material. In other embodiments, an outer ePTFE layer may be formed from a tube with a diameter about the same diameter of the foam plug and a wall thickness between about 0.0001" and about 0.001" thick and serves to allow one to collapse and pull on the device 204 without tearing the foam material. The ePTFE material also serves as the blood contacting surface facing the LA 206 and has pores or nodes such that blood components coagulate on the surface and an intimal or neointimal covering of tissue grows across it and anchors tightly to the material. Pore sizes within the range of from about 4μ to about 110μ, ideally 5-35μ are useful for formation and adherence of a neointima.

The outer covering 206 may be constructed of materials other than ePTFE such as woven fabrics, meshes or perforated films made of FEP, polypropylene, polyethylene, polyester or nylon. The covering 206 should have a low compliance (non-elastic), at least longitudinally, be sufficiently strong as to permit removal of the plug, a low coefficient of friction, and be thromboresistant. The outer covering 206 serves as a matrix to permit plug removal as most foams are not sufficiently strong to resist tearing when pulled. The plug 204 can also be coated with or contain materials, such as PTFE. Such materials may enhance the plug's 204 ultrasonic echogenic profile, thromboresistance, and/or lubricity. The plug 204 can also be coated with or contain materials to facilitate echocardiographic visualization, promote cellular ingrowth and coverage.

The outer covering 206 has holes in it to permit contact of the LAA tissue with the device 204 to encourage ingrowth of tissue into the foam plug pores and/or allow blood flow therethrough. These holes may be 1 to 5 mm in diameter or may also be oval with their long axis aligned with the axis of the foam plug, the length of which may be 80% of the length of the foam plug and the width may be 1-5 mm. The holes may be as large as possible such that the outer covering maintains sufficient strength to transmit the tensile forces required for removal. The holes may be preferentially placed along the device. In one embodiment, holes are placed distally to enhance tissue ingrowth from the LAA wall.

The device 204 or 3000 (as described below) may be anchored and secured in place in the LAA by anchoring features. In some embodiments, the device 204 or 3000 may also be anchored by tissue ingrowth.

Deployment of the occlusion device may be via transvascular access. However, the implants may alternatively be deployed via direct surgical access, or various minimally invasive access pathways (e.g. jugular vein). For example, the area overlying the xiphoid and adjacent costal cartilage may be prepared and draped using standard techniques. A local anesthetic may be administered and skin incision may be made, typically about 2 cm in length. The percutaneous penetration passes beneath the costal cartilage, and a sheath may be introduced into the pericardial space. The pericardial space may be irrigated with saline, preferably with a saline-lidocaine solution to provide additional anesthesia and reduce the risk of irritating the heart. The occlusion device may thereafter be introduced through the sheath, and through an access pathway created through the wall of the LAA. Closure of the wall and access pathway may thereafter be accomplished using techniques understood in the art.

Various features for LAA occlusion may be included in the LAA occlusion devices, systems, and methods described herein, such as those described, for example, in U.S. patent application Ser. No. 15/290,692, filed Oct. 11, 2016 and titled DEVICES AND METHODS FOR EXCLUDING THE LAA, in U.S. patent application Ser. No. 14/203,187, filed Mar. 10, 2014 and titled DEVICES AND METHODS FOR EXCLUDING THE LAA, in European Patent Application no. EP 14779640.3, filed Aug. 24, 2015 and titled DEVICES AND METHODS FOR EXCLUDING THE LAA, and in PCT Patent Application no. PCT/US2014/022865, filed Mar. 10, 2014 and titled DEVICES AND METHODS FOR EXCLUDING THE LAA, the entire disclosure of each of which is hereby expressly incorporated by reference for all purposes and forms a part of this specification. Further additions and improvements to these and other concepts are described below. The embodiments described in the sections below may include the same or similar features and/or functionalities as the embodiments described above, and vice versa, except as otherwise noted or indicated by context.

A. LAA Occlusion Device Embodiments with Compressible Foam Body, Proximal Cover, and Compliant Frame Having Proximal Recapture Struts and Distal Tubular Body FIGS. 3A-11B show an embodiment of an LAA occlusion device 3000. The device 3000 described herein may have the same or similar features and/or functionalities as other LAA occlusion devices described herein, and vice versa. Any of the features of the device 3000 described with respect to FIGS. 3A-11B may therefore apply to features of the devices described with respect to FIG. 2, such as the device 204, and vice versa.

Figure 3A:
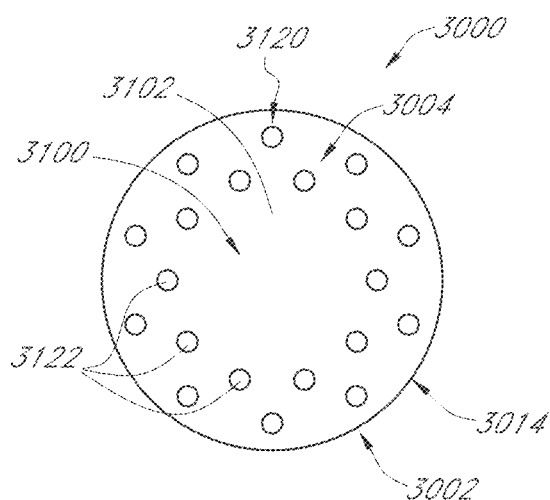
FIGS. 3A-3C are proximal, distal and side views, respectively, of an embodiment of an LAA occlusion device having a compressible foam body, an expandable frame, and a proximal cover.
Figure 3B:
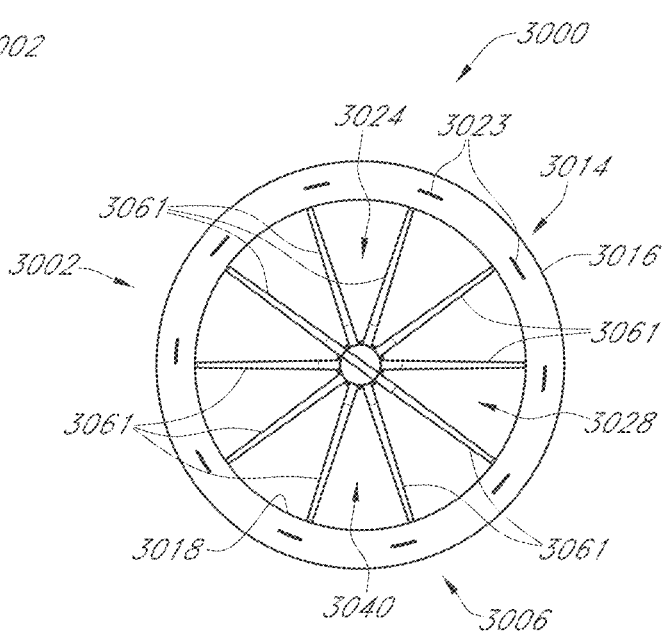
Figure 3C:
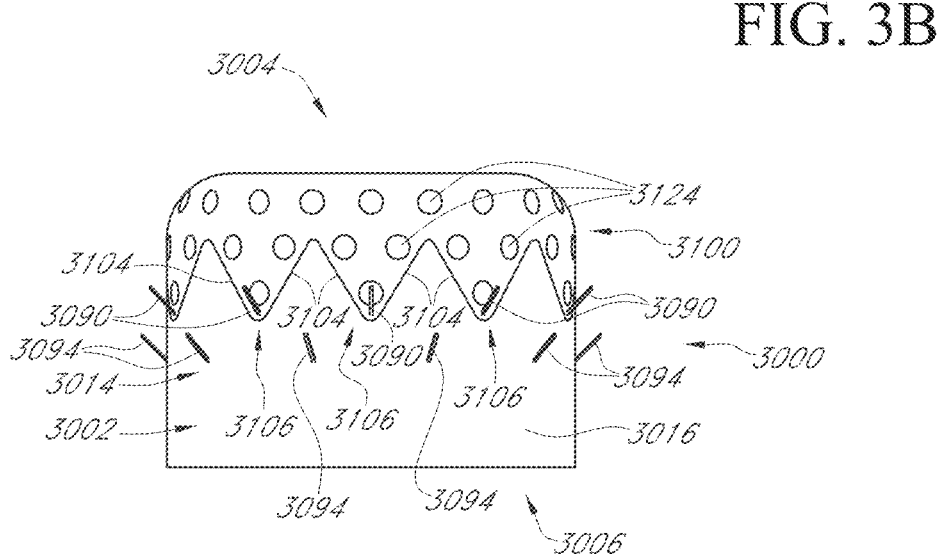
Figure 3D:
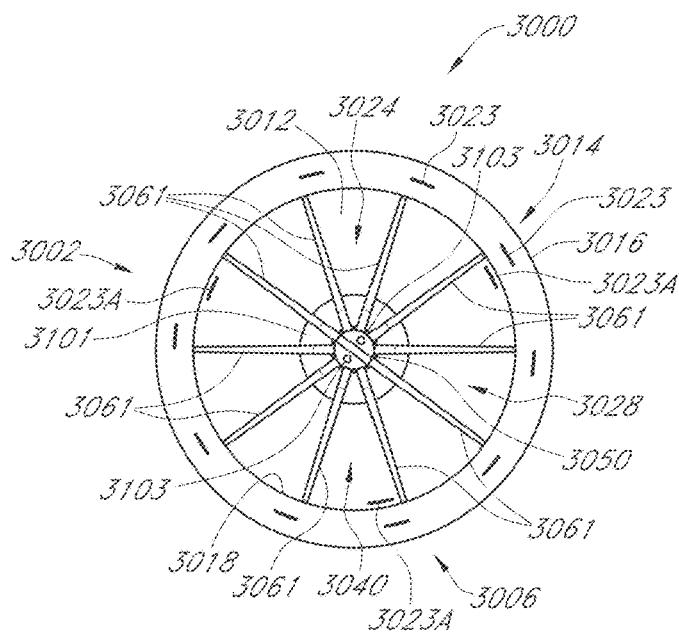
FIG. 3D is a distal view of the embodiment of the LAA occlusion device of FIGS. 3A-3C additionally having an interior cover and proximal markers.
Figure 4A:
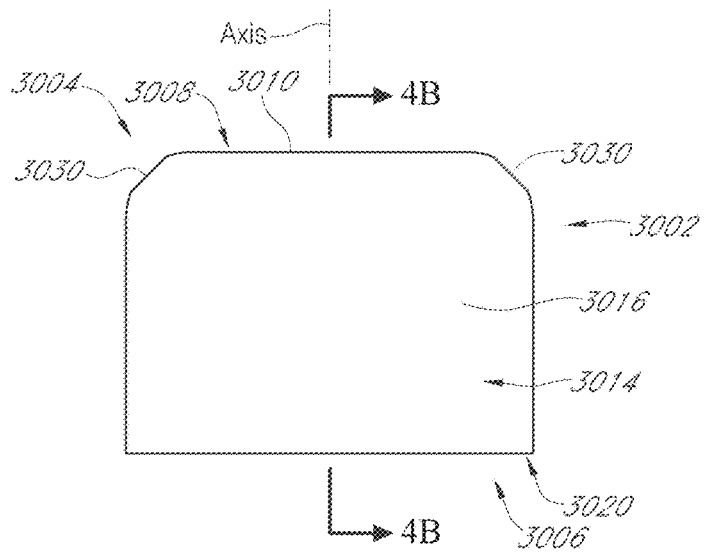
FIGS. 4A-4B are side and cross-section views, respectively, of the compressible foam body of FIGS. 3A-3C.
Figure 4B:
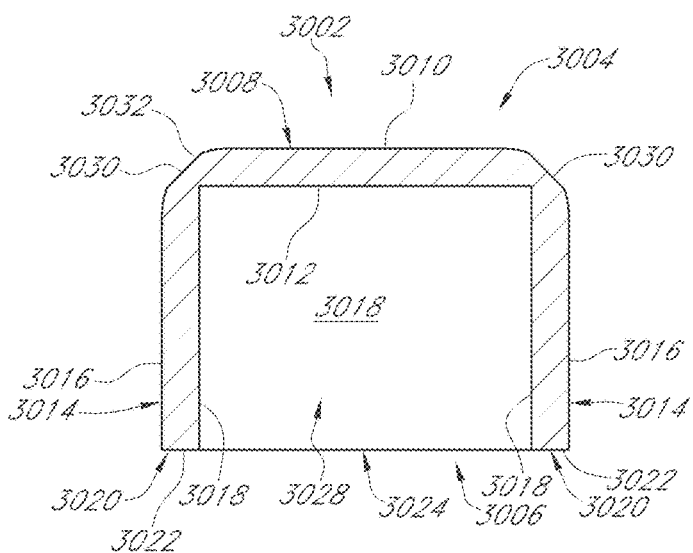
Figure 4C:
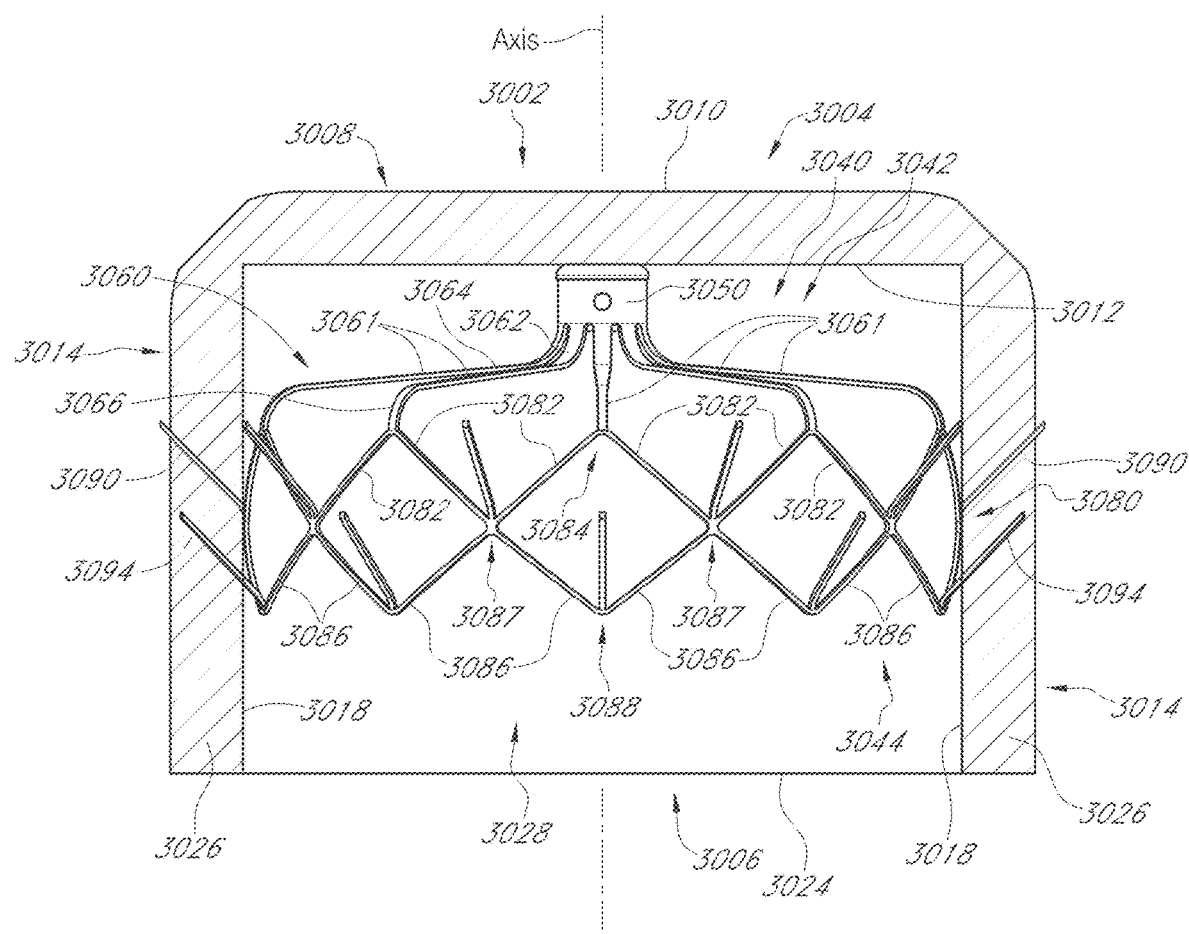
FIG. 4C is a cross-section view of the foam body of FIGS. 3A-3C with the expandable frame.

FIGS. 3A-3C show the LAA occlusion device 3000 having a foam body 3002, an expandable support or frame 3040, and a proximal cover 3100. FIG. 3D shows the LAA occlusion device 3000 additionally having an interior cover 3101 and proximal markers 3023A. FIGS. 4A-4C show the foam body 3002, with the body 3002 shown in cross-section in FIGS. 4B and 4C. FIG. 4C additionally includes the full view (i.e. non-cross section) of the frame 3040. The device 3000 is shown in an expanded configuration in these figures. The device 3000 has a longitudinal axis as shown, which may be defined by the foam body 3002, as further described.

1. Compressible Foam Body

The body 3002 is formed from a compressible material, such as foam. The body 3002 may be a foam formed from reticulated (e.g. net-like) polycarbonate polyurethane-urea. The body 3002 may be cut, formed or assembled into a cup shape, as further described. The body 3002 may have a thickness and compressibility sufficient to engage the surrounding tissue and conform to the anatomic irregularities under radial force applied by the inner frame, as further described. The use of a compressible material such as foam for the body 3002 provides a complete seal of the LAA and superior performance for LAA occlusion over existing devices, as further described. The structure of the foam of the body 3002 comprises a three-dimensional network of interconnected reticulations, spaced apart to form a network of interconnected open pores, as further described. The reticulations can carry a coating, such as PTFE, while preserving the open pores, as further described.

The foam material of the body 3002 has a high porosity. "Porosity" as used herein has its usual and customary meaning and refers to open void content between the interconnected reticulations of the foam. The porosity of the body 3002 may be at least about 65%, at least about 70% at least about 75%, at least about 80%, at least about 85%, at least about 90%, at least about 95% or more. The porosity may be within the range of approximately 90-95%. The porosity may be approximately 90%. The porosity may be approximately 95%. The porosity may be 90%, 91%, 92%, 93%, 94%, or 95%. The high porosity promotes quick and tenacious tissue ingrowth, allows it to be compressed into a small catheter, and/or allows blood to pass if the implant embolizes, among other advantages.

The foam body 3002 has pores or cells formed between the interconnected reticulations of the foam material. The foam body 3002 has cells with sizes in the range of from about 250 μm to about 500 μm. The foam may have a cell size from about 125 μm to about 750 μm, from about 175 μm to about 650 μm, from about 200 μm to about 600 μm, from about 225 μm to about 550 μm, from about 275 μm to about 450 μm, less than 125 μm, or greater than 750 μm. These sizes may refer to the size of the cell prior to application of any coating, such as PTFE. The cell size may thus change, e.g. decrease, after application of the coating. The desired porosity and/or cell size may be determined based on allowing the passage of blood while blocking debris of a size capable of potentially causing ischemic stroke. The allowable size of such debris may drive the selection of the particular porosity and/or cell size. For example, the cell size from about 250 μm to about 500 μm may be based on prevention of debris of a particular size from passing through the body 3002.

In an embodiment, the foam body 3002 is made from a non-resorbable, reticulated, cross-linked, polycarbonate polyurethane-urea matrix, structurally designed to support fibrovascular tissue ingrowth, with a fully interconnected, macroporous morphology with over 90-95% void content and cell sizes ranging from 250 to 500 μm.

The body 3002 has a proximal end 3004 and a distal end 3006. In some embodiments, the axial length of the device 3000 from the proximal end to the distal end in a free, unconstrained state is 20 mm. As used herein, the "free, unconstrained" state, and the like, refers to a state of the device 3000 without any external forces applied to the device 3000 other than a normal or reactive force from a surface (e.g. table top) on which the device 3000 is placed. In some embodiments, this axial length may be from about 10 mm to about 30 mm, from about 12 mm to about 28 mm, from about 14 mm to about 26 mm, from about 16 mm to about 24 mm, from about 18 mm to about 22 mm, or about 20 mm. The body 3002 may have any of these lengths regardless of outer diameter of the body 3002.

The proximal end 3004 of the body 3002 has a proximal end wall or face 3008. The proximal face 3008 faces generally toward the LA when the device 3000 is implanted into the LAA. The device 3000 may be implanted off-axis, as further described, in which case the proximal face 3008 may not reside at a perpendicular to a longitudinal axis of the LA. The proximal face 3008 thus provides a closed proximal end 3004 of the body 3002. The closed proximal end 3004 is configured to span the ostium but the porosity, as further described, is sufficient to permit the passage of blood while blocking debris of a size capable of potentially causing ischemic stroke. This membrane may be formed by the body 3002 and/or the cover 3100. In some embodiments, the proximal face 3008 or portions thereof may be open. For example, there may not be a proximal face 3008, there may be a partial proximal face 3008, there may be a proximal face 3008 with portions removed, etc. In some embodiments, the proximal face 3008 or portions thereof is/are not included and any opening or openings is/are covered by the cover 3100. The size of any such openings in the proximal face 3008 may be driven by the desired size of embolic debris to be prevented from escaping the LAA, as further described.

The proximal face 3008 is flat or generally flat and generally perpendicular to the longitudinal axis of the device 3000. The proximal face 3008 has a circular or generally circular shape as viewed from the proximal end 3004 in an unconstrained expansion. In some embodiments, the proximal face 3008 may be flat, rounded, segmented, angled with respect to the longitudinal axis, other shapes, or combinations thereof. The proximal face 3008 may have a non-circular, polygonal, other rounded shape, other shapes, or combinations thereof, as viewed from the proximal end 3004.

The proximal face 3008 has an outer surface 3010 and an opposite inner surface 3012. The outer surface 3010 faces proximally away from the device 3000 and the inner surface 3012 faces distally toward the frame 3040. The surfaces 3010, 3012 may define outer and inner sides of the proximal face 3008. The thickness of the proximal face 3008 may be measured axially between the outer surface 3010 to the inner surface 3012. This thickness in a free, unconstrained state (e.g. uncompressed and expanded) may be from about 0.5 mm to about 5 mm, from about 1 mm to about 4 mm, from about 2 mm to about 3 mm, about 2.5 mm, or 2.5 mm. In some embodiments, the thickness may be less than 0.5 mm or greater than 5 mm. The thickness of the proximal face 3008 may be uniform or non-uniform. Thus the thickness may be greater or smaller in different regions of the proximal face 3008.

The body 3002 includes a sidewall 3014 extending distally from the proximal face 3008. The sidewall 3014 extends circumferentially about a perimeter of the proximal face 3008 to form a closed cross-section (i.e. extends circumferentially 360 degrees about the axis). The sidewall 3014 extends axially to define a tubular body concentric about the longitudinal axis of the device 3000. The longitudinal axis extends through a geometric center of the tubular body defined by sidewall 3014. The sidewall 3014 is tubular or generally tubular, e.g. cylindrical, along the axis. In some embodiments, the sidewall 3014 may be conical or frustoconical, for example where the proximal end is wider than the distal end or vice versa. The sidewall 3014 may have an outer profile at the proximal end thereof, and as viewed from the proximal or distal end, to match that of the outer perimeter of the proximal face 3008.

In some embodiments, the cross-section of the sidewall 3014 may not be closed, for example where there are openings in the sidewall 3014. Thus cross-sections taken at various locations along the longitudinal axis may or may not show a closed section. In some embodiments, the sidewall 3014 may be non-tubular, non-cylindrical, non-circular, polygonal, other rounded shapes, other shapes, or combinations thereof. In some embodiments, as shown, the sidewall 3014 may extend continuously for the entire length from the proximal end 3004 to the distal end 3006. In some embodiments, the sidewall 3014 may not extend continuously for the entire length from the proximal end 3004 to the distal end 3006. For example, the sidewall 3014 may include a plurality of disconnected sections, such as annular portions of the sidewall, located and spaced along the longitudinal axis and connected to the frame 3040.

The sidewall 3014 has an outer surface 3016 and an opposite inner surface 3018. The outer surface 3016 faces radially outward from the axis. The inner surface 3018 faces radially inward toward the axis. The thickness of the sidewall 3014 may be measured radially between the outer surface 3016 to the inner surface 3018. This thickness in a free, unconstrained state (e.g. uncompressed) may be from about 0.5 mm to about 5 mm, from about 1 mm to about 4 mm, from about 2 mm to about 3 mm, about 2.5 mm, or 2.5 mm. In some embodiments, the thickness may be less than 0.5 mm or greater than 5 mm. The thickness of the sidewall 3014 may be uniform or non-uniform. Thus the thickness may be greater or smaller in different regions of the sidewall 3014. The thickness of the sidewall 3014 may be the same or different as the thickness of the proximal face 3008. In some embodiments, the thickness of the proximal face 3008 is 2.5 mm and the thickness of the sidewall 3014 is 2.5 mm. In some embodiments, the thickness of the proximal face 3008 is about 2.5 mm and the thickness of the sidewall 3014 is about 2.5 mm.

The sidewall 3014 has a distal free end 3020 having a distal surface 3022. The distal surface 3022 is flat or generally flat and perpendicular to the longitudinal axis of the device 3000. In some embodiments, the distal surface 3022 is non-flat, angled with respect to the axis of the device 3000, curved, rounded, segmented, other shapes, or combinations thereof.

The body 3002 may have a distal opening 3024. The opening 3024 is formed by the distal free end 3020 of the sidewall 3014. The opening 3024 is at a distal end of an internal central volume or cavity 3028 of the body 3002 that is formed at least partially by the sidewall 3014, the proximal face 3008 and/or the shoulder 3030. The frame 3040 may reside within the cavity 3028, as further described. The distal opening 3024 may be completely open. In some embodiments, the distal opening 3024 may be mostly open, partially open, or closed, for example where the body 3002 has a distal face similar to the proximal face 3008 to enclose or partially enclose the cavity 3028.

The body 3002 has a shoulder 3030, shown as a bevel, that extends between the proximal face 3008 to the sidewall 3014. The shoulder 3030 may be an intersection of a proximal end of the sidewall 3014 and the proximal face 3008. The shoulder 3030 extends circumferentially about the entire perimeter of the intersection. The shoulder 3030 has an outer surface 3032. The outer surface 3032 may be a beveled surface. The outer surface 3032 is flat or generally flat in an axial direction. The outer surface 3032 extends circumferentially about the entire perimeter of the shoulder 3030. In some embodiments the shoulder 3030 and/or outer surface 3032 may be non-flat, rounded, other shapes in an axial direction, or combinations thereof. The shoulder 3030 and/or outer surface 3032 may extend circumferentially less than the entire perimeter of the shoulder 3030. The thickness of the shoulder 3030 may be measured inward perpendicularly to the outer surface 3032. The thickness of the shoulder 3030 may be the same as the thicknesses of the proximal face 3008 and/or the sidewall 3014, as described herein. In some embodiments, the thickness of the shoulder 3030 may be different from the thicknesses of the proximal face 3008 and/or the sidewall 3014. The shoulder 3030 may function as a recapture ramp, to facilitate drawing the implant proximally into the deployment catheter.

The compressibility of the body 3002 contributes to the superior sealing capability of the device 3000. The foam may be compressible to provide a larger radial "footprint" and spread out the radial forces from struts on the frame 3040, as further described. The foam body 3002 may have a compressive strength of at least 1 pound per square inch (psi) or within a range of about 1 psi to about 2 psi, or no more than about 2 psi. The "compressive strength" here refers to the pressure to compress the foam to 50% strain. With some foam materials for the body 3002, the pressure may not change from 50% strain through at least 80% strain, and the relation of pressure versus strain may be flat or generally flat. Thus, even with thicker foams for the body 3002, the body 3002 will not exert much more outward force on the tissue due to the increased thickness by itself. In an embodiment, the foam body 3002 is a reticulated, cross linked matrix having at least about 90% void content, an average cell size within the range of from about 250-500 microns, a wall thickness of at least about 2 mm and a compressive strength of at least about 1 psi. In an embodiment, the body 3002 is formed from a foam material having or substantially having the material properties indicated in Table 1. In some embodiments, the body 3002 is formed from materials described in, for example, U.S. Pat. No. 7,803,395, issued Sep. 28, 2010, and titled "Reticulated elastomeric matrices, their manufacture and use in implantable devices," or U.S. Pat. No. 8,337,487, issued Dec. 25, 2012, and titled "Reticulated elastomeric matrices, their manufacture and use in implantable devices," the entire disclosures of which are incorporated herein by reference.

TABLE 1

Example material properties for an embodiment of foam material that may be used for the foam body 3002.

| Material Property | Value |
| --- | --- |
| Permeability | 311 Darcy |
| Average Cell Size | 377 μm |
| Density | 2.7 lb/ft$^3$ |
| Compressive Strength | 1.1 psi |
| Tensile Strength Parallel | 68 psi |
| Tensile Strength Perpendicular | 32 psi |
| Elongation Parallel | 219% |
| Elongation Perpendicular | 243% |

The device 3000 may include markers 3023 (see FIGS. 3B and 5D; for clarity only some of the markers 3023 are labelled in the figures) to facilitate visualization during delivery. The markers 3023 may be radiopaque marker bands sewn into the distal free end 3020 of the body 3002. The markers 3023 may be for visualization using fluoroscopy imaging of the distal end 3006 of the device 3000 during delivery. There may be a series of the markers 3023 located circumferentially along the distal surface 3022 of the body 3002 (for clarity, only some of the markers 3023 are labelled in FIG. 3B). In some embodiments, the markers 3023 may additionally or alternatively be located in other areas of the body 3002 and/or on other parts of the device, such as the cover 3100 or frame 3040.

In some embodiments, four platinum iridium (PtIr) radiopaque (RO) tubular markers 3023 are sewn onto the distal end 3006 of the foam body 3002 to enable visualization of the distal edge of the device 3000 under fluoroscopy. In some embodiments, a PtIr marker 3023 is attached to the foam body 3002 at the location of the proximal shoulder 3030 to use as a marker during recapture of the device 3000. Visualization of the proximal and/or distal markers 3023 may facilitate with identifying the amount of recapture. If the device 3000 is recaptured up to but not including the anchors proximal 3090 inside the access sheath, the device 3000 can be redeployed and reused. If the proximal anchors 3090 are recaptured into the access sheath, the device 3000 may be removed and discarded due to permanent deformation of the anchors 3090. In some embodiments, other materials may be used for the markers 3023, such as gold or other suitable materials.

Figure 5A:
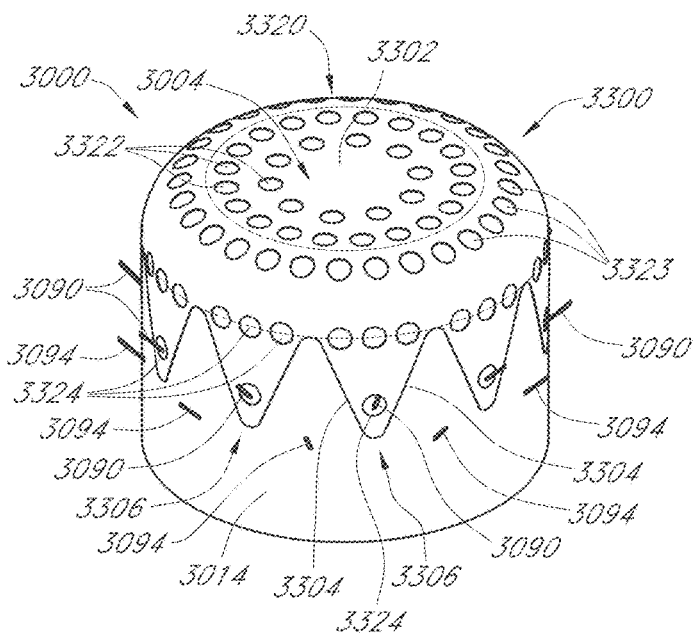
FIGS. 5A-5C are top perspective, side, and cross-section views of another embodiment of an LAA occlusion device.
Figure 5B:
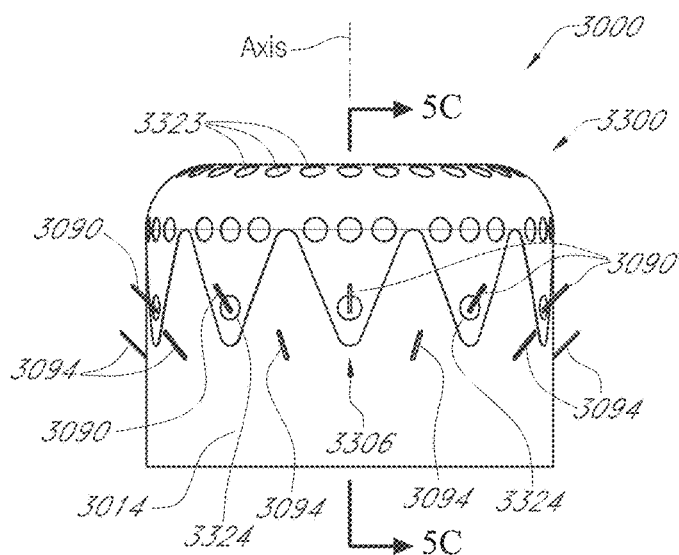
Figure 5C:
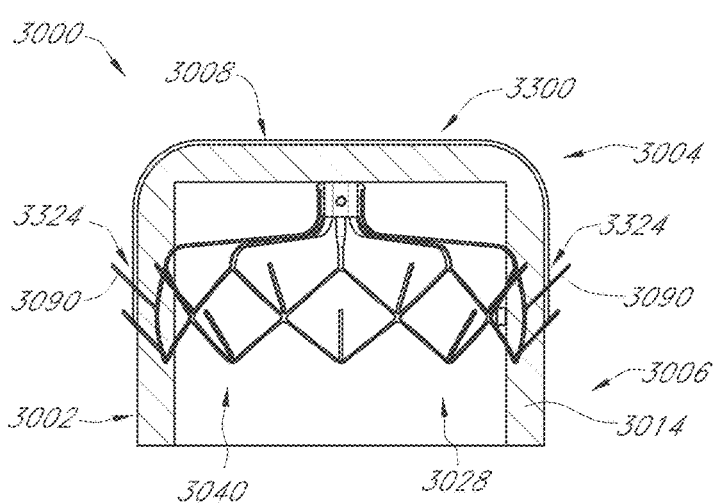
Figure 5D:
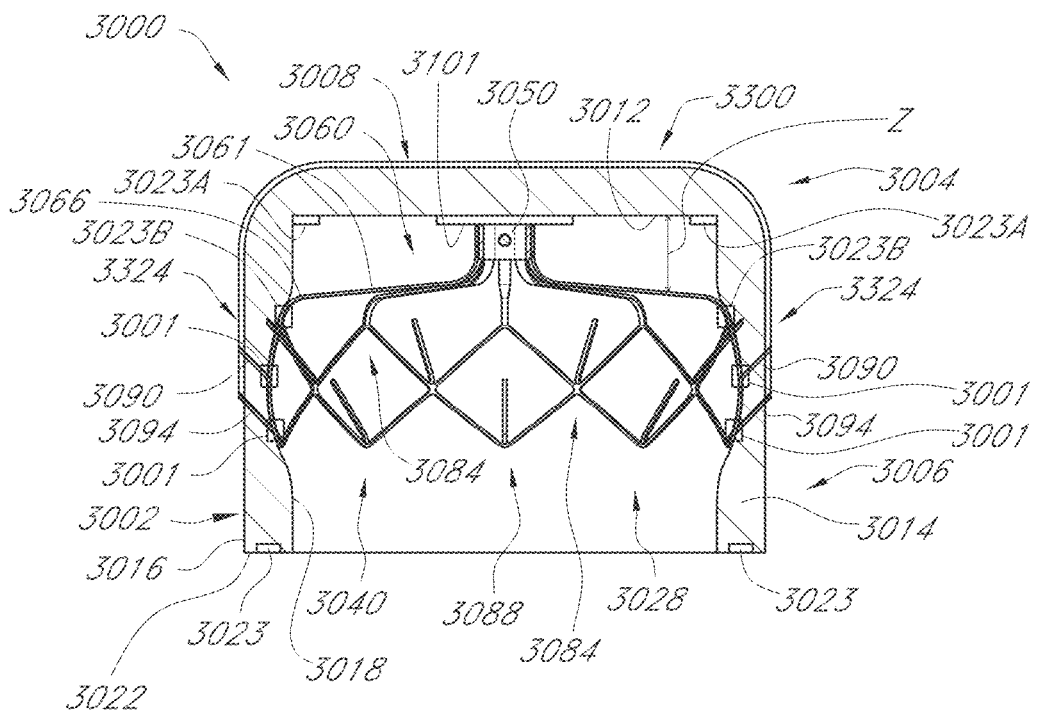
FIGS. 5D-5E are side cross-section views of various embodiments of the LAA occlusion device of FIG. 3D.

As shown in FIGS. 3D and 5D, the device 3000 may include one or more markers 3023A. As one example only, there are three markers 3023A shown. In some embodiments, there may be one marker 3023A. There may be two, four, five or more markers 3023A. In some embodiments, there is one proximal marker 3023A and ten of the distal markers 3023. The markers 3023A may have the same or similar features and/or functionalities as other markers described herein, for example the marker 3023, and vice versa, except as otherwise noted. The markers 3023A may be located at or near the proximal end of the device 3000. As shown, the markers 3023A are located on an inner surface 3012 of the proximal end 3004 of the foam body 3002. The markers 3023A may be located at or near an inner surface of a shoulder 3030 (see FIG. 4B) of the foam body 3002. The markers 3023A may be distributed circumferentially, for example equidistant or equiangular, relative to each other, or they may be at different relative distances from each other. They may be radially located at the same or different location relative to each other. In some embodiments, there is only one marker 3023A. There may be one proximal marker 3023A and four of the distal markers 3023. The one or more markers 3023A may be on the inside, outside, or within the foam body 3002, or combinations thereof. The one or more markers 3023A may be located on or at the distal surface 3022 of the foam body 3022. The markers 3023A may be elongated circumferentially as shown. In some embodiments, the markers 3023A may be linear when the device 3000 is viewed from a particular angle, such as a side view. The markers 3023A may be aligned or oriented in the same or similar orientation, or in different orientations. Some, none, or all of the markers 3023A may be oriented circumferentially, laterally, axially (for example along an inner surface 3018 of the sidewall 3014), other orientations, or combinations thereof.

As further shown in FIG. 5D, there may be one or more markers 3023B. The one or more markers 3023B may have the same or similar features and/or functionalities as the other markers described herein, such as the marker 3023 or 3023A and vice versa, except as otherwise noted. The markers 3023B may be located along the sidewall 3014 of the body 3002. There may be one or more markers 3023B located along an inner surface 3018 of the sidewall 3014.

As shown, two markers 3023B are visible on either side of the interior of the foam body 3002. The markers 3023B are attached through the foam and around the frame 3040. The marker 3023B may be attached, for example sutured, around a proximal face 3060 member of the frame 3040, such as one of the struts 3061. The marker 3023B may be attached to the frame 3040 just proximally of one of the proximal apexes 3084 of the frame 3040, for example at an outer curved portion 3066 of the strut 3061. There may be only one marker 3023B, or two, three, four or more markers 3023B. There may be one of the markers 3023B for each strut 3061. The markers 3023B may be used additionally to connect the frame 3040 with the foam body 3002. The markers 3023B may be sutures as described herein.

The one or more markers 3023A and/or 3023B at or near the proximal end of the device 3000 provide various desirable features. For instance, the marker 3023A at the shoulder 3030 facilitates visualization of the device 3000 during and after implantation. The typically non-circular shape of the opening of the LAA (ostium) may compress the proximal end 3004 of the device and cause the proximal end 3004 to protrude slightly in the proximal direction. However, the shoulder 3030 may provide a location for the marker 3023A where linear bulging of the foam body 3002 in the proximal direction is reduced or prevented. Thus, the marker 3023A in that location can provide a more useful visualization of the positioning of the device 3000 and reduce complexity. For example, in some embodiments, the marker 3023A at the shoulder 3030 (e.g. on an inner surface as shown) may be particularly useful during delivery, allowing for delivery using fluoroscopy imaging only without the need for echo or other ultrasound imaging. The one or more markers 3023B may provide similar benefits.

As further shown in FIGS. 3D and 5D, the device 3000 may include an inner cover 3101. The inner cover 3101 may have the same or similar features and/or functionalities as the cover 3100 (described in further detail below, see section "Proximal Cover"), except as otherwise described. The inner cover 3101 may be a cover for the hub 3050 (see, e.g., FIGS. 4C and 7A-8C). The inner cover 3101 may be formed from expanded Polytetrafluoroethylene ("ePTFE"). The inner cover 3101 may be a separate portion of the same material as the proximal cover 3100.

The inner cover 3101 may be located between the foam body 3002 and the frame 3040. As shown, the inner cover 3101 is located between the inner surface 3012 of the foam body 3002 and a proximal end of the hub 3050 of the frame 3040. The inner cover 3101 may be circular or other shapes. The inner cover 3101 may have an area sufficient to provide a barrier in between the hub 3050 and the proximal end 3004 of the foam body 3002. In some embodiments, the inner cover 3101 may extend radially to an outer circumference of the hub 3050, or it may extend radially to the sidewall 3014 such as to an inner surface 3018 of the foam body 3002, or to any radial locations in between. The inner cover 3101 may have a diameter from about 4 mm to about 22 mm, from about 5 mm to about 15 mm, from about 6 mm to about 10 mm, about 8 mm, or 8 mm. The inner cover 3101 may be flat or generally flat. The inner cover 3101 may have a thickness from about 0.0001"-0.0020", from about 0.0002"-0.0010", about 0.0005", or 0.0005" thick. The inner cover 3101 may include one or more openings 3103 such as holes therethrough. The inner cover 3101 may include two holes 3103 to receive therethrough a tether 3240 (see, e.g., FIGS. 10A-11B). The two holes 3103 in the cover 3101 may align the tether 3240, such as a suture, that extends distally into the hub 3050 through one hole 3103 in the inner cover 3101 and exits proximally back out of the hub 3050 through the other hole 3103 of the inner cover 3101.

The inner cover 3101 may prevent the hub 3050 and/or other features of the frame 3040 from directly contacting the foam material. The cover 3101 may protect the integrity of the foam body 3002 from stresses that may be imparted by the hub 3050 on the foam material. This protection may be desirable for example during loading, deployment, retrieval, re-deployment, etc. of the device 3000. The inner cover 3101 may prevent or reduce damage to the foam body 3002 from the hub 3050.

The foam body 3002 may be attached to various features of the device 3000. The body 3002 may be attached to the frame 3040 at numerous points, including for example the center of the proximal end of the frame 3040, as further described herein. Attachment can be done using suture, such as polypropylene monofilament suture, although other methods known in the art such as adhesive bonding could be utilized. The proximal row of proximal anchors 3090 may be individually attached to (e.g. inserted through) the foam body 3002 to prevent relative movement between the foam body 3002 and the frame 3040. In other embodiments, the foam body 3002 could be formed around the endoskeleton so that the metallic frame is within the foam body 3002, eliminating the need for a secondary attachment step. Attachment of the body 3002 to the frame 3040 promotes retrieval without damage to the foam body 3002, among other advantages. The attachment also ensures that a bumper 3026, further described herein, extends beyond the frame 3040 at all times, including during initial exposure of the device 3000 upon proximal retraction of the delivery sheath.

As shown in FIG. 5D, the device 3000 may include one or more attachments 3001. The attachments 3001 may connect the frame 3040 with the foam body 3002. The attachments 3001 may be sutures. Other suitable attachment structures may be used, including staples, ties, wires, components of the frame 3040, other mechanical attachments, adhesives, other suitable means, or combinations thereof. The attachments 3001 may extend around the frame 3040 and through the foam body 3002, for example through the sidewall 3014.

As shown, four attachments 3001 are visible in FIG. 5D. There are two proximal attachments 3001 and two distal attachments 3001 visible. The proximal attachments 3001 are each located at the base of a respective proximal anchor 3090. The distal attachments 3001 are each located at the base of a respective distal anchor 3094. There may be one, two, three, four, five, six, seven, eight, or more attachments 3001. There may be twenty attachments 3001. There may be one of the attachments 3001 for each anchor 3090, 3094 of the device 3000. The attachments 3001 may each be located at a proximal apex 3084 or at a distal apex 3088 of the frame 3040, as further described herein, for example with respect to FIG. 7A. For example, the attachments 3001 may be wrapped around one or more of the struts 3082, 3086, as further described herein. The attachments 3001 may locally compress the foam body 3002 at and/or around the location of attachment, as further described herein, for example with respect to FIG. 12C. The attachment 3001, such as a suture, may extend from within the cavity 3028, through the foam body 3002, exit the foam body 3002 and extend along the outer surface 3016 of the foam body 3002, extend back into and through the foam body 3002 into the cavity 3028, and be tied or otherwise connected together around the frame 3040. In some embodiments a similar routing of the attachments 3001 may be used with the attachment 3001 tied or otherwise connected together around and outside the foam body 3002. In some embodiments the attachments 3001 may also extend through the cover 3300, or other covers as described herein. The attachments 3001 may extend through the material of the cover 3300. The attachments 3001 may extend through openings in the cover 3300, such as the side openings 3324, or windows 3177 (see, e.g., FIGS. 6B-6E). As shown, the proximal attachments 3001 may extend through the foam body 3002 and through openings in the cover 3300, and the distal attachments 3001 may not extend through the cover 3300 but only through the foam body 3002.

The foam body 3002 may include a coating. In some embodiments, there may not be a coating. In embodiments with a coating, the coating is applied to the interconnected reticulations of the foam material. The body 3002 may be coated with pure polytetrafluoroethylene (PTFE). The PTFE coating minimizes the thrombogenicity of the LA surface, while also reducing the friction of the foam body 3002 against the delivery system to facilitate ease of deployment and retrieval. The body 3002 may be coated with conformable, vacuum deposited, pure PTFE. In addition or alternatively, the body 3002 may be coated with a coating other than PTFE. The coating, whether PTFE or otherwise, may be about 0.5 µm thick, and covers at least a portion of the surface of the interconnected reticulations of the foam without occluding the pores. The coating may be applied to some or all of the foam body 3002. The coating may be applied to some or all of the outer surfaces of the foam body 3002.

In some embodiments, the thickness of the coating is from about 0.1 µm to about 1 µm, from about 0.2 µm to about 0.9 µm, from about 0.3 µm to about 0.8 µm, from about 0.4 µm to about 0.7 µm, about 0.4 µm to about 0.6 µm, or about 0.5 µm thick. In some embodiments, greater or smaller thicknesses of the coating may be applied. The coating has a uniform or substantially uniform thickness. In some embodiments, the coating may have a non-uniform thickness. For example, the portion of the body 3002 facing the LA when implanted, such as the proximal face 3008 and/or shoulder 3030, may have a thicker coating relative to a coating along the sidewall 3014 of the body 3002. In some embodiments, the outer surface 3010 of the proximal face 3008 has a PTFE coating and the proximal face 3008 also has a ePTFE cover 3100.

The coating is applied using a vapor deposition process. In some embodiments, the coating is applied through coating, vapor deposition, plasma deposition, grafting, other suitable processes, or combinations thereof. The coating is applied to the outer surfaces 3010, 3032 and 3016 of, respectively, the proximal face 3008, the shoulder 3030 and the sidewall 3014. In some embodiments the coating is applied to the outer surfaces 3010, 3032 and only partially on the outer surface 3016. In some embodiments the coating is applied to outer and inner surfaces of the body 3002.

In some embodiments, other biocompatible, thromboresistant and/or lubricious materials could be applied to the surface(s) of the foam body 3002 and/or the cover 3100. These materials may encourage tissue ingrowth. Such materials may include, for example, heparin, albumin, collage, polyethylene oxide (PEO), hydrogels, hyaluronic acid, materials that release nitric oxide, oxygen, nitrogen, amines, bioabsorbable polymers, and other biomaterials, pharmacologic agents, and surface modification materials. Additionally, the surface(s) of the body 3002 could be roughened, textured, or otherwise modified or coated to promote healing or to make it more echogenic.

2. Proximal Cover

The device 3000 may include a cover 3100, which may be an ePTFE cover as further described. Other embodiments for this outer cover 3100 are described herein, for example the cover 3101, 3300, 3150, 3151, etc. The various embodiments of the cover may have the same or similar features and/or functionalities as each other, except as otherwise noted. The cover 3100 may have a series of openings. In some embodiments, the cover 3100 may be solid and not have any openings. In some embodiments, the cover 3100 may only have openings to receive anchors and/or a tether therethrough, as further described herein. In some embodiments, the device 3000 may include an inner cover such as an inner cover 3101, as shown and described with respect to FIG. 3D.

The outer cover 3100 is a generally flat material applied over and covering at least a portion of the body 3002. The cover 3100 is on the proximal end 3004 of the device 3000. The cover 3100 covers the proximal face 3008 of the body 3002 and at least part of the sidewall 3014. The cover 3100 covers a proximal portion of the sidewall 3014. The cover 3100 has a proximal surface 3102 that at least partially faces the LA when implanted. The cover 3100 has an outer edge 3104 forming outer vertices 3106 (for clarity, only some of the outer edges 3104 and outer vertices 3106 are labelled in the figures). In some embodiments, the cover 3100 may cover only the proximal face 3008 or portions thereof. In some embodiments, the cover 3100 may extend over more of the sidewall 3014, such as the middle or distal portion thereof, or the entire sidewall 3014.

The cover 3100 may have a thickness measured perpendicularly from the proximal surface 3102 to an opposite distal surface of the cover 3100 that faces the body 3002. The cover 3100 may have a thickness of 0.001" (inches). In some embodiments, the cover 3100 may have a thickness from about 0.00025" to about 0.005", from about 0.0003" to about 0.004", from about 0.0004" to about 0.003", from about 0.0006" to about 0.002", from about 0.0008" to about 0.0015", or about 0.001". In some embodiments, the cover 3100 may have a thickness of 0.0005". In some embodiments, the cover 3100 may have a thickness from about 0.0002" to about 0.0008", from about 0.0003" to about 0.0007", from about 0.0004" to about 0.0006", or about 0.0005".

The cover 3100 may be attached to the frame 3040 through the foam body 3002. The cover 3100 may in addition or alternatively be attached to the body 3002. The cover 3100 may be attached at least two or four or six or more of the outer vertices 3106. The cover 3100 may be attached to the frame 3040 and/or body 3002 at various locations, including at the outer vertices 3106, through the proximal surface 3100, at the proximal face 3008 of the body 3002, other locations, or combinations thereof. The cover 3100 is attached using mechanical attachments, such as sutures. In some embodiments, polypropylene 6-0 sutures are used throughout the device to attach the foam body 3002, proximal cover 3100, and RO markers 3023 to the foam body 3002 and/or frame 3040. In some embodiments, the cover 3100 is attached to the frame 3040 via standard braided or monofilament suture material, such as polypropylene, ePTFE, or polyester. In some embodiments, a polypropylene monofilament is utilized. Proximal anchors 3090 of the frame 3040 (further described herein) may extend through the outer vertices 3106 of the cover 3100. Such penetrating anchors 3090 may further secure the cover 3100 in place relative to the body 3002. In some embodiments, the cover 3100 may be attached to the various parts of the device 3000 with mechanical attachments, fasteners, adhesives, chemical bonds, other suitable techniques, or combinations thereof.

As shown, the cover 3100 is formed from expanded Polytetrafluoroethylene ("ePTFE"). An ePTFE cover 3100 provides many advantages. For example, the ePTFE cover 3100 may enhance the ability to recapture the device 3000 in vivo by distributing the proximal retraction forces applied by the catheter. The cover 3100 may be an ePTFE material approximately 0.001" thick, with the appropriate porosity to encourage healing and minimize thrombus formation, similar to the underlying PTFE coated foam.

An ePTFE cover 3100 may assist in recapture of the implant into the access sheath while providing a smooth, thromboresistant surface which encourages tissue coverage and integration. The ePTFE may cover the entire proximal face and partially covers the sides, as shown in FIG. 3C. The ePTFE cover 3100 is fabricated from a previously laminated sheet comprised of two or more sheets of oriented material, offset to form a biaxially orientated material. Alternatively, one could use a tube, preferably biaxially oriented, that is then cut to form a sheet. The thickness of the final construct can be from 0.0005"-0.005" but is preferably about 0.001".

Figure 6A:
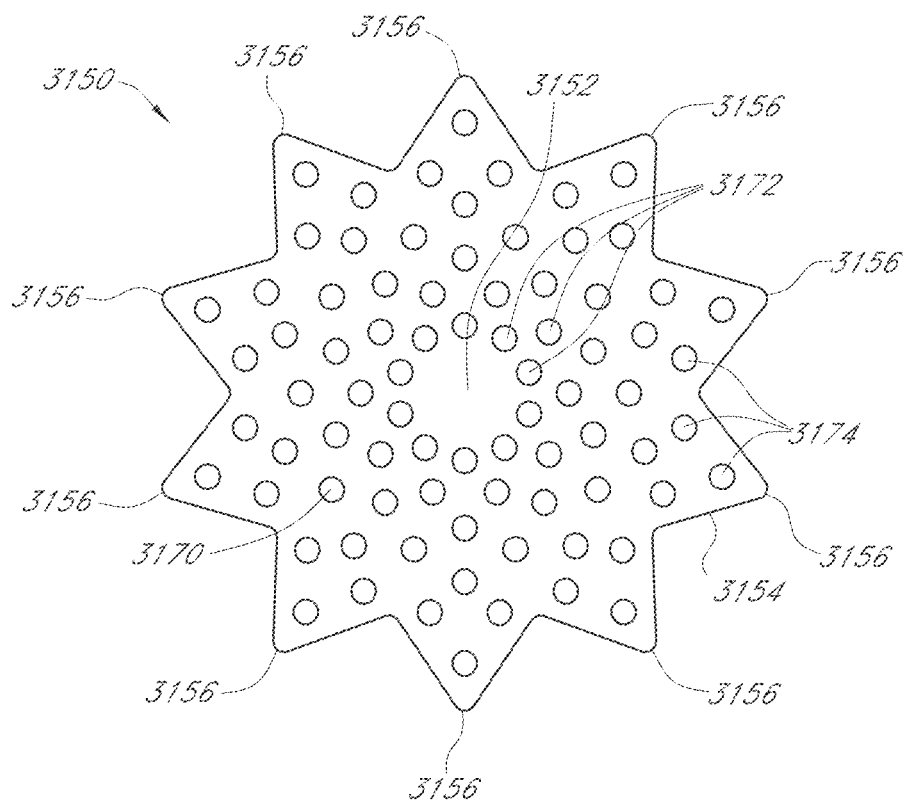
FIG. 6A is a top view of an embodiment of a proximal cover shown in a flat configuration that may be used with the various LAA occlusion devices described herein.
Figure 6B:
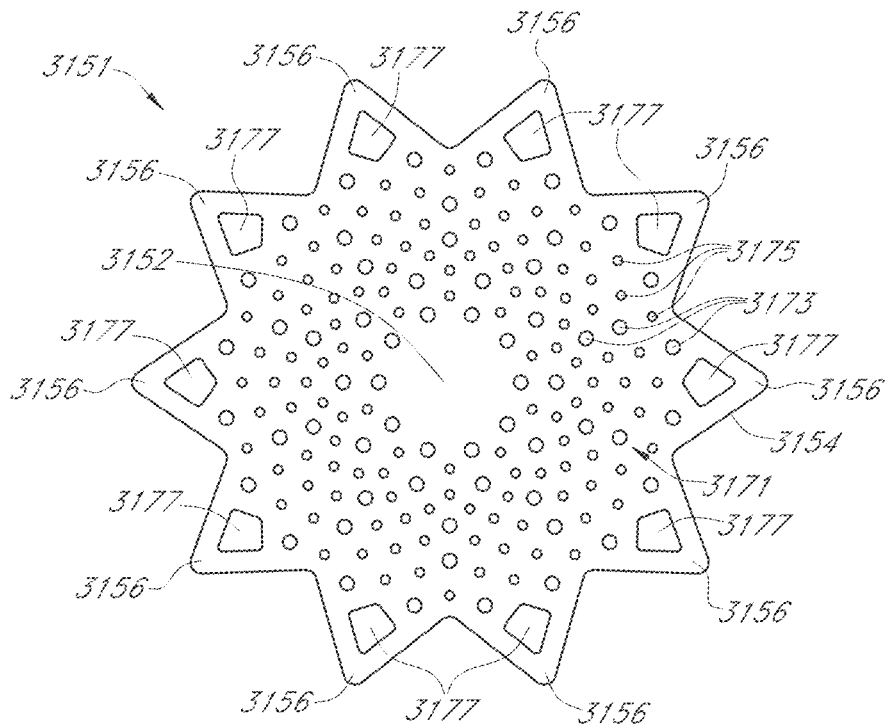
FIGS. 6B-6C are top views of another embodiment of a proximal cover shown, respectively, in a flat configuration and assembled with an LAA occlusion device.

In some embodiments, the cover 3100 is fabricated from other thromboresistant, high strength, biocompatible materials, such as knitted or woven polyester fabrics, polypropylene, polyethylene, non-woven vascular scaffolds, porous films, or bioabsorbable scaffolds such as polylactic acid, polyglycolic acid, and co-polymers. The shape of the cover prior to attachment with the device 3000, such as shown in FIGS. 6A and 6B, minimizes wrinkling and provides a smooth surface following attachment to the implant. This shape may be a star shape, an outer pointed shape, or other shapes.

The cover 3100 may be perforated with a series of openings 3120 (for clarity, only some of the openings 3120 are labelled in the figures). The openings 3120 are perforations or holes formed in the cover 3100 via laser or mechanical cutting. The openings 3120 include proximal openings 3122 and side openings 3124 (for clarity, only some of the proximal openings 3122 and side openings 3124 are labelled in the figures). When the cover 3100 is assembled with the body 3002, the proximal openings 3122 are located over the proximal face 3008 and/or shoulder 3030, and the side openings 3124 are located over the sidewall 3014. In some embodiments, the cover 3100 includes forty proximal openings 3122. In some embodiments, the cover 3100 includes forty side openings 3124. The number of openings 3120 located over the proximal face 3008 and/or shoulder 3030 when assembled with the body 3002 may range from ten to eighty, from twenty to seventy, from thirty to sixty, from thirty five to fifty, or forty openings 3120. The number of openings 3120 located over the sidewall 3014 may range from ten to eighty, from twenty to seventy, from thirty to sixty, from thirty five to fifty, or forty openings 3120.

The openings 3120 may have a variety of sizes. The openings 3120 are 0.070" in width, e.g. minor axis, or diameter for circular openings. The openings 3120 may have a width from about 0.010" to about 0.200", from about 0.020" to about 0.150", from about 0.030" to about 0.110", from about 0.040" to about 0.100", from about 0.050" to about 0.090", from about 0.060" to about 0.080", or about 0.070". In some embodiments, the width may be less than 0.010" or greater than 0.200", such as 0.25", 0.5" or greater. These widths may apply to circular as well as non-circular shaped openings 3120.

In some embodiments, the openings 3120 may be various shapes. The openings 3120 may be elongated slots. The openings 3120 may extend radially along the cover 3100 from or near a center portion of the proximal surface 3102 toward and/or to the outer edge 3104. The openings 3120 may be annular openings extending circumferentially along the cover 3100 and having varying radial positions. The openings 3120 may be of uniform size and shape. Some of the openings 3120 may have varied sizes and/or shapes with respect to other of the openings 3120. The openings 3120 may have various distributions or concentrations about the cover 3100. For example, the openings 3120 may be more densely located in various areas, such as along the proximal surface 3102 that faces the LA, along the shoulder 3030, etc.

The openings 3120 enable blood to flow through the device 3000. The openings 3120 may allow blood to adequately flow through the device 3000 and thereby mitigate the risk of occlusion in the bloodstream should the device 3000 embolize within the vasculature system. In some embodiments, should the device 3000 embolize, it may act as a stationary filter at low pressures but may pass through the bloodstream at higher pressures. In some embodiments, the device 3000 allows for about two to about fourteen liters, from about four to about twelve liters, from about six to about ten liters, or from about eight liters per minute of blood to pass at <30 mmHg pressure drop to prevent shock in the event of a device embolization. In some embodiments, there are forty circular openings 3120 each having a diameter of 0.070", and allowing for approximately eight liters per minute of blood to pass at <30 mmHg pressure drop. In some embodiments, the proximal end of the device 3000 may be a foam layer such as the foam proximal face 3008 or a membrane such as the cover 3100 or both, enclosing the cavity 3028 defined within the tubular side wall 3014 of the body 3002.

In one implementation, having both the foam proximal face 3008 and the cover 3100, the foam body 3002 has the open cell structure further discussed herein that can permit the passage of blood but block escape of embolic debris. The cover 3100 may be occlusive to blood flow, and is present to provide structural integrity and reduced friction for retracting the expanded body 3002 back into the deployment catheter. In one implementation, the cover 3100 is ePTFE in a form that is substantially occlusive to blood flow, as described. In this embodiment, the cover 3100 is therefore provided with a plurality of perfusion windows or openings 3120, so that blood can pass through the open cell foam and cover 3100 but the device 3000 still benefits from the other properties of the cover 3100.

In some embodiments, the device 3000 may allow for a particular flow rate of water at specified conditions, to test the perfusion performance of the device 3000. The device 3000 may have the foam body 3002 and cover 3100 configured to allow for a flow rate of water axially through the device 3000 of at least 2.8 liters per minute. The water may be at sixty-eight degrees Fahrenheit (F) or about sixty-eight degrees F. and an upstream pressure of twenty-eight millimeters of Mercury (mmHg) or about twenty-eight mmHg. In some embodiments, the device 3000 may be configured to allow for flow rates under such conditions from about 2.8 liters to about 19.6 liters, from 4.2 liters to about 5.6 liters, from about 4.76 liters to about 5.6 liters, from about 5.6 liters to about 16.8 liters, from about 8.4 liters to about 14 liters, more than 2.8 liters, more than 5.6 liters, more than 8.4 liters, or more than 11.2 liters of water per minute.

In some embodiments, the foam and cover are configured to allow for a flow rate of water axially through the device of between 4.2 liters per minute and 5.6 liters per minute (for example, in embodiment of a 27 mm diameter implant), with the water at about sixty-eight degrees Fahrenheit (F) and an upstream pressure of about twenty-eight millimeters of Mercury (mmHg). In some embodiments, the foam and cover are configured to allow for a flow rate of water axially through the device of between 4.76 liters per minute and 5.6 liters per minute (for example, in embodiment of a 35 mm diameter implant), with the water at about sixty-eight degrees Fahrenheit (F) and an upstream pressure of about twenty-eight millimeters of Mercury (mmHg).

The particular flow rate may depend on the porosity of the foam body 3002 and the open area of the cover 3100. The particular flow rate may depend on the inner cover 3101 features as well. The cover 3100 may have particular percentages of the cover area open with the series of openings, as further described herein, to attain a particular desired flow rate. The flow rate of water at the specified conditions may be used to extrapolate or otherwise calculate the corresponding expected flow rate of blood in the body through the device 3000 should it embolize, as described herein. In some embodiments, the device 3000 may be configured to allow for a flow rate of blood axially through the device 3000 of at least 1 liter per minute (for example, in embodiment of a 27 mm diameter implant at room temperature with an upstream pressure of about 15 inches of water head). The device 3000 may allow for a cardiac output from about 4.2 to 8 liters per minute. The average body surface area is 1.6 square meters for females and 1.9 square meters for males. The device 3000 may allow for a cardiac index from about 2.2 to 5 or from about 2.6 to 4.2 liters per minute per square meter. The device 3000 may have these and other flow rate capabilities either aligned or approximately aligned with the direction of flow of the fluid, or off-axis where the device 3000 is angled with respect to the direction of flow of the fluid (a flow axis), as further discussed herein for example in the section "Off-Axis Delivery and Deployment."

FIGS. 5A-5C depict an embodiment of the LAA occlusion device 3000 having another embodiment of a cover 3300. The device 3000 includes the foam body 3002 and the frame 3040, and features thereof, as described herein, and additionally includes the cover 3300. The cover 3300 may have the same or similar features and/or functionalities as the cover 3100, and vice versa. The cover 3300 is on the proximal end 3004 of the device 3000. The cover 3300 covers the proximal face 3008 of the body 3002 and a proximal part of the sidewall 3014. The cover 3300 has a proximal surface 3302. The cover 3300 has an outer edge 3304 forming a plurality of at least two or four or six or eight or ten or more outer vertices 3306 (for clarity, only some of the outer vertices 3306 are labelled in the figures). The cover 3300 is attached to the body 3002 at the outer vertices 3306. The proximal anchors 3090 extend through side openings 3324 in the outer vertices 3106 of the cover 3100.

The cover 3300 includes a series of openings 3320. The openings 3320 include proximal openings 3322, shoulder openings 3323, and the side openings 3324. The proximal openings 3322 are located over the proximal end 3004 of the body 3002. The shoulder openings 3323 are located over the shoulder 3030, e.g. a bevel, of the body 3002. The side openings 3324 are located over a proximal portion of the sidewall 3014 of the body 3002. The proximal anchors 3090 may extend through the side openings 3324 that are located in the outer vertices 3106. The openings 3320 may have the same or similar features and/or functionalities as the openings 3120, and vice versa. In some embodiments, the proximal anchors 3090 may extend through the cover 3300 material at or near the outer vertices 3106.

FIG. 6A shows another embodiment of a cover 3150 that may be used with the device 3000. The cover 3150 may have the same or similar features and/or functionalities as the cover 3100 and/or cover 3300, and vice versa. The cover 3150 may be used to cover the proximal face 3008 of the body 3002 and part of the sidewall 3014. The cover 3150 has a proximal surface 3152. The cover 3150 has an outer edge 3154 forming outer vertices 3156. The cover 3150 may be attached to the body 3002 at the outer vertices 3156. The proximal anchors 3090 may extend through the outer vertices 3156 of the cover 3100. The cover 3150 includes a series of openings 3170. The openings 3170 include proximal openings 3172 and side openings 3174 (for clarity, only some of the openings 3170, 3172, 3174 are labelled in the figures). When the cover 3150 is assembled with the body 3002, the proximal openings 3172 are located over the proximal end 3004 and the side openings 3174 are located over the sidewall 3014. As shown, the openings 3174 may be substantially uniformly located along the cover 3150 except for a center region of the proximal surface 3152.

Figure 6C:
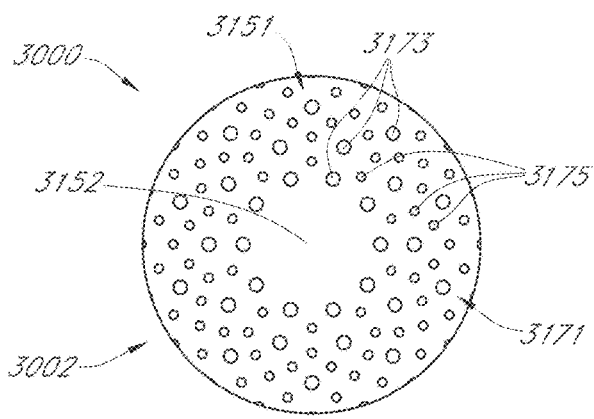

FIG. 6B is a top view of another embodiment of a proximal cover 3151 that may be used with the various LAA occlusion devices described herein. FIG. 6C is a top view showing the cover 3151 assembled with the device 3000. The cover 3151 may have the same or similar features and/or functionalities as other covers described herein, such as the cover 3100 and/or cover 3300, and vice versa, except as otherwise noted. For example, the cover 3151 may include the proximal surface 3152 and outer edge 3154 forming outer vertices 3156.

The cover 3151 further includes another embodiment of a series of openings 3171. The openings 3171 include smaller openings 3175 and larger openings 3173. The openings 3175, 3173 may have the same or similar features and/or functionalities as other cover openings described herein, such as the openings 3120, 3122, 3124, 3320, 3322, 3324, 3170, 3172 and/or 3174, and vice versa. The smaller openings 3175 may be relatively smaller, in width and/or area, than the larger openings 3173. There may be openings with widths or areas smaller than that of the smaller openings 3175, larger than that of the larger openings 3173, or anywhere in between. As shown, the openings 3173, 3175 may be generally uniformly distributed about the proximal surface 3152 of the cover 3151. The openings 3173, 3175 may be circumferentially evenly spaced or approximately evenly spaced about the cover 3151.

There may be a variety of different quantities of each of the openings 3173, 3175. There may be a total of ten, twenty, thirty, forty, fifty, sixty, seventy, eighty, ninety, one hundred, one hundred fifty, two hundred, three hundred, four hundred, or more openings of the series of openings 3171, or any lesser, greater or in between number of openings. The series of openings 3171 may be holes as shown. They may have circular shapes. They may have other shapes, including non-circular, segmented, other shapes, or combinations thereof. The openings 3171 may all have the same general shape or different shapes. In some embodiments, there may not be any holes in the cover 3151.

When the cover 3151 is assembled with the foam body 3002, the large and small openings 3173, 3175 may be located over the proximal end 3004 and/or the sidewall 3014 of the foam body 3002. When assembled with the foam body 3002, on the proximal-facing portion of the cover 3151, there may be a collective total of one hundred forty or about one hundred forty openings 3173, 3175. On this proximal-facing portion of the cover 3151, there may be a collective total from about ten to about three-hundred, from about fifty to about two hundred fifteen, from about one hundred ten to about one hundred seventy, from about one hundred twenty to about one hundred sixty, from about one hundred thirty to about one hundred fifty, or from about one hundred thirty-five to about one hundred forty-five openings 3173, 3175. On this proximal-facing portion of the cover 3151, there may be from about thirty to about fifty, from about thirty-five to about forty-five, about forty, or forty of the larger openings 3173. On this proximal-facing portion of the cover 3151, there may be from about sixty to about one hundred forty, from about eighty to about one hundred twenty, from about ninety to about one hundred ten, about one hundred, or one hundred of the smaller openings 3175.

When assembled with the foam body 3002, on the portion of the cover 3151 located over and/or near the shoulder 3030, such as over the outer surface 3032 of the foam body 3002 (see, e.g., FIG. 4B), there may be from about five to about eighty, from about ten to about forty, from about fifteen to about thirty, about twenty, or twenty of the smaller openings 3175. In some embodiments, at this same portion of the cover 3151, there may be from about five to about eighty, from about ten to about forty, from about fifteen to about thirty, about twenty, or twenty of the larger openings 3173.

When assembled with the foam body 3002, on the portion of the cover 3151 located over and/or near the sidewall 3014, such as over the outer surface 3016 of the foam body 3002 (see, e.g., FIG. 4B), there may be from about five to about eighty, from about ten to about forty, from about fifteen to about thirty, about twenty, or twenty of the larger openings 3173. In some embodiments, at this same portion of the cover 3151, there may be from about five to about eighty, from about ten to about forty, from about fifteen to about thirty, about twenty, or twenty of the smaller openings 3175.

The larger and smaller openings 3173, 3175 may have a variety of different sizes, for example as described herein with respect to the openings 3122. In some embodiments, the openings 3173, 3175 may have diameters ranging from about 0.025 inches to about 0.040 inches. In some embodiments, the larger openings 3173 may be 0.040 inches or about 0.040 inches in diameter. The larger openings 3173 may be from about 0.030 inches to about 0.050 inches, or from about 0.035 inches to about 0.045 inches, in diameter. These values may also refer to the widths, for example maximum widths, of non-circular larger openings 3173. In some embodiments, the smaller openings 3175 may be 0.025 inches or about 0.025 inches, in diameter. The smaller openings 3175 be from about 0.015 inches to about 0.035 inches, or from about 0.020 inches to about 0.030 inches, in diameter. These values may also refer to the widths, for example maximum widths, of non-circular smaller openings 3175.

The series of openings 3171 may be configured to provide a desired amount of open area through the cover 3151. This open area refers to the total area of certain openings in the cover 3151. The cover 3151 may be covering a proximal face 3008 at the proximal end 3004 of the foam body 3002. The open area may refer to openings through the portion of the cover that is over the proximal face 3008 of the foam body 3002 when assembled with the foam body 3002. The series of openings in the various covers described herein may collectively provide the open area. For example, the series of openings 3171 in the cover 3151 over the proximal face of the foam may collectively provide an open area. This is the sum of the area of the openings in the cover 3151 over the proximal face. As further example, the open area may be the sum of the proximal openings 3122 of the cover 3100. As further example, the open area may be the sum of the proximal openings 3322 of the cover 3300.

The open area may be at least five percent of the area of the proximal face 3008 of the foam body 3002. The open area may be at least six, at least seven, at least eight, at least nine, at least ten, at least eleven, at least twelve, at least thirteen, at least fourteen percent, at least fifteen, at least sixteen, at least seventeen, at least eighteen, at least nineteen, at least twenty, at least twenty-five, at least thirty, at least forty, or at least fifty percent, of the area of the proximal face 3008. The open area may be from about one to about fifty percent, from about five to about twenty percent, from about eight to about fifteen percent, from about ten to about twelve percent, or about eleven percent, of the area of the proximal face 3008. The "area" of the proximal face 3008 is understood here to refer to an area equal to $Pi \times R^2$, where R is the radius of the proximal face 3008 and extends perpendicularly from the longitudinal axis of the device 3000. Further, "R" may be measured to the inner boundary of the shoulder 3030, to the outer boundary of the shoulder 3030, or to the outer surface 3016 of the sidewall 3014. Further, as mentioned, some embodiments may not include a cover at all.

The cover 3151 may include one or more windows 3177. As shown, there may be ten windows 3177. There may be one window 3177 for each proximal anchor 3090. There may be four, six, eight, twelve, fourteen or more windows 3177, or any lesser or in between number. The windows 3177 may be openings in the cover 3151. The windows 3177 may be located at or near the outer edge 3154 of the cover 3151. The windows 3177 may be located along portions of the outer edge 3154, for example at or near the outer vertices 3156. The windows 3177 may have a shape conforming to the shape of the cover 3151 at the respective portions of the outer edge 3154. As shown, the window 3177 may be diamond or generally diamond shaped. The window 3177 may be square, rectangular, triangular, rounded, circular, segmented, flattened diamond, other polygonal shapes, other shapes, or combinations thereof. The cover 3150 may be attached to the body 3002 at the outer vertices windows 3177. The windows 3177 may have the same or similar feature and/or functionalities as the side openings 3324, described and shown in FIG. 5B. The proximal anchors 3090 may extend through the windows 3177 of the cover 3151 to retain the cover 3151 on the device 3000.

Figure 6D:
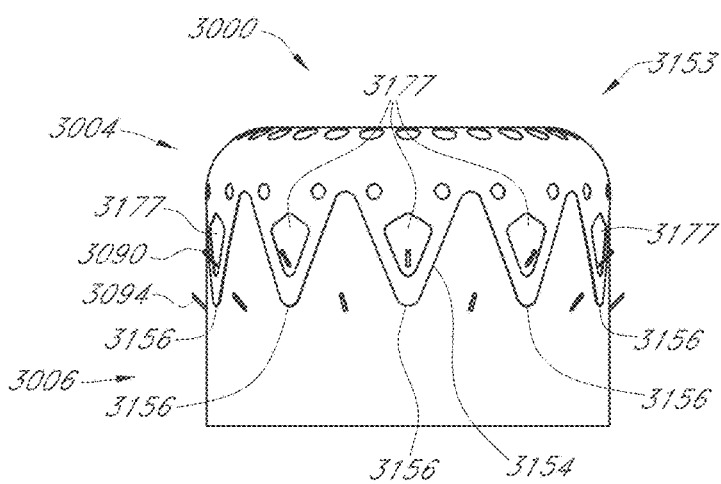
FIG. 6D-6E are side and perspective views, respectively, of another embodiment of a proximal cover shown assembled with an LAA occlusion device.
Figure 6E:
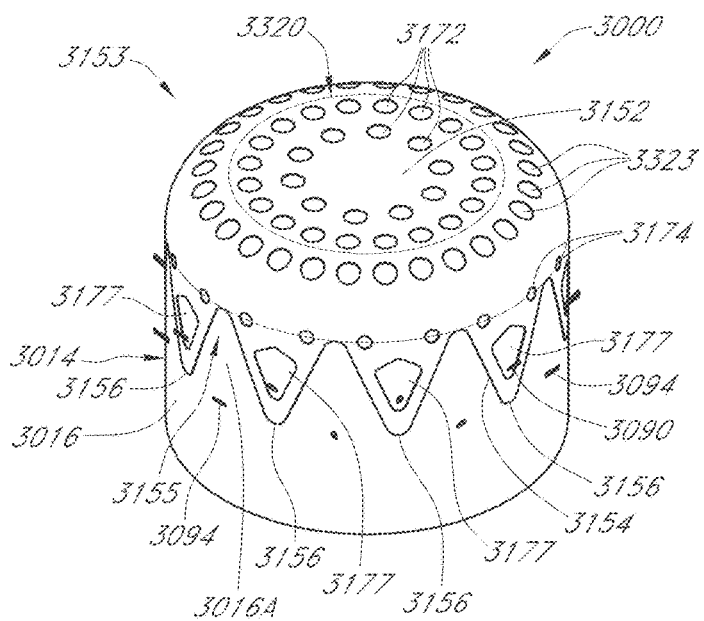

FIG. 6D-6E are side and perspective views, respectively, of another embodiment of a proximal cover 3153 shown assembled with the device 3000, that may be used with the various LAA occlusion devices described herein. The cover 3153 may have the same or similar features and/or functionalities as other covers described herein, such as the cover 3100, 3151, and/or cover 3300, and vice versa, except as otherwise noted. For example, the cover 3151 may include the proximal surface 3152, outer edge 3154 forming outer vertices 3156, and windows 3177.

The device 3000 with cover 3151 may have proximal anchors 3090 extending through the windows 3177. The proximal anchor 3090 may extend through the opening of the respective window 3177. The proximal anchor 3090 may extend through a distal portion of the window 3177, for example to contribute to securing the cover 3153 on the device 3000. The proximal anchors 3090 may extend through the window 3177 at a distal edge or distal vertex of the window 3177. In some embodiments, the proximal anchor 3090 may extend through the cover 3151 material, for example through material adjacent (such as distal) to the window 3177. In some embodiments, the proximal anchor 3090 may extend through various other locations within, adjacent or near the window 3177. Some of the proximal anchors 3090 may extend through first locations and other of the proximal anchors 3090 may extend through second locations of the cover 3153 different from the first locations. For instance, one or more anchors 3090 may extend through a first region of the window 3177, one or more other anchors 3090 may extend through a second region of the window 3177, still one or more other anchors 3090 may extend through other regions, such as through the cover 3153 material, etc.

The cover 3153 may include proximal vertices 3155. The proximal vertices 3155 may be formed by the outer edge 3154. The proximal vertices 3155 may be indentations along the outer edge 3154 of the cover 3153, for example angled as shown or other shapes, configurations, etc. The proximal vertices 3155 may define a region 3016A of the outer surface 3016 of the sidewall 3014. The region 3016A may be partially enveloped by the outer edge 3154 of the cover 3153. The region 3016A may receive one or more of the distal anchors 3094 therethrough. The distal anchor 3094 may extend through a distal portion of the region 3016A, or in other locations within, adjacent, or near the region 3016A. In some embodiments, the distal anchor 3094 may not extend through or near the region 3016. There may be multiple such regions 3016A of the foam body 3002 defined circumferentially about the device 3000 by the cover 3153.

The cover 3153 may include the series of openings 3320, for example as described with respect to FIG. 5A. The series of openings 3320 may include the proximal openings 3172, the shoulder openings 3323, and/or the side openings 3174. The cover 3153 may include different patterns, sizes, distributions, etc. of the openings 3320, for example as shown and described with respect to FIGS. 6B-6C.

3. Compliant Frame

Figure 7A:
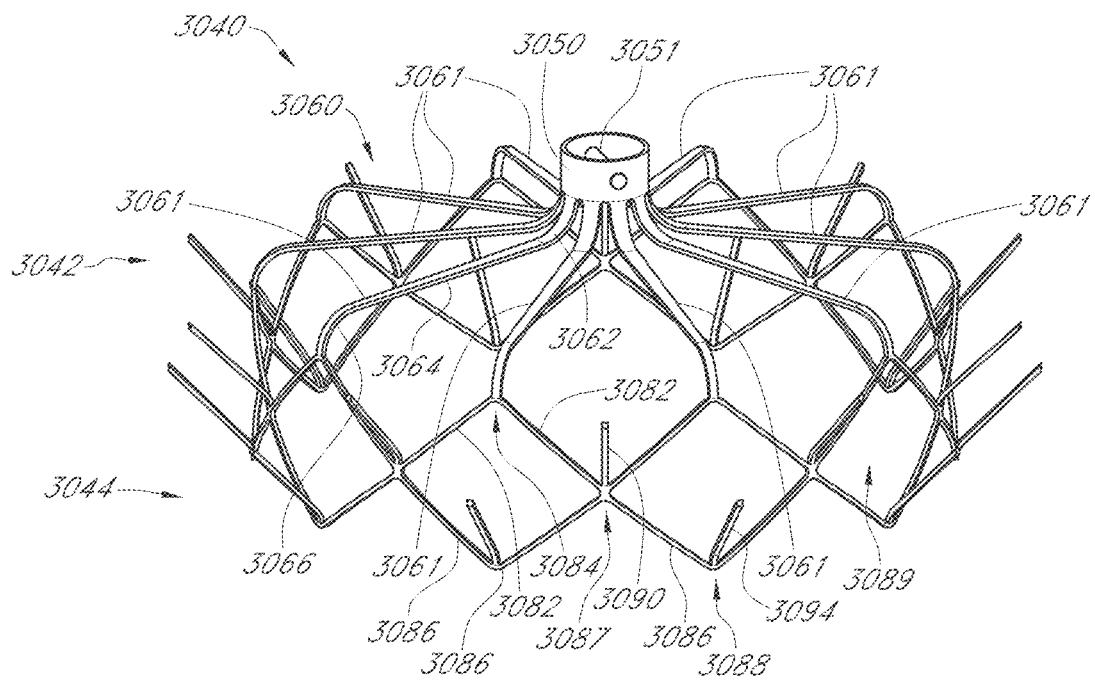
FIGS. 7A and 7B are side perspective and proximal perspective views, respectively, of the frame of FIGS. 3B and 4C shown in a deployed configuration.
Figure 7B:
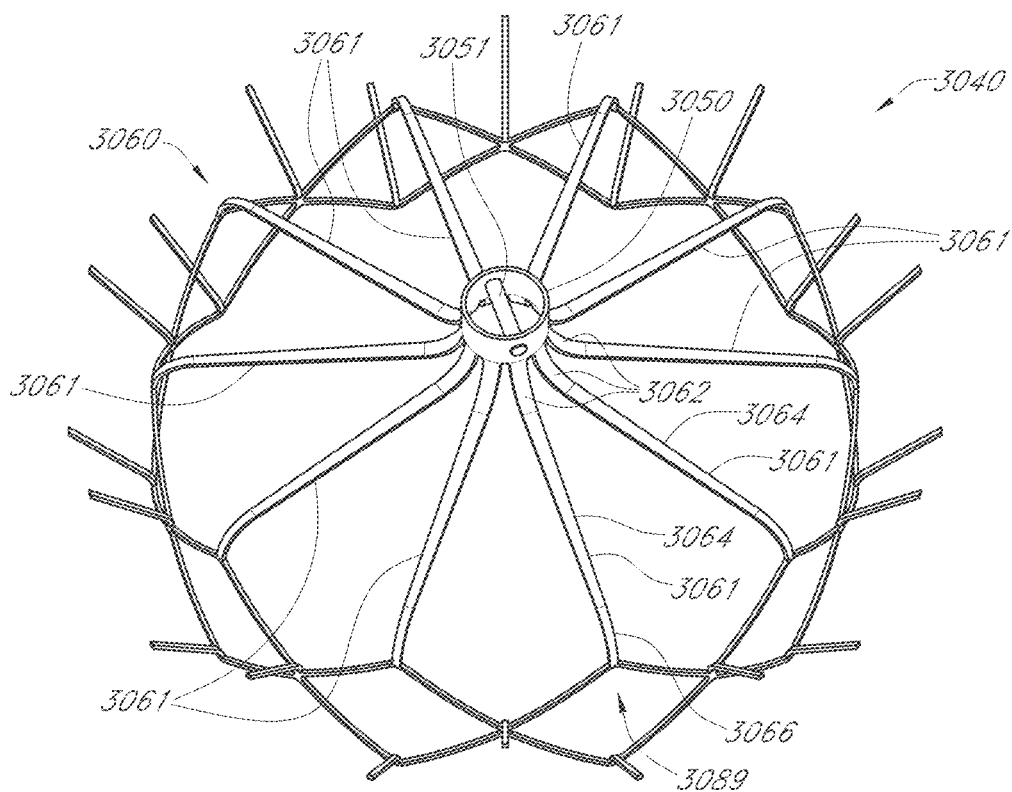

The expandable and compliant support or frame 3040 is shown, for example, in FIGS. 3B, 3D, 4C and 5C-E. Further, FIGS. 7A and 7B are side and proximal perspective views, respectively, of the frame 3040 shown in a deployed configuration and in isolation from the rest of the device 3000. The frame 3040 provides a compliant structure with anchors to facilitate delivery, anchoring, retrieval and to enable the foam body 3002 to compress against the LAA tissue to facilitate sealing, among other things, as further described. The frame 3040 is located inside the cavity 3028 formed by the foam body 3002. In some embodiments, the frame 3040 may be located partially or entirely inside one or more portions of the body 3002, e.g. within the proximal face 3008 and/or the sidewall 3014, as further described. For example, the frame 3040 may be partially located within the sidewall 3014 as shown in FIG. 5C.

The frame 3040 has a proximal end 3042 and an opposite distal end 3004. The frame 3040 may be tubular, e.g. cylindrical, in a free, unconstrained state. Thus the width of the proximal end 3042 may be the same or similar to the width of the distal end 3004 in the free, unconstrained state. In some embodiments, the frame 3040 or portions thereof may be conical or frustoconical, e.g. where in the free, unconstrained state the width of the proximal end 3042 is greater than the width of the distal end 3004 or vice versa.

At the proximal end 3042, the frame 3040 has a proximal hub 3050, shown as a cylindrical nipple. The hub 3050 is a rounded, structural end piece. The hub 3050 may be tubular, e.g. circular and having the cylindrical shape as shown, or may be rounded, non-circular, segmented, other shapes, or combinations thereof. The hub 3050 extends axially and may have a central lumen. The hub 3050 may be wider than it is long, or vice versa. The hub 3050 is hollow and has a sidewall defining a space therethrough, such as a longitudinal opening. In some embodiments, the hub 3050 may be partially hollow, solid, or other configurations. The hub 3050 facilitates delivery and retrieval of the device 3000, as further described. The hub 3050 may provide a central structural attachment, as further described herein. The hub 3050 may be located within the cavity 3028 at a proximal end thereof. In some embodiments, the hub 3050 may be located partially or entirely within the foam body 3002, e.g. within the proximal face 3008.

A pin 3051 is located within the hub 3050 (shown in FIGS. 7A and 7B). The pin 3051 is an elongated, rounded structural element extending laterally across the central lumen. "Lateral" here refers to a direction perpendicular or generally perpendicular to the longitudinal axis. The pin 3051 has a cylindrical shape. The pin 3051 provides a rounded outer surface configured to provide a smooth engagement surface with a tether, as further described. The pin 3051 provides a high strength connection with the frame 3040 to allow for pulling on the device 3000 with sufficient force to re-sheath the device 3000. The pin 3051 may be formed from Nitinol. The pin 3051 is secured across the width, e.g. diameter, of the proximal hub 3050. The pin 3050 may be secured at its two opposite ends with the sidewall of the hub. The pin 3051 is configured to be engaged by a tether 3240, which is wrapped around the pin 3051 in sliding engagement for temporary attachment to a delivery catheter, as further described. In some embodiments, the pin 3051 is assembled with a cap 3180, as further described herein, for example with respect to FIGS. 8A-8C.

The frame 3040 at the proximal end 3042 includes a proximal face 3060. The proximal face 3060 may be located within the cavity 3028 at a proximal end thereof. In some embodiments, the proximal face 3060 may be located partially or entirely within the foam body 3002, e.g. within the proximal face 3008 and/or sidewall 3014. The proximal face 3060 includes a series of recapture or reentry struts 3061. The struts 3061 are located at a proximal end of the cavity 3028. In some embodiments, the struts 3061 or portions thereof may be located partially or entirely within the foam body 3002, e.g. within the proximal face 3008 and/or sidewall 3014.

The struts 3061 are elongated structural members. The struts 3061 may have rectangular, circular or other shaped cross-sections. In some embodiments, the struts 3061 have a cross-section, e.g. rectangular, with a width that is greater than a thickness such that the struts 3061 are stiffer in one direction compared to another direction. This width may be in the lateral direction or a direction generally perpendicular to the longitudinal axis of the device 3000 when the device 3000 is in the expanded configuration, with the thickness perpendicular to the width. The struts 3061 may be less stiff in the direction of flexing or bending, for example to facilitate contraction and expansion of the device 3000 in the delivery and expanded configurations. The struts 3061 may be elongated pins. The struts 3061 may extend from the hub 3050, for example, and incline radially outwardly in the distal direction from the hub 3050. The struts 3061 may be attached inside, outside, and/or at the end of the sidewall of the hub 3050. The struts 3061 may be separate parts that are then attached to the hub 3050, for example welding, bonding, fastening, other suitable means, or combinations thereof. In some embodiments, some or all of the struts 3061 and the hub 3050 may be a single, continuous structure formed from the same raw material such as a laser cut hypotube. Some or all of the struts 3061 may be attached, e.g. with sutures as described herein, to the body 3002 and/or the cover 3100 at one or more attachment locations.

Each recapture strut 3061 may include an inner curved portion 3062 connected to a distal end of the hub 3050, a middle straight portion 3064, and/or an outer curved portion 3066 (for clarity, only some of the portions 3062, 3064, 3066 are labelled in the figures). In the deployed configuration, the inner curved portion 3062 extends from the hub 3050 primarily in a distal direction and then curves to face more outwardly radially. The middle straight portion 3064 extends from the inner curved portion 3062 primarily radially but also slightly distally. The outer curved portion 3066 extends from the middle straight portion 3064 primarily in the radial direction and then curves toward the distal direction. The portions may have different shapes in the delivery configuration inside a delivery catheter. In the delivery configuration, the portions may extend primarily distally. The portions may then take the deployed configuration as described upon deployment from the delivery catheter. In some embodiments, the struts 3061 may include fewer or more than the portions 3062, 3064, 3066.

The device 3000 may include ten of the proximal recapture struts 3061. Such configuration may accompany a device 3000 having a foam body 3002 with an outer diameter of 27 mm in the free, unconstrained state. Such configuration may accompany a device 3000 having a foam body 3002 with an outer diameter of 35 mm in the free, unconstrained state. In some embodiments, the device 3000 may have from about two to about thirty, from about four to about twenty, from about six to about eighteen, from about eight to about sixteen, from about ten to about fourteen, or other numbers of struts 3061. In some embodiments, the device 3000 has twelve of the proximal recapture struts 3061, for example for the 35 mm diameter device.

In the deployed configuration, each strut 3061 may extend radially outward and distally at an angle to the axis. This angle, measured relative to a portion of the axis that extends distally from the device 3000, may be from about 60° to about 89.9°, from about 65° to about 88.5°, from about 70° to about 85°, from about 72.5° to about 82.5°, from about 75° to about 80°, or other angular amounts. This angle may be much smaller when the device 3000 is in the delivery catheter. The struts 3061 may bend or flex when transitioning between, or when positioned in, the delivery and expanded configurations. The struts 3061 may bend or flex at the inner curved portion 3062, the middle straight portion 3064, and/or the outer curved portion 3066.

The proximal end 3042 of the frame 3040, such as the proximal face 3060, may therefore have a conical shape in the expanded configuration. The conical proximal face 3060 may facilitate with recapture of the device 3000 back into the delivery catheter. For example, the orientation of the struts 3061 inclining distally and radially outward from the hub 3050 in the expanded configuration provides an advantageous conical shape to the proximal face 3008 such that distal advance of the delivery sheath over the device 3000 will bias the struts 3061 inward and cause the device 3000 to stow back toward the delivery configuration and size for retrieval within the catheter.

The proximal face 3060 foreshortens considerably upon expansion of the device 3000 relative to the delivery configuration. "Foreshortening" here refers to the difference in axial length of the proximal face 3060 between the reduced delivery configuration and the expanded configuration (expanded either freely or as implanted). This length may be measured axially from the distal or proximal end of the hub 3050 to the distal ends of the outer curved portions 3066 of the recapture struts 3061. The proximal face 3060 may foreshorten by 50%, 60%, 70%, 80%, 90% or more. The proximal face 3060 has significantly more foreshortening upon expansion than the tubular body 3080, the latter of which may be referred to as the "working length" or "landing zone." The landing zone is further described with respect to the tubular body 3080 herein.

As shown, the struts 3061 are angularly spaced about the axis in even angular increments. That is, looking at the frame 3040 from the distal or proximal end, the angles between the struts may be equal. In some embodiment, the struts 3061 may not be evenly angularly spaced about the axis as described. The struts 3061 may or may not be symmetrically disposed about the axis or about a plane that includes the axis.

Figure 5E:
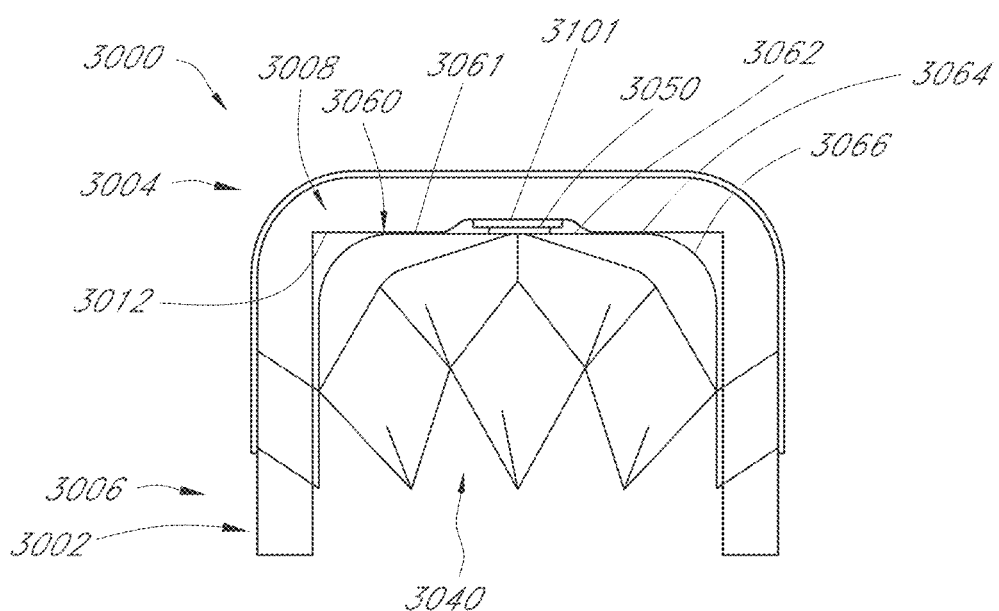

In some embodiments, portions of the frame 3040 may be at various distances from the proximal end of the foam body 3002, such as the proximal end wall having the proximal face 3008. As shown in FIG. 5D, there may be a gap of size Z in the axial direction between the proximal face 3060 of the frame 3040 and the inner surface 3012 of the proximal face 3008. The length of Z may be one, two, three, four, five, six, seven, eight, nine, ten, or more millimeters. The length of Z may vary depending on the radial distance at which it is measured. For instance, the length of Z may decrease, increase, or combinations thereof, as measured along the length of the strut 3061. In some embodiments, the length of Z may be zero at more or points along the length of the strut 3061. As shown in FIG. 5E, the proximal face 3060 or portions thereof may contact the proximal inner surface 3012 of the foam body 3002. The inner curved portion 3062, the straight portion 3064, and/or the outer curved portion 3066 may contact the proximal end wall such as the inner surface 3012 and/or other portions of the foam body 3002. The hub 3050 may compress the proximal face 3008 or proximal end wall of the foam body 3002 slightly in a proximal direction as shown. The proximal face 3008 may therefore have a smaller thickness in this compressed region as compared to other portions of the proximal face 3008, for example portions adjacent to this compressed portion. The hub 3050 may be located based on the axial location of connection of the anchors 3090, 3094 to the sidewall 3014, as described herein. In some embodiments, the hub 300 may not compress the foam body 3002 as shown. In some embodiments, the proximal face 3060 may extend radially outwardly as shown. For instance, the struts 3061, or portions thereof for instance the straight portions 3064, may extend radially outwardly perpendicularly or generally perpendicularly to the longitudinal axis of the device 3000. The proximal face 3060 may extend radially outwardly and incline in a distal direction, as described herein, or it may incline in a proximal direction. The device 3000 may have any of these features in the constrained, unconstrained and/or implanted configurations.

The frame 3040 includes a tubular body 3080. The body 3080 provides a mechanical base structure for the device 3000, as further described. The tubular body 3080 is attached to a distal end of the proximal face 3060 of the frame 3040. The tubular body 3080 extends to the distal end 3044 of the frame 3040. The tubular body 3080 is attached at a proximal end to the outer curved portions 3066 of the recapture struts 3061, as further described. The tubular body 3080 may be attached to other portions of the recapture struts 3061. The tubular body 3080 of the frame 3040 may be attached to the body 3002 and/or the cover 3100, e.g. with sutures as described herein, at one or more attachment locations, as further described. The tubular body 3080 may be located within the cavity 3028. In some embodiments, the tubular body 3080 may be located partially or entirely within the foam body 3002, e.g. within the sidewall 3014.

The tubular body 3080 includes a series of proximal struts 3082 and distal struts 3086 (for clarity, only some of the struts 3082, 3086 are labelled in the figures). The proximal struts 3082 and/or distal struts 3086 may have rectangular, circular or other shaped cross-sections. In some embodiments, the proximal struts 3082 and/or distal struts 3086 have a cross-section, e.g. rectangular, with a width that is greater than a thickness, or vice versa, such that the struts 3061 are stiffer in one direction compared to another direction. The struts 3061 may be less stiff in the direction of flexing or bending, for example to facilitate contraction and expansion of the device 3000 in the delivery and expanded configurations. Proximal ends of pairs of adjacent proximal struts 3082 join at proximal apexes 3084. Each proximal strut 3082 is connected at a respective proximal apex 3084 to a respective outer curved portion 3066 of one of the recapture struts 3061. Each distal end of the proximal struts 3082 connects to a distal end of an adjacent proximal strut 3082 and to proximal ends of two distal struts 3086 at an intermediate vertex 3087. Pairs of adjacent distal struts 3086 extend distally to join at a respective distal apex 3088. A repeating pattern 3089, shown as a diamond shape, may be formed by adjacent pairs of proximal struts 3082 and adjacent pairs of distal struts 3086. Some or all of the proximal struts 3082 and/or distal struts 3086 may be attached, e.g. with sutures as described herein, to the body 3002 and/or the cover 3100 at one or more attachment locations. Some or all of the proximal struts 3082 and/or distal struts 3086 may be located within the cavity 3028. In some embodiments, some or all of the proximal struts 3082 and/or distal struts 3086 may be located partially or entirely within the foam body 3002, e.g. within the sidewall 3014.

There are the same number of proximal apexes 3084 as distal apexes 3088. As shown, there are eleven proximal apexes 3084 and eleven distal apexes 3088. The number of proximal and distal apexes 3084, 3088 may each be at least seven, at least eight, at least nine, at least ten, at least eleven, at least twelve, at least thirteen, at least fourteen, at least fifteen, at least sixteen, or fewer or more apexes. In some embodiments, there may not be the same number of proximal apexes 3084 as distal apexes 3088. In some embodiments, there may be more than one row of the pattern, e.g. diamond pattern, formed by the proximal struts 3082 and distal struts 3086. There may be two, three, four or more rows of the pattern. Some or all of the proximal apexes 3084 and/or distal apexes 3088 may be attached, e.g. with sutures as described herein, to the body 3002 and/or the cover 3100 at one or more attachment locations.

The body 3080 may be tubular, e.g. cylindrical or generally cylindrical, in the expanded configuration. The tubular body 3080 may be cylindrical, rounded, segmented, polygonal, tube-like, other shapes, or combinations thereof, all of which are subsumed non-exhaustively under the category "tubular." The tubular shape is formed by the proximal struts 3082 and distal struts 3086 in the expanded configuration. The tubular shape may also be formed by the outer curve portions 3066 of the recapture struts 3061 in the expanded configuration. The tubular shape may also be formed by the foam body 3002 exerting an outward radial force on the frame 3040. The frame 3040 may therefore have a proximal conical section and a cylindrical working length. In some embodiments, the body 3080 may be conical or frustoconical, for example where the distal end is wider than the proximal end or vice versa.

The tubular body 3080 may be referred to as a "landing zone," as described. This landing zone may refer to the axial length of the body 3080, from a distal-most end to a proximal-most end at the transition to recapture struts 3061, in the expanded configuration. The landing zone may have an axial length as measured from the proximal apex 3084 to the distal apex 3088. The length of the landing zone may be 10 mm or about 10 mm. The landing zone may have a length from about 5 mm to about 15 mm, from about 6 mm to about 14 mm, from about 7 mm to about 13 mm, from about 8 mm to about 12 mm, from about 9 mm to about 11 mm, or other lengths. The tubular body 3080 may foreshorten slightly upon expansion of the device 3000 relative to the delivery configuration. The tubular body 3080 has significantly less foreshortening upon expansion than the length of the proximal face 3060. The tubular body 3080 may foreshorten by no more than about 5%, 10%, 15%, 20% or 30%.

The frame 3040 self-expands upon delivery from the sheath. The proximal face 3060 and the tubular body 3080 will self-expand. Upon expansion, the radially outward portions of the tubular body 3080 will contact and compress the foam body 3002 against tissue of the LAA wall. The tubular body 3080, for example the proximal struts 3082 and distal struts 3086, will contact the inner surface 3018 of the sidewall 3014 and press against the sidewall 3014 so that the outer surface 3016 of the sidewall 3014 contacts and compresses against the LAA wall.

When compressed against the LAA wall, the foam body 3002 provides a larger "footprint" than the skeletal frame 3040 components and forms a complete seal. Thus, the sidewall 3014 acts as a force dissipation layer, spreading radial force out from the struts 3082, 3086 of the frame 3040 over a larger area than just the area of the individual struts 3082, 3086 (e.g. a larger area than just the area of the radially outer surfaces of the struts 3082, 3086). The use of the foam material in the body 3002 and the thickness of that foam, such as 2.5 mm, provide advantages in this regard over devices with thinner and less resilient materials than foam. For example, thin fabrics or similar materials that are pressed against the LAA wall with a skeletal frame will not spread the radial force out, and may even sag or otherwise bend, creating gaps and an unsealed portion of the LAA wall. The foam body 3002 as described herein will take the shape of the LAA wall to create a complete circumferential seal and will also spread out the radial forces from the frame 3040 to create a stronger seal and retention with the foam body 3002.

Further, the device 3000 described herein with the compressible body 3002 allows for a structural frame 3040 that is compliant due to the smaller required radial force from the frame 3040. For example, existing devices with a non-compressible fabric material will have a less effective seal, and so the structural elements of those devices must provide larger radial forces to compensate and ensure an effective seal, resulting in a less compliant device. In contrast, the current device 3000 provides advantages in this regard by having the compressible foam body 3002, allowing for among other things smaller radial forces from, and thus better compliance of, the frame 3040, while still providing an effective seal. This structural configuration has a cascading effect in terms of performance advantages. For instance, the compliance of the device 3000 allows for delivery off-axis while still providing an effective seal, among other advantages as further described herein.

The frame 3040 includes a series of proximal anchors 3090. Each proximal anchor 3090 extends from a respective intermediate vertex 3087. The proximal anchors 3090 may extend from other portions of the tubular body 3080. As shown, in the deployed configuration, the proximal anchors 3090 extend from the tubular body 3080 radially and proximally. The proximal anchors 3090 may extend into an adjacent region of the sidewall 3014. The proximal anchors 3090 may extend through the outer surface 3016 of the sidewall 3014 to penetrate tissue adjacent the device 3000.

The frame 3040 includes a series of distal anchors 3094. Each distal anchor 3094 extends from a respective distal apex 3088. The distal anchors 3094 may extend from other portions of the tubular body 3080. As shown, in the deployed configuration, the distal anchors 3094 extend from the tubular body 3080 radially and proximally. The distal anchors 3094 may extend into an adjacent region of the sidewall 3014. The distal anchors 3094 may extend through the outer surface 3016 of the sidewall 3014 to penetrate tissue adjacent the device 3000. The anchors 3090, 3094 may incline radially outward in a proximal direction to engage the tissue to resist proximal movement of the device 3000.

The anchors 3090, 3094 are elongated structural members. The tips of the anchors 3090, 3094 may be sharpened to facilitate tissue engagement and penetration. The anchors 3090, 3094 may be straight, extending generally along a local axis thereof. The anchors 3090, 3094 may have a curved or other non-straight proximal portion where they attach to the tubular body 3080. In some embodiments, the anchors 3090, 3094 or portions thereof may be non-straight, curved, rounded, segmented, other trajectories, or combinations thereof. In some embodiments, the tissue engaging tips may be curved. In some embodiments, the anchors 3090, 3094 may have engagement features extending radially away from the anchor 3090, 3094, such as barbs, hooks, or other features.

The cross-section of the anchors 3090, 3094 may be rectangular. In some embodiments, the cross-section may be circular, rounded, non-rounded, square, rectangular, polygonal, other shapes, or combinations thereof. The cross-sections may or may not be uniform along the length of the anchor 3090, 3094. The anchors 3090, 3094 may be about 0.006" thick and about 0.008" wide. The anchors 3090, 3094 may range from about 0.003" to about 0.009" in thickness and from about 0.003" to about 0.015" in width. The cross-section of the anchors 3090, 3094 may reduce in size, for example taper, toward the distal tip.

In some embodiments, the anchors 3090, 3094 in the deployed configuration are inclined at an incline angle of about 30° relative to a portion of the central axis that extends proximally from the device 3000. This incline angle may be from about 10 degrees to about 50°, from about 15° to about 45°, from about 20° to about 40°, from about 25° to about 35°, or about 30°. This incline angle of the anchors 3090, 3094 in the delivery configuration may be smaller than in the deployed configuration. The deployed anchors 3090, 3094 may have the angle B, as shown in and described with respect to FIGS. 12A-12C.

The anchors 3090, 3094 may have various lengths. The length of the anchor 3090, 3094 is measured from a proximal end that connects to the tubular body 3080 to a distal tissue engaging tip of the anchor. In some embodiments, the length of the anchors 3090, 3094 may be from about 0.5 mm to about 10 mm, from about 1 mm to about 9 mm, from about 2 mm to about 8 mm, from about 3 mm to about 7 mm, from about 4 mm to about 6 mm, about 5 mm, or other greater or lesser lengths. In some embodiments, the anchors 3090, 3094 are 5 mm long. In some embodiments, the anchors 3090, 3094 are about 5 mm long. In some embodiments, the anchors 3090, 3094 have a length of at least 2.5 mm, at least 3 mm, at least 3.5 mm, at least 4 mm, at least 4.5 mm, at least 5 mm or more. The anchors 3090, 3094 may each be the same or similar length. In some embodiments, the anchors 3090, 3094 may not be the same length. In some embodiments, some or all of the proximal anchors 3090 may have lengths that are less than or greater than some or all of the lengths of the distal anchors 3094. The anchors 3090, 3094 may have the length L, as shown in and described with respect to FIGS. 12A-12C. Further, the outer tips of the deployed anchors 3090, 3094 may extend to an outer radial location that is less than, the same as, or more than a radially outermost surface of the foam body 3002, as shown in and described with respect to FIGS. 12A-12C.

In the expanded configuration, the anchors 3090, 3094 extend for a length outside of the uncompressed sidewall 3014. This length of the anchor 3090, 3094 is measured along a local longitudinal axis of the anchor from the outer surface 3016 of the body 3002 to the distal tip of the anchor. The anchors 3090, 3094 may extend through the sidewall 3014 and/or the cover 3100, and then be trimmed so that the anchors 3090, 3094 extend beyond the sidewall 3014 and/or cover 3100 by the desired length. In a free, unconstrained state, the anchors 3090, 3094 extend about 0.5 mm beyond the outer surface 3016 of the sidewall 3014. In some embodiments, in the free, unconstrained state, the anchors 3090, 3094 extend beyond the outer surface 3016 of the sidewall 3014 for a length of from about 0.1 mm to about 1.5 mm, from about 0.2 mm to about 1.25 mm, from about 0.3 mm to about 1.0 mm, from about 0.4 mm to about 0.8 mm, from about 5 mm to about 0.6 mm, or other greater or lesser lengths. In a compressed state, such as in the delivery configuration or after implantation, the anchors 3090, 3094 extend about 1.0 mm beyond the outer surface 3016 of the sidewall 3014. In some embodiments, in the compressed state, the anchors 3090, 3094 extend beyond the outer surface 3016 of the sidewall 3014 for a length of from about 0.25 mm to about 2.5 mm, from about 0.5 mm to about 2 mm, from about 0.75 mm to about 1.5 mm, from about 0.875 mm to 1.125 mm, or other greater or lesser lengths.

The geometry of the anchors 3090, 3094 provides several advantages. For example, the relatively long length allows for flexibility of the anchors 3090, 3094. This provides for potentially less trauma to the LAA tissue should the device 3000 need to be unanchored and/or retrieved. The anchors 3090, 3094 are less susceptible to loss of strength with off-axis orientation within the LAA. Further, the anchors 3090, 3094 provide high resistance to pull out. For instance, the device 3000 may provide at least about 0.5 lb-force of dislodgment resistance from the LAA. Such pullout tests may be simulated with in vitro or benchtop models, as further described below.

The anchors 3090, 3094 in the illustrated embodiment are located in two circumferential rows. One row is located proximal to the other distal row. Each row has ten anchors each. This configuration may be incorporated, for example, in the device 3000 having a foam body 3002 with a free, unconstrained outer diameter of 27 mm. Each row may have fourteen anchors each. This configuration may be incorporated, for example, in the device 3000 having a foam body 3002 with a free, unconstrained outer diameter of 35 mm. In some embodiments, a single row of anchors 3090, 3094 may have twelve anchors. In some embodiments, a single row of anchors 3090, 3094 may have from two to twenty-four, from four to twenty-two, from five to twenty, from six to eighteen, from seven to sixteen, from eight to fifteen, from nine to fourteen, from ten to thirteen anchors, or greater or fewer amounts of anchors 3090 or 3094. In some embodiments, there may only be one row or greater than two rows of anchors. The anchors 3090, 3094 may be spaced circumferentially in a single row. In some embodiments, the device has twenty-four total anchors 3090, 3094, with each row having twelve anchors, and twelve of the proximal recapture struts 3061, for example for the 35 mm diameter device 3000. In some embodiments, the device has twenty total anchors 3090, 3094, with each row having ten anchors, and ten of the proximal recapture struts 3061, for example for the 27 mm diameter device 3000.

In embodiments with multiple rows of anchors 3090, 3094, the rows may be circumferentially offset, as shown. That is, as viewed from the proximal or distal end of the device 3000, the anchors 3090, 3094 are angularly spaced apart from each other about the axis. The anchors 3090, 3094 may not be circumferentially offset, e.g. they may be evenly angularly spaced when viewed as described. The anchors 3090, 3094 are located axially at or near a middle portion of the sidewall 3014. The anchors 3090, 3094 may be located such that the tips of the anchors 3090, 3094 extend to adjacent tissue at a middle portion of the sidewall 3014. The offset and middle locations of the anchors 3090, 3094 may ensure engagement with the LAA tissue distal to the ostium. Having the anchors 3090, 3094 located at the largest width, increases the stability of the device 3000. With a cylindrical or generally cylindrical shaped device 3000, the anchors 3090, 3094 effectively sit on the largest diameter of the device 3000. The cylindrical shape provides advantages over typical LAA occluders which taper distally thus decreasing implant stability and locating the anchors on a smaller diameter than the ostial diameter of the occluding surface. In addition to adding stability, the cylindrical shape of the device 3000 along the axial length helps with dislodgement resistance by allowing the anchors 3090, 3094 to be placed on the largest diameter section of the device 3000. In some embodiments, the anchors 3090, 3094 may be located proximal, distal, or centrally along the length of the frame body 3080. In some embodiments, the anchors 3090, 3094 may not be offset and/or may not be angularly evenly spaced.

The anchors 3090, 3094 may provide advantageous flexibility, as demonstrated by pullout tests and in comparison to existing devices. For example, the device 3000 was tested to determine the force required to dislodge the device 3000 from a simulated tissue model by pulling the device 3000 proximally outward from the model. A low durometer silicone tube with a circular inner diameter (ID) was used as the model. For the device 3000 having a foam body 3002 with a 27 mm outer diameter in a free unconstrained state, tubes with ID's of 16.5 mm, 21 mm and 25 mm were tested. The pullout forces for existing devices drop off significantly going up to a 21 mm model, whereas the forces for the device 3000 drop only slightly.

In the largest diameter (25 mm) model, where there is not a lot of interference in the fit, the forces for the existing devices approach zero as the device does not engage the model wall because the anchors are sitting at a smaller diameter on a trailing edge of the device. The device 3000 consistently resists dislodgment with about 0.7 lbs of force. Since there is very little friction resisting pullout, that force is almost entirely resisted by the anchors 3090, 3094. When examining failure modes, all devices eventually begin to slide out of the model. Upon failure, the anchors 3090, 3094 fold backward or sideways before slipping starts. Assuming 0.7 lbs force is required to cause all twenty anchors 3090, 3094 to fold backward, then the force per anchors is estimated to be about 0.035 lbs.

The frame 3040 may be laser cut. The tubular body 3080 may be laser cut from a single tube. The body 3080 may be cut from a tube having a thickness from about 0.002" to about 0.014", or about 0.008". The tube may have an outer diameter (OD) from about 0.05" to about 0.30". The tube may have an outer diameter (OD) of 0.124" for the 27 mm device 3000 (i.e. the embodiment of the device 3000 having a foam body 3002 with an OD of 27 mm in the unconstrained, free state). The tube may have an OD of 0.163" for the 35 mm device 3000 (i.e. the embodiment of the device 3000 having a foam body 3002 with an OD of 35 mm in the unconstrained, free state).

In some embodiments, the body 3080 is laser cut from a superelastic nitinol tube, however, numerous other biocompatible metallic materials can be utilized such as shape memory Nitinol, stainless steel, MP35N, or Elgiloy. The frame 3040 is self-expandable. In some embodiments, a balloon-expandable frame 3040 could be utilized. Additionally, the body 3080 could be fabricated from drawn wire as opposed to being laser cut from a tube.

As shown, an embodiment of the device 3000 includes the frame 3040 having ten proximal recapture struts 3061 and twenty total anchors 3090, 3094, with the foam body 3002 having an outer diameter of 27 mm. In some embodiments, the device 3000 may include the frame 3040 having fourteen proximal recapture struts 3061 and twenty-eight total anchors 3090, 3094, with the foam body 3002 having an outer diameter of 35 mm.

In one embodiment, the frame 3040 includes a proximal hub 3050, tether pin 3051, front face with ten or fourteen recapture struts 3061, a diamond pattern cylindrical body 3080, and twenty or twenty-eight anchors 3090, 3094. The frame proximal face 3060 supports recapture, the frame body 3080 supports the foam cylinder body 3002, and the anchors 3090, 3094 located on the cylinder provide resistance to embolization.

The design of the device 3000 provides numerous advantages, some of which have been described. As further example, the frame 3040 provides many advantages, including but not limited to: 1) implant radial stiffness/compliance—the frame 3040 provides enhanced radial stiffness while still being sufficiently compliant to allow for off-axis implantation, recapture, etc.; 2) dislodgement resistance—the frame 3040 provides for high pullout strength, as described; 3) transcatheter delivery—the frame 3040 can be compressed into a delivery catheter and then fully expand when delivered; 4) recapture—the frame 3040 allows for recapture/retrieval into the delivery catheter after deployment or even after implantation in the LAA; and 5) mechanical integrity—the frame 3040 has acute and long term structural integrity, for example the ability to withstand loading into the delivery catheter, deployment from the catheter, and cyclic loading/fatigue. The frame 3040 also provides a conformable structure to enable the foam body 3002 to compress against the LAA tissue to facilitate sealing and anchoring with minimal compression (oversizing). The resulting compliance of the frame 3040 provides better anchoring than existing solutions, as described.

As further example, the device 3000 seals against irregularly shaped LAA ostia and necks. For instance, a combination of a Nitinol frame 3040 with a foam body 3002 having a coating of PTFE and cover 3100 of ePTFE contribute to ability of the device 3000 to conform to the anatomy and seal against irregular projections and shapes, while providing a smooth thromboresistent LA surface.

As further example, the device 3000 provides for controlled & safe delivery. The design of the combined frame 3040 and foam body 3002 facilitates delivery in a controlled fashion by slowing the speed of expansion. The bumper 3026 acts as an atraumatic leading edge portion when delivering the implant into the LAA mitigating the risk of injury. The user has the ability to recapture and redeploy the device 3000, if necessary. A flexible tether 3240 attachment, as further described, from the delivery catheter to the device 3000 permits the device 3000 to sit tension free immediately following implantation so the user can ensure final appropriate positioning prior to release of the device 3000.

As further example, the device 3000 provides for simplified placement. The foam-covered cylindrical design makes alignment of the device 3000 with the central axis of the LAA during delivery non-critical (by allowing deployment up to, for example, 45 degrees off-axis), which is designed to simplify the implantation procedure, as further described.

As further example, the device 3000 provides for simple sizing. The foam and frame design contributes to the ability to need only two diameters (e.g., 27 mm and 35 mm) to seal the range of expected LAA configurations and diameters (e.g. targeting LAA diameters of 16 to 33 mm). The conformability of the foam and frame allow the 20 mm long implant to fit into LAA's as short as 10 mm deep. The short landing zone requirement (LAA depth) of the device 3000, combined with the need for only two implant diameters, enables treatment of a wide range of LAA anatomies with minimal need for burdensome echo and CT sizing. The conforming nature of the implant is key to facilitating a simple to use product platform that is adaptable to a variety of anatomic structures.

As further example, the device 3000 provides thromboresistant materials and design. The removable tether leaves a smooth, metal-free surface in the LA. Thromboresistant materials (PTFE-coated foam and an ePTFE cover) create a smooth LA face (no metal attachment connection) to reduce anticoagulation needs, enhance thromboresistance, and encourage endothelialization.

As further example, the device 3000 provides thin, low profile anchors 3090, 3094 around the midpoint of the device 3000 to provide secure yet atraumatic anchoring.

4. Distal Bumper

The foam body 3002 has a distal bumper 3026, for example as shown in FIG. 4C. The bumper 3026 may be a foam distal region of the body 3002, such as a distal portion of the sidewall 3014. The bumper 3026 may be a portion of the foam body 3002 that extends beyond the distal end 3044 of the frame 3040. The bumper 3026 may extend beyond the distal end 3044 of the frame 3040 in the delivery configuration and in the deployed configuration. The body 3002 may be attached to the frame 3040 in various locations such that the body 3002 may stretch in some embodiments, for example in the delivery configuration, to ensure the bumper 3026 extends beyond the frame 3040 upon initially retracting the sheath during delivery.

The device 3000 can conform both in length and diameter due to conformability of both the foam body 3002 and the frame 3040. This allows for the device 3000 to accommodate most patient LAA anatomies with only a couple or few different sizes of the device 3000, such as 27 mm and 35 mm outer diameter body 3002 as described herein, and one length, such as 20 mm. The frame 3040 may thus be shorter than the foam body 3002, resulting in some embodiments in about 5 mm of foam bumper 3026 distal to the distal-most end of the frame 3040. The distal bumper 3026 acts as an atraumatic tip during delivery of the device 3000 and can be compressed following implantation to allow the device 3000 to conform to appendages with a depth (landing zone) as short as 10 mm. This ability to conform both in length and diameter is due to the conformability of both the foam body 3002 and the frame 3040.

The length of the bumper 3026 may be measured axially from the distal-most end of the frame 3040 to the distal surface 3022 of the body 3002. For example, the bumper 3026 may extend from the distal apexes 3088 to the distal surface 3022. The bumper 3026 may have a length of 5 mm or about 5 mm. The bumper 3026 may have a length of about 1 mm, 2 mm, 3 mm, 4 mm, 5 mm, 6 mm, 7 mm, 8 mm, 9 mm or more. The bumper 3026 may have a length from about 2.5 mm to about 7.5 mm, from about 3 mm to about 7 mm, from about 3.5 mm to about 6.5 mm, from about 4 mm to about 6 mm, from about 4.5 mm to about 5.5 mm.

In some embodiments, the bumper 3026 may fold in response to axial and/or radial compression of the device 3000. The bumper 3026 may fold inward, for example radially inward. The folds may be in the axial or approximately in the axial direction. The folds may be circumferential or approximately in the circumferential direction. The folds may be combinations of the radial and circumferential directions, or angled with respect thereto. The folding of the bumper 3026 is further discussed herein, for example in the section "Device Compliance."

5. Cap & Pin

Figure 8A:
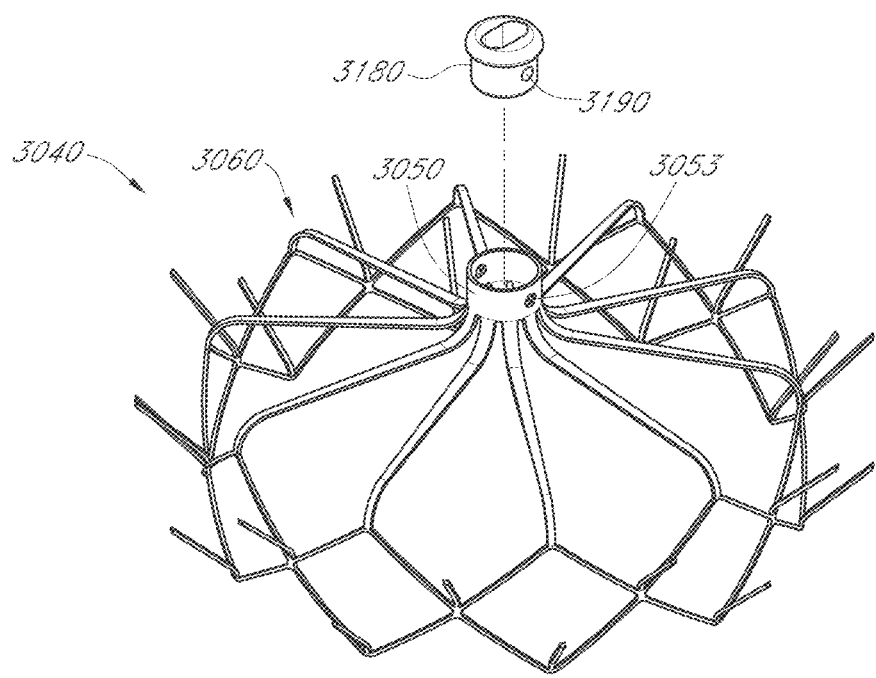
FIGS. 8A-8C are sequential proximal perspective views of an embodiment of a frame showing assembly of a cap and pin with the frame that may be used with the LAA occlusion devices of FIGS. 3A-6E.
Figure 8B:
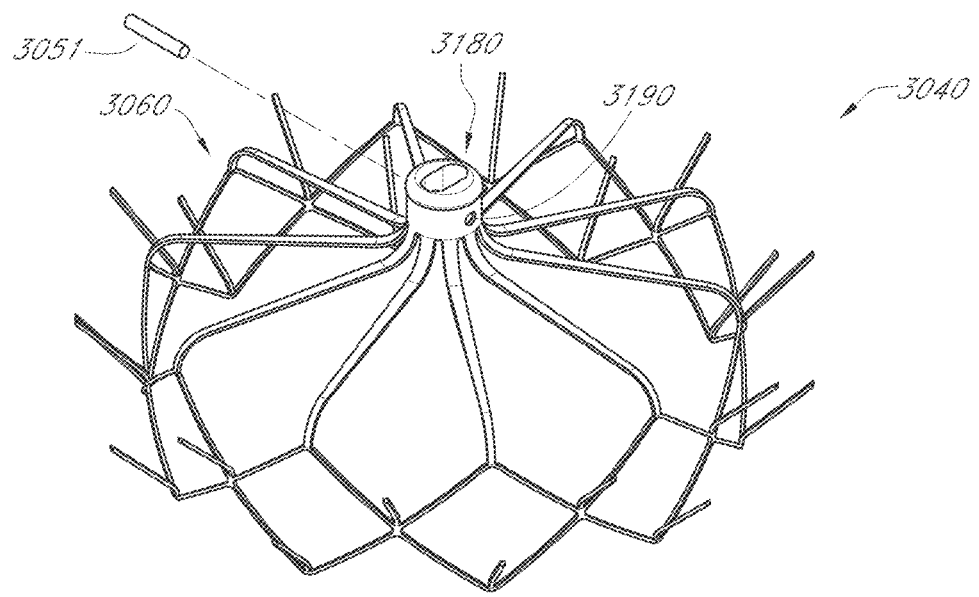
Figure 8C:
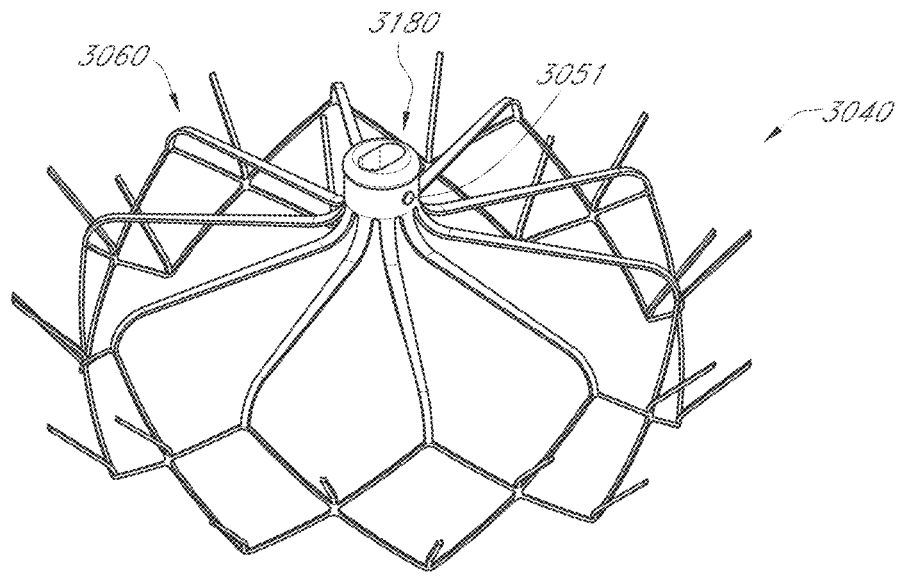
Figure 8D:
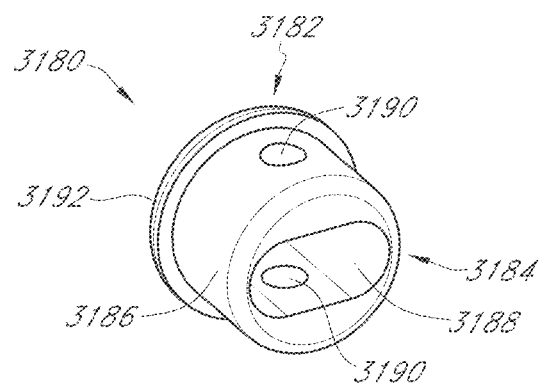
FIG. 8D is a distal perspective view of the cap of FIGS. 8A-8C.

FIGS. 8A-8C are proximal perspective views of the frame 3040 having a cap 3180. FIG. 8D is a distal perspective view of the cap 3180. In some embodiments, the pin 3051 is placed across the proximal hub 3050 diameter and serves to engage the delivery catheter tether 3240 (e.g. a suture), which is wrapped around the pin 3051 for temporary attachment to the delivery catheter 3220, as described further herein for example with respect to FIGS. 7A-7B and 31A-32B. As shown, the hub 3050 has a pair of opposite side openings 3053 extending through a sidewall of the hub 3050. The cap 3180 has a corresponding pair of opposite side openings 3190 extending through a sidewall 3184 of the cap 3180. When the cap 3180 is assembled with the hub 3050, the pin 3051 may be inserted through the aligned pairs of openings 3053, 3182. The assembly can be further secured by welding the ends of the pin 3051 to the hub 3050.

As shown in FIG. 8D, the cap 3180 includes a proximal end 3182 and a distal end 3184. The cap 3180 includes a rounded sidewall 3186 extending from the proximal end 3182 to the distal end 3184. The sidewall 3186 defines a longitudinal opening 3188 through the cap 3180. The sidewall 3186 includes a pair of lateral openings 3190 located opposite each other. The cap 3180 includes a flange 3192 at the proximal end 3182 extending radially outward.

The cap 3180 is formed from titanium and the pin 3051 is formed from Nitinol or superelastic Nitinol. In some embodiments, the cap 3180 and/or pin 3051 may be formed from other materials, for example numerous biocompatible metallic or polymeric materials such as shape memory Nitinol, stainless steel, MP35N, Elgiloy, polycarbonate, polysulfone, polyether ether keytone (PEEK), or polymethyl methylacrylate (PMMA) or other materials.

The cap 3180 and pin 3051 facilitate attachment to the tether 3240. The cap 3180 and pin 3051 also mitigate damage to the foam body 3002 during recapture of the device 3000. The cap 3180 also creates an atraumatic surface for the hub 3050 of the frame 3040. For example, the cap 3180 may prevent the hub 3050 from cutting through the foam body 3002 as the device 3000 is collapsed into an access sheath. Without the cap 3180, the sharp edges of the hub 3050 may shear through the foam body 3002 during recapture of the device 3000 into the access sheath.

6. Loading System

Figure 9:
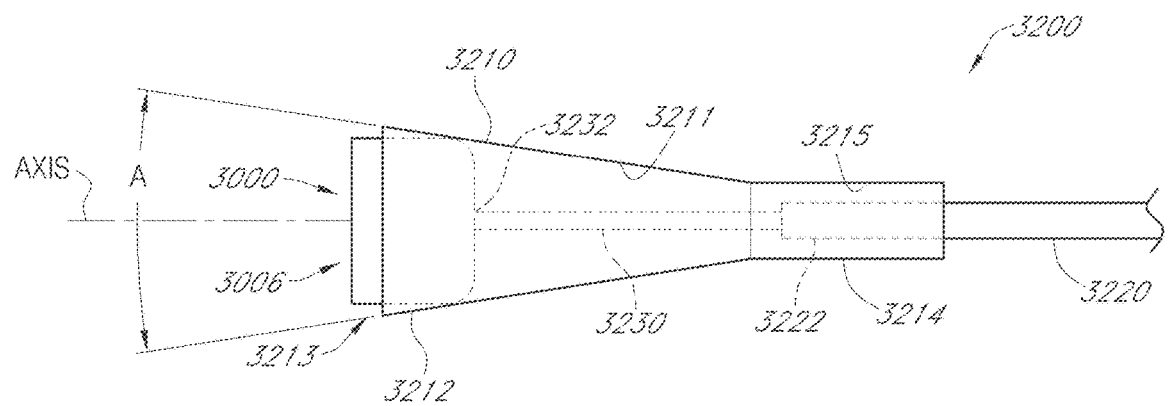
FIG. 9 is a side view of an embodiment of a loading system for loading the device of FIGS. 3A-6E into a delivery catheter.

FIG. 9 is a side view of an embodiment of a loading system 3200 for loading the device 3000 into a delivery catheter 3220. The system 3200 includes a loading tool 3210. The loading tool 3210 has a conical portion 3212, having a distal opening 3213, and a cylindrical portion 3214. The delivery catheter 3220 extends through the cylindrical portion 3214 with a distal end 3222 of the delivery catheter 3220 located within the cylindrical portion 3214. A pusher 3230, such as a pusher catheter, extends through the delivery catheter 3220. A tether 3240 (see, e.g., FIGS. 10A-10C) is attached to the device 3000 and extends through the loading tool 3210, the delivery catheter 3220 and the pusher 3230. The tether 3240 and pusher 3230 are pulled in the proximal direction while the delivery catheter 3220 and the loading tool 3210 are held stationary. The device 3000 is compressed laterally by the conical portion 3212 as the device 3000 is pulled proximally by the tether 3240 through the loading tool 3210. A distal end 3232 of the pusher 3230 remains adjacent to the proximal end 3004 of the device 3000 as the device 3000 is loaded into the delivery catheter 3220. The removable tether 3240, which may be fabricated from ultra-high molecular weight polyethylene (UHMWPE), is used to attach the implant to the delivery catheter. The material UHMWPE for the tether 3240 may provide high strength and low friction to facilitate delivery of the device 3000.

In some embodiments, the conical portion 3212 of the loading tool 3210 has a chamfered distal edge of approximately 45°-75° (degrees), preferably 60°. In some embodiments, the conical portion 3212 has a distal inner diameter (ID) greater than the outer diameter (OD) of the device 3000 and an angle A of ideally between 15° and 25°, and in one implementation about 20°, to appropriately collapse the anchors 3090, 3094 which may protrude off the foam body 3002 surface at an angle of 30° or about 30°. The distal opening of the conical portion 3210, for example the diameter or greatest width, may be greater than the proximal opening of the conical portion 3210, for example the diameter or greatest width, that couples with the cylindrical portion 3214. The cylindrical portion 3214 may have an opening, for example diameter or greatest width, that is smaller than the distal opening of the conical portion 3210 and/or the same or similar size as the opening at the proximal end of the conical portion 3210.

The decreasing width, for example gradual taper, of the loading tool 3210 ensures, for example, that the frame 3040 folds evenly without crossovers or extra strain. The angled conical portion 3212 may ensure that the anchors 3090, 3094 fold or rotate proximally and not distally. The sidewall of the conical portion 3212 may extend at a "total" angle A as measured between two opposite portions of the sidewall, as shown in FIG. 30. The angle A may be from about 12° to about 35°, from about 15° to about 30°, from about 17° to about 25°, from about 18° to about 22°, about 20°, or 20°. The angle A may be at least 10°, at least 15°, at least 20°, at least 25°, or at least 30°. The angle A may be constant along the axial length of the conical portion 3212. The angle of the conical portion 3212 may also be described with respect to a longitudinal geometric center axis, defined by the conical portion 3212 and/or the cylindrical portion 3214. The sidewall may extend in a direction that is at an angle with respect to such longitudinal axis and which is half of the value of the total angle A. This "half angle" may thus be at least 5°, at least 7.5°, at least 10°, at least 12.5°, or at least 15°, etc. The conical portion 3212 may have a frustoconical shape. The cross-sectional shape of the conical portion 3212 perpendicular to its longitudinal axis may be circular or approximately circular. In some embodiments, this cross section may be rounded, non-circular, segmented, other shapes, or combinations thereof. The cross-sectional shape of the conical portions 3212 may be constant along its axis, or there may be different shapes along the axis. In some embodiments, the angle A may change along the axial length of the conical portion 3212, for example where the inner surface is curved in the axial direction.

The loading tool 3210 may be smooth or generally smooth on its inner surface or surfaces. Inner surfaces 3211, 3215 of the conical portion 3212 and/or cylindrical portion 3214 may be smooth or generally smooth. In some embodiments, these inner surfaces 3211, 3215 or portions thereof may not be smooth. In some embodiments, these inner surfaces 3211, 3215 or portions thereof may be smooth, non-smooth, rough, etched, scored, grooved, have varying degrees of roughness or smoothness, other features, or combinations thereof.

In one example, the tool 3210 may be used by positioning a proximal end of a loading body, such as the tool 3210, adjacent the distal end 3222 of the delivery catheter 3220. The loading body may have a sidewall defining a channel therethrough with the distal opening 3213 at a distal end that is larger than a proximal opening at a proximal end. The left atrial appendage occlusion device 3000 may be advanced proximally through the loading body to thereby radially compress the device 3000. The retracting step may comprise pulling the tether 3240 proximally through the delivery catheter 3220. The device may then be received into the distal end 3222 of the delivery catheter 3220. The device 3000 may be radially compressed within the delivery catheter 3220 having an outer diameter of no more than fifteen French. In some embodiments, the device 3000 may be radially compressed within the delivery catheter 3220 having an outer diameter of no more than ten, eleven, twelve, thirteen, fourteen, fifteen, sixteen, seventeen, eighteen, nineteen, or twenty French. The proximal end of the loading tool 3210 may have an inner diameter configured to provide an interference fit with the distal end 3222 of the delivery catheter 3220. The proximal end of the loading tool, 3210, such as the cylindrical portion 3214, may have an inner diameter slightly larger than the outer diameter of the delivery catheter 3220, for instance slightly larger than 5 mm for a delivery catheter 3220 having an outer diameter of fifteen French. The device 3000 may compress radially to a compressed width in a constrained state that is less than fifty, forty, thirty, twenty, ten, and/or five percent of a radial uncompressed width of the device in an unconstrained state. The radial widths here may be measured perpendicularly to a longitudinal axis of the device 3000, such as defined by the tubular foam body 3002.

The loading tool 3210 may be formed of a material that is biocompatible, strong, transparent and can be molded smooth to minimize friction, such as polycarbonate. In some embodiments, the loading tool 3210 could be formed from hard plastics like Delrin, UHMWPE, Ultem®, polyetherimide, acrylic, metals like stainless steel, aluminum, other materials, or combinations thereof. In some embodiments, the loading tool 3210 may have one or more coatings. Such coating may be applied to reduce friction and therefore loading forces. The coating may be silicone, hydrophilics, various oils, other suitable coatings, or combinations thereof. Additional embodiments of a loading tool and system are described herein, for example with respect to FIGS. 22A-22B.

7. Delivery System

Figure 10A:
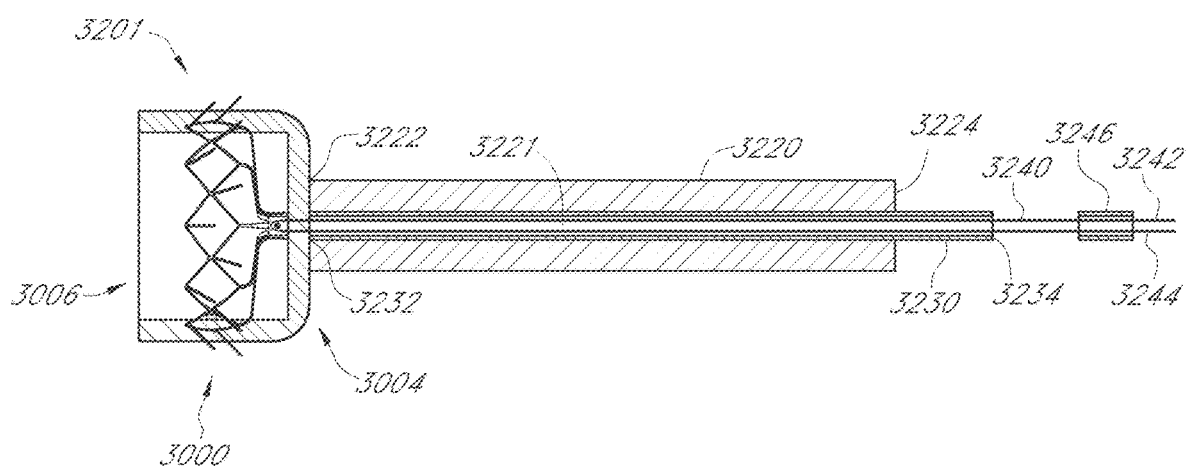
FIG. 10A is a side view of a schematic of a transcatheter delivery system for delivering the device of FIGS. 3A-6E via an artery or vein.
Figure 10B:
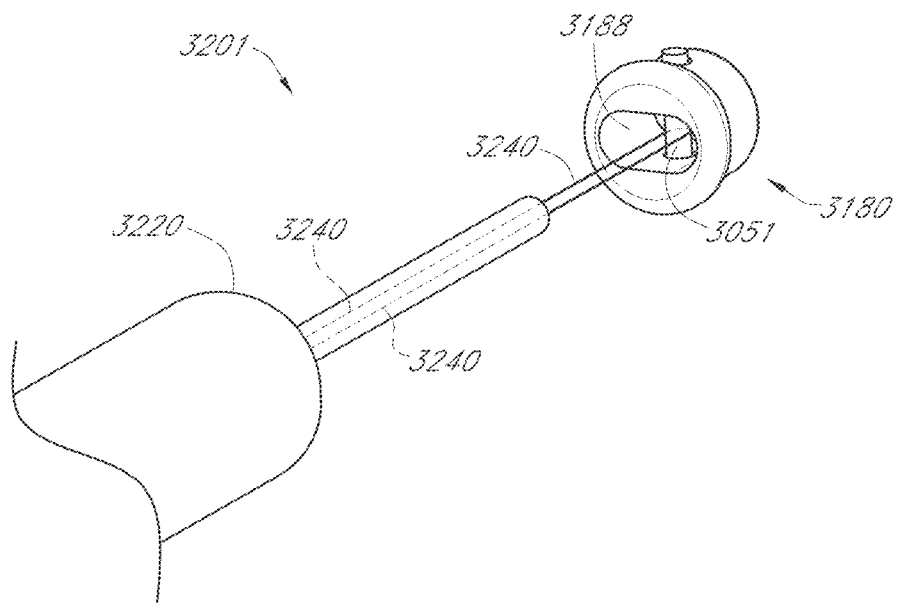
FIGS. 10B-10C are proximal and distal perspective views, respectively, of the delivery system of FIG. 10A, showing an associated tether release mechanism and method.
Figure 10C:
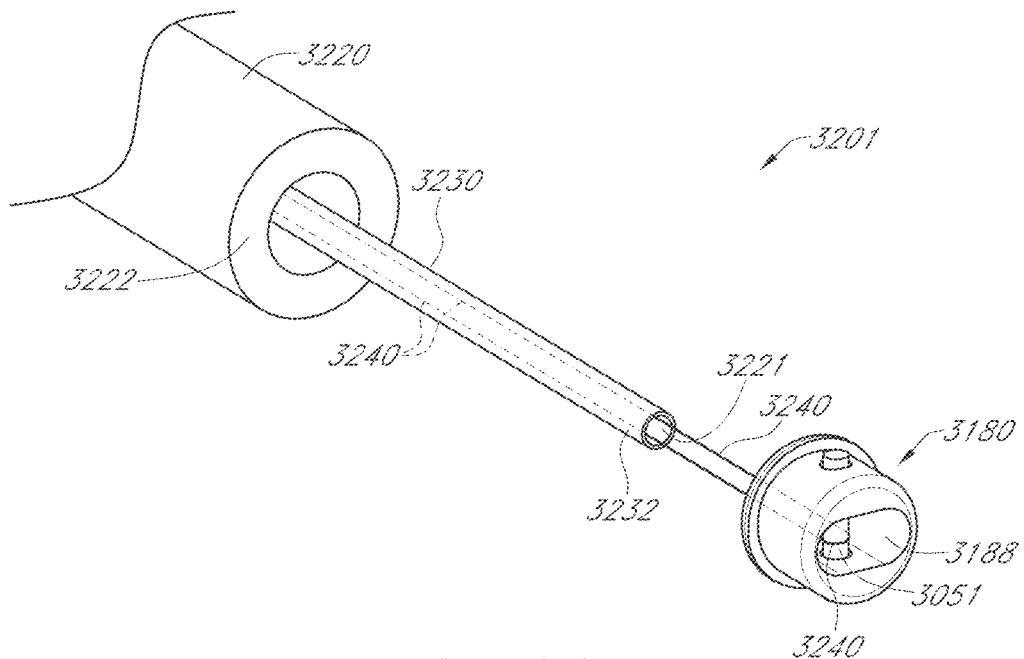

FIG. 10A is a side view of a schematic of a delivery system 3201 for delivering the device 3000. FIGS. 10B-10C are additional views of the system 3201. Various embodiments and features for delivery systems are also shown and described herein in FIGS. 22A-27C. Any of these delivery systems may have the same or similar features and/or functions as the others. As shown in FIG. 10A, the delivery system 3201 includes the delivery catheter 3220 having a distal end 3222 and a proximal end 3224. The delivery system 3201 includes the pusher 3230, such as a pusher catheter, having a distal end 3232 and a proximal end 3234. The tether 3240 includes a first end 3242 and a second end 3244. A restraint 3246 secures the first and second ends 3242, 3244.

To deliver the device 3000 to the LAA, an access sheath is placed across the interatrial septum into the LAA through which the delivery catheter 3220, containing the device 3000, is placed. The device 3000 is loaded into the distal end 3222 of the delivery catheter 3220 using the loading tool 3210, either at the point of manufacture or at the treatment site. To load the implant device 3000, the pusher 3230 and tether 3240 are pulled proximally, collapsing the implant device 3000 as it enters the distal tip of the delivery catheter 3220. Once the loaded delivery catheter 3220 is placed through the sheath into the LAA, the pusher 3230, such as a catheter or rod, is held axially steady as the delivery catheter 3220 and access sheath are simultaneously retracted proximally, deploying the implant device 3000.

The tether 3220 passes from the proximal end of the delivery catheter 3220, through an opening 3221 of the catheter pusher 3230, around the implant tether pin 3051, and back through the delivery catheter 3220. When both ends of the tether 3240 (held together by the restraint 3246 at the proximal end of the catheter) are pulled, the device 3000 is pulled into the delivery catheter 3220. Once the device 3000 is properly placed in the anatomy, one end of the ends 3242, 3244 of the tether 3240 is cut and the entire tether 3240 can be removed from the system by pulling proximally on the uncut end and sliding the cut end distally into the system and around the pin 3051, disengaging from the pin 3051. The distal end 3232 of the pusher 3230 and/or the distal end 3222 of the delivery catheter 3220 may contact, for example push against, the proximal end of the device 3000, such as in the relative locations shown in FIG. 10A. For example, the distal end 3232 of the pusher 3230 may contact and prevent proximal movement of the device 3000 during tether 3240 retrieval, as further described herein. Further details of the release of the tether are provided herein, for example with respect to FIGS. 10B-11B.

In some embodiments, the delivery system 3201 may include other features. For example, the delivery catheter 3220 may include an injection lumen. The injection lumen may allow for injecting a radiopaque dye distal to the device 3000 following implantation to check for leaks using fluoroscopy.

8. Tether Release System

FIGS. 10B and 10C are proximal and distal perspective views of the delivery system 3201. An approach to releasing the tether, and other features of the system, are described in this section. For clarity, some features are not shown, such as the cover 3100, foam body 3002, and frame 3040.

The system 3201 as shown in FIGS. 10B and 10C shows the delivery catheter 3220, the pusher 3230 and the hub 3050 in different axial positions relative to each other. In some embodiments, during release, the distal end 3222 of the delivery catheter 3220 may be co-extensive with, or otherwise near or adjacent, the distal end 3232 of the pusher 3230. Further, the distal ends 3222 and/or 3232 may contact or be adjacent the proximal end 3004 of the device 3000, such as contacting or adjacent the cover 3100 and/or foam body 3002. In some embodiments, the distal end 3232 of the pusher may be located distally of the distal end 3222 of the delivery catheter 3220, as shown, during tether 3240 release.

The tether 3240 may extend from a proximal end of the pusher 3230, through the opening 3221 of the pusher 3230, wrap around the pin 3051, and extend proximally back through the opening 3221 of the pusher 3230 and out the proximal end of the pusher 3230, as described with respect to FIG. 10A. The tether 3240 may extend through the cover 3100 and foam body 3002. The tether 3240 may extend distally through first aligned paths in the cover 3100 and foam body 3002, around the pin 3051, and extend proximally back through second aligned paths in the cover 3100 and foam body 3002. The tether 3240 may extend through openings within the inner cover 3101, as described for example with respect to FIGS. 3D and 5D. The tether 3240 may only extend around a distal surface or surfaces of the pin 3051, as shown. The tether 3240 may extend distally and wrap around the pin 3051 and extend distally at 180° or approximately 180° relative to the proximally extending portion. In some embodiments, the tether 3240 may be wrapped one or more times, for example two, three or more times, around the pin 3051. In some embodiments, the tether 3240 may be on a spool about the pin 3051. In some embodiments, the tether 3240 may be wrapped, partially, fully or multiple times, about a bushing that is rotatable coupled about the pin 3051.

The system 3201 may facilitate removal of the tether 3240 while the pusher catheter 3230 is in contact with the device 3000. Such contact may assist, for example, with avoiding or reducing inadvertent dislodgement of the device 3000 from the LAA after implantation and anchoring. For instance, during release of the tether 3240, the pusher 3230 may have the positioning relative to the device 3000 as shown in FIG. 10A. The pusher 3230 may contact the device 3000 on the proximal end 3002 of the device to prevent or reduce any proximal movement of the device 3000 upon tether 3240 removal. For example, there may be friction between the tether 3240 and the pin 3051 as the tether 3240 unwraps about the pin 3051. The distal end of the pusher 3230 may prevent this friction or other forces from dislodging or otherwise moving the device 3000 proximally. In some embodiments, the delivery catheter 3220 may also be contacting, adjacent to, etc. the device 3000. In some embodiments, during tether release and removal, the distal ends of the delivery catheter 3220 and pusher 3230 may be axially co-extensive, adjacent or near each other, etc., as described. Further, the tether 3240 may be proximally pulled completely out of the delivery catheter 3220 and/or pusher 3230 before the delivery catheter 3220 and/or pusher 3230 are removed from the patient. In some embodiments, the tether 3240 may be removed from the patient along with the delivery catheter 3220 and/or pusher 3230, for example while the tether 3240 is still entirely or partially within the pusher 3230.

Figure 11A:
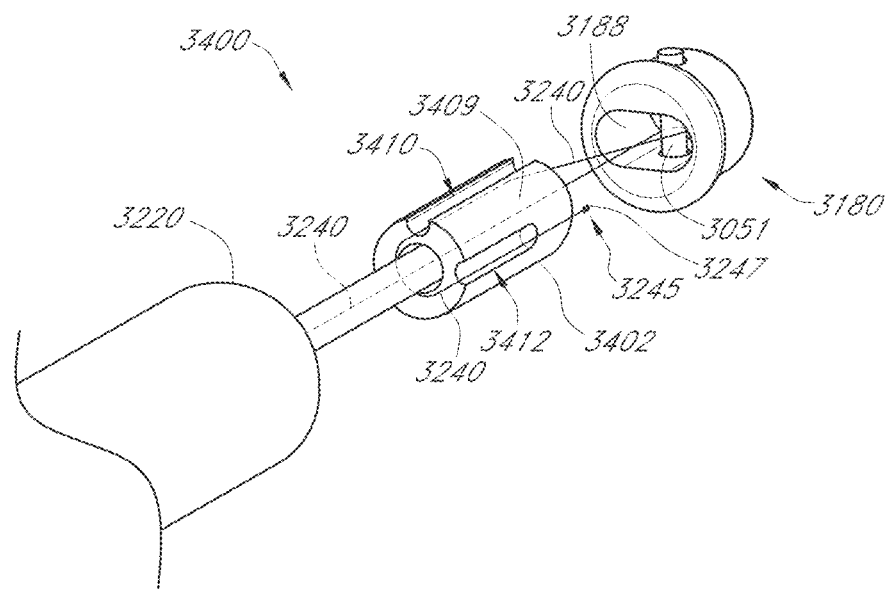
FIGS. 11A and 11B are proximal and distal perspective views respectively of another embodiment of a tether release system that may be used with the device of FIGS. 3A-6E.
Figure 11B:
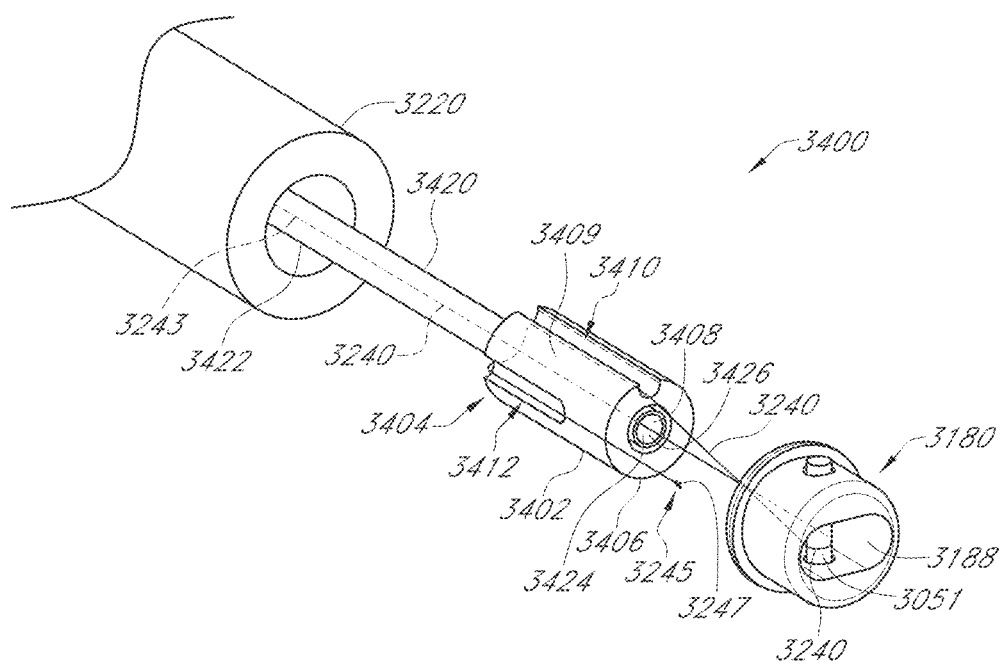

FIGS. 11A and 11B are proximal and distal perspective views respectively of another embodiment of a tether release system 3400. The release system 3400 includes a tube 3420 and a lock 3402. The tube 3420 has a proximal end 3422 and a distal end 3424. An opening 3426 extends through the tube 3420. The system 3400 may be used similarly as described with respect to the system 3201, except as otherwise noted. For example, the pusher 3230 and/or tube 3420 may contact the device 3000 during tether removal, as described.

The lock 3402 includes a proximal end 3404 and a distal end 3406. An opening 3408 defined by a sidewall 3409 extends through the lock 3402 from the proximal end 3404 to the distal end 3406. The tube 3420 extends through the opening 3408 at the proximal end 3404 of the lock 3402 and to the distal end 3406 of the opening 3408. The sidewall 3409 of the lock 3402 has a first groove 3410 extending longitudinally from the proximal end 3404 to the distal end 3406 and extending radially partially through the thickness of the sidewall 3409. The sidewall 3409 of the lock 3402 has a second groove 3412 extending longitudinally from the proximal end 3404 partially along the sidewall 3409 toward the distal end 3406 and radially partially through the thickness of the sidewall 3409.

The tether 3240 includes a first end 3243 and the second end 3245. The tether 3240 extends distally from the first end 3243 within the opening 3426 of the tube 3240 and out through the distal end 3424 of the tube 3420 to the cap 3180. The tether 3240 extends distally into the opening 3188 of the cap 3180 and around the pin 3051 and back in the proximal direction. The tether 3240 then extends proximally into the first groove 3410 of the lock 3402, around the proximal end 3404 of the lock 3402, and then distally into and through the second groove 3412. The tether 3240 terminates at the second end 3245 in a knot 3247.

In use, the knot 3247 may be secured due to the relative location of the lock 3402 and the pusher catheter 3230 inside the delivery catheter 3220. The knot 3247 may be prevented from advancing distally due to the inner diameter of the distal end of the pusher 3230 fitting tightly about the outer diameter of the lock 3402. The grooves 3410 and/or 3412 in the lock 3402 may hold the tether 3240 in an orientation that prevents the tether 3240 from slipping (e.g., if pulled hard enough) when the lock 3402 is engaged in the pusher 3230. The pusher 3230 may be advanced distally to expose the lock 3402, for example the full length of the lock 3402, or portions thereof. When the proximal end of the tether 3240 is pulled proximally, the knot 3247 falls away from the second groove 3412, advances around the proximal end 3404 of the lock 3402, advances distally by falling away from the first groove 3410, into the cap 3180 and around the pin 3051, and then distally through the opening 3408 of the lock 3402 and can be retrieved with the pusher 3230. In some embodiments, the distal end of the lock 3402 may be located axially proximal to the distal end of the tube 3420, for example to contact the device 3000 with the tube 3420 to prevent proximal movement of the device 3000 after implantation, as described above. Additional embodiments of a delivery system and associate features, such as a proximal delivery control handle and dual lumen delivery catheter pusher, are described herein, for example with respect to FIGS. 23A-27C.

9. Off-Axis Delivery and Deployment

The device 3000 may be deployed off-axis within an LAA while still providing a complete, stable, and atraumatic seal. In some embodiments, the device 3000 may be deployed at an angle of at least about 15° or 25° and in some embodiments as much as 35° or 45°, for example, relative to a central longitudinal LAA axis and still provide an effective seal. The LAA axis here is defined as the geometric center of the ostium to the LAA, and tracks the best fit geometric center of the LAA cavity.

This ability of the device 3000 to be deployed off-axis is due in part to the relatively thick, compressible foam body 3002 material, the compliant frame 3040 and the cylindrical shape of the device 3000 with the foam bumper 3026. The device 3000 is stable within the LAA despite having a length that is less than the diameter, or having L/D<1. As described, the length may be 20 mm for the device 3000 having an OD of both 27 mm and 35 mm. Thus not only is flexibility and simplicity allowed with manufacturing processes by having one length, but also stability and effectiveness of the device in use. Further, the axial compressibility of the bumper 3026, combined with the axially compliant frame 3040, allows a 20 mm long device 3000 to be placed within a 10 mm deep LAA, whereas existing LAA closure devices require longer landing zones, or at least landing zones equal to the size of the length of the metallic frame.

In some embodiments, the device 3000 may be configured to allow for sufficient flow of blood in case of accidental embolization, as described herein. Further, the device 3000 may be configured to allow for sufficient flow of blood even if the device 3000 embolizes and is misaligned with the direction of flow of blood. For example, the device 3000 may define a longitudinal axis, and the direction of flow of blood may define a flow axis. The device longitudinal axis may be at an angle with respect to the flow axis and still provide for a sufficient blood flow through the device 3000 should it embolize and lodge within the circulatory system of a patient. Thus, the capabilities of the device 3000 with regard to flow of blood through the device in case of embolization, or tests thereof with water under controlled conditions, as described herein for example with respect to the section "Proximal Cover," may also apply to the device 3000 in such off-axis configurations or orientations with the circulatory system of the body. The device axis may be at an angle of five, ten, twenty, thirty or more degrees with respect to the flow axis and still provide sufficient flow of blood through the device 3000.

10. Anchor/Foam Interface

Figure 12A:
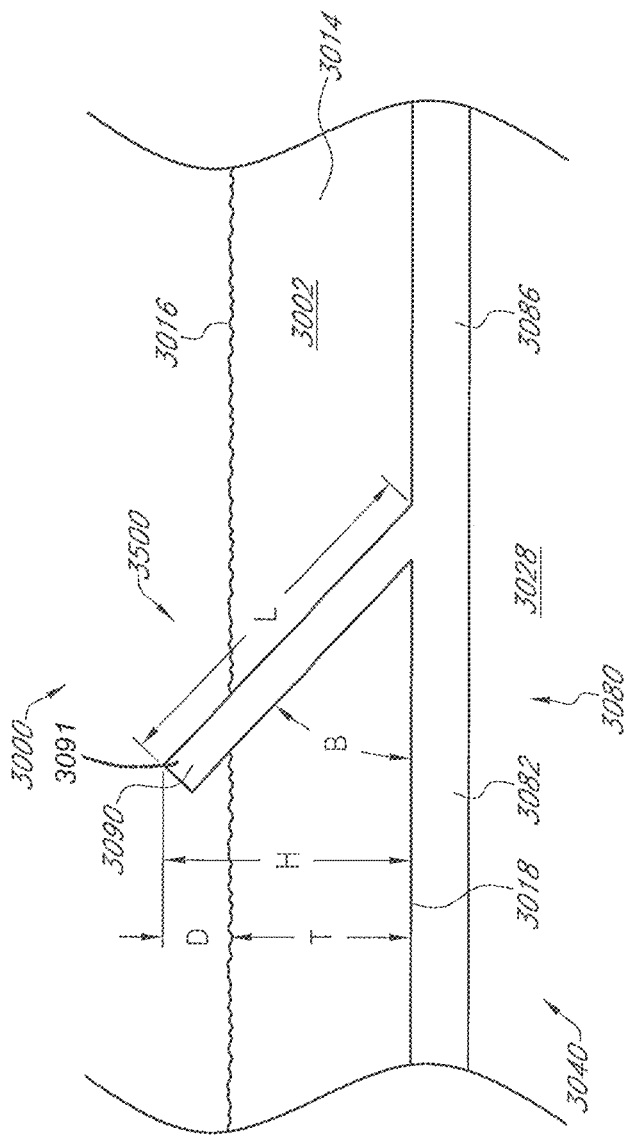
FIGS. 12A-12C depict various embodiments of an anchor/foam interface that may be used with the LAA occlusion devices of FIGS. 3A-6E.
Figure 12B:
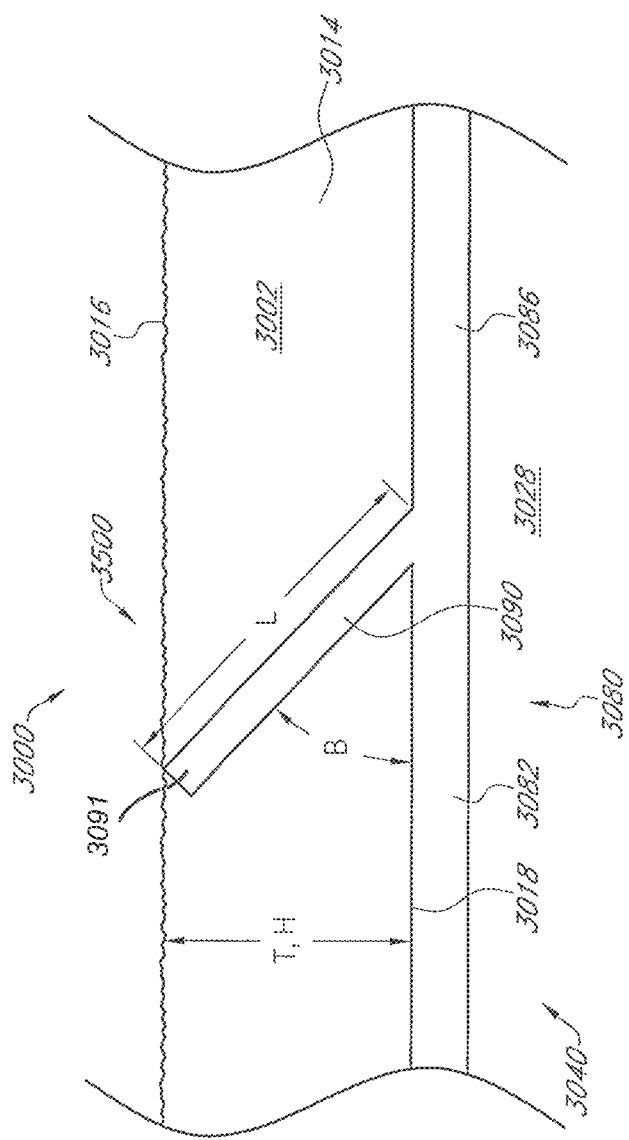
Figure 12C:
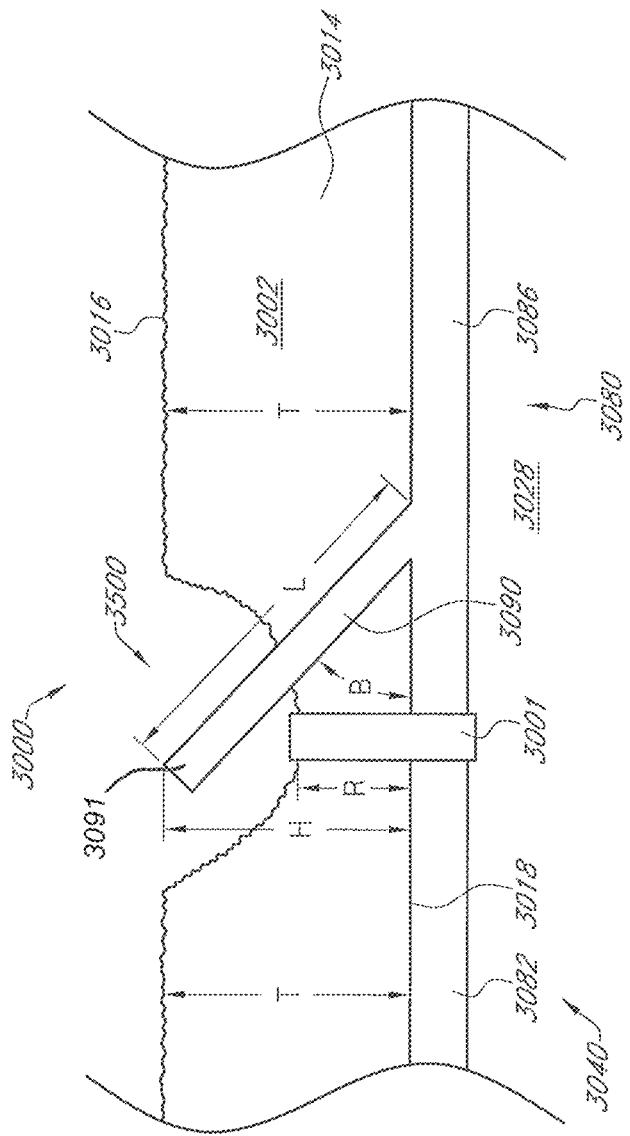

As described, the frame 3040 with anchors 3090, 3094 and foam body 3002 may have a variety of geometries, such as lengths, thicknesses, etc. This section discusses some particular embodiments of the frame 3040, in particular the anchors 3090, 3094, and the foam body 3002. FIGS. 12A-12C depict various embodiments of an anchor/foam interface 3500, using the anchor 3090 as an illustrative example. FIGS. 12A-12C are side cross-section views of a portion of the device 3000 showing an embodiment of the interface 3500. In some embodiments, the outer tips of the anchors 3090, 3094 may, or may not, extend radially beyond portions of the outer surface 3016 of the foam body 3002, even in an unconstrained configuration, as further described herein.

The interface 3500 includes a portion of the tubular body 3080 of the frame 3040, having the proximal strut 3082 and the distal strut 3086, as described in further detail herein, for example with respect to FIG. 7A. The anchor 3090 extends radially outwardly in a proximal direction from the frame 3040, such as from the tubular body 3080. The same or similar features and/or functionalities as described in this section with respect to the interface 3500 having the anchor 3090 may apply to other anchor/foam interfaces with other anchors, such as anchor/foam interfaces with the distal anchor 3094. For example, the frame 3080 could have a distal end at the base of the anchor 3094, where the distal apes 3088 is located (see, e.g., FIG. 7A).

As shown in FIGS. 12A-12C, the anchor 3090 extends outwardly and proximally from the frame 3040, which may be from the proximal apex 3084 as described herein. The anchor 3090 has an axial length L. The length L extends from the distal base of the anchor 3090 at the frame 3040 to a proximal tip 3091 of the anchor 3090. The length L may include only the straight portion of the anchor 3090, for example if the base of the anchor 3090 is bent. In some embodiments, the length L can include the complete anchor 3090, such that L extends axially along the anchor 3090 from a tip 3091 of the anchor 3090 to the frame 3040. The anchor 3090 is shown with a flat end, but it may be sharpened, angled, etc. The length L may extend proximally to the farthest endpoint axially along the length of the anchor 3090, such as to the tip 3091. In some embodiments, L is 2.5 mm, about 2.5 mm, or from about 2.25 mm to about 2.75 mm. The length L may be a variety of other lengths or within other ranges of lengths, for example as described in further detail herein with respect to the anchors 3090, 3094 in the section "Compliant Frame."

The anchor 3090 extends at an angle B relative to the proximal strut 3082. In some embodiments, the proximal strut 3082 as shown may be considered a projection of the proximal strut 3082 onto a vertical plane that intersects the longitudinal axis of the device 3000 and the anchor 3090. Thus the angle B may be relative to such plane and/or to the strut 3082. For simplicity, the angle B will be described relative to the strut 3082. The angle B may be 30° or about 30°. The angle B may be a variety of other angles or within ranges of angles, for example as described in further detail herein with respect to the anchors 3090, 3094 in the section "Compliant Frame." The anchor further has a radial height H. The radial height H may be the radially outermost extent of the anchor 3090, such as the proximal tip 3091 of the anchor 3090. The length L and angle B may define the radial height H of the anchor 3090. The height H may be in a direction perpendicular to the longitudinal axis of the device 3000 (see, e.g., FIG. 5B).

Further shown is the sidewall 3014 of the foam body 3002. The sidewall 3014 has a thickness T. The thickness T extends radially outward from the inner surface 3018 to the outer surface 3016 of the sidewall 3014. The thickness T may extend radially outward perpendicularly to the longitudinal axis of the device 3000. The thickness T may be equal to a distance from a radially outer portion of the frame 3040 to the outer surface 3016 of the sidewall 3014, for example where the inner surface 3018 of the sidewall 3014 contacts the outside of the frame struts 3082, 3086. The thickness T could be the thickness of the sidewall 3014 in an unconstrained configuration, a compressed configuration while inside the delivery catheter, or a compressed configuration after implantation within the LAA, as further described. The measurement of the thickness T of the sidewall 3014 may be in the same direction as the measurement of the height H of the anchor 3090. The thickness T of the sidewall 3014 may be 2.5 mm or about 2.5 mm. The thickness T of the sidewall 3014 may be other values or ranges of values, for example as described in further detail herein in the section "Compressible Foam Body."

As shown in FIG. 12A, in some embodiments, the height H of the anchor 3090 may be greater than the thickness T of the foam sidewall 3014. The difference may be equal to a delta D. The device 3000 may have this configuration in an unconstrained configuration, for example as resting on a tabletop as described herein. The delta D may be from about 0.05 mm to about 5 mm, from about 0.075 mm to about 4 mm, from about 0.1 mm to about 3 mm, from about 0.2 mm to about 2 mm, from about 0.3 mm to about 1.5 mm, from about 0.4 mm to about 1 mm, about 0.5 mm, or 0.5 mm. In some embodiments, these example values for delta D may be negative, where T is greater than H. In some embodiments, the delta D may be zero, as described with respect to FIG. 12B.

As shown in FIG. 12B, in some embodiments, the height H of the anchor 3090 may be the same as or about the same as the thickness T of the foam sidewall 3014. Thus the delta D may be zero or about zero. The device 3000 may have this configuration in an unconstrained configuration, for example as resting on a tabletop as described herein. The anchors 3090, 3094 may extend through the foam body 3002 to the outer surface 3016 in the unconstrained configuration, and then extend radially outward beyond the outer surface 3016 when loaded for delivery and/or after implantation in the LAA. In other embodiments, the foam body 3002 is locally compressed so the anchor extends beyond the outer surface 3016, as further described.

As shown in FIG. 12C, the device 3000 may include one or more attachments, such as sutures, for example the attachment 3001 described in further detail herein with respect to FIG. 5D. The attachment 3001 may connect the foam body 3002 to the frame 3040. As shown, the attachment 3001 may extend out through the sidewall 3014 and around the outer surface 3016, back in through the sidewall 3014 and around the frame 3040, such as around the proximal strut 3082. The attachment 3001 may locally compress the sidewall 3014 as shown. The sidewall 3014 may have a local radial thickness R. The thickness R may be less than the thickness T. The thickness R may be a local minimum of the thickness of the foam body 3002. The thickness T may be located adjacent or otherwise around the location of the thickness R. The sidewall 3014 may increase in thickness from the location of the thickness R to the surrounding thicknesses T. The increase may be gradual or abrupt.

The local compression of the sidewall 3014 may allow for the anchor 3090 to extend proximally and outwardly beyond the outer surface 3016 of the foam body 3002. As shown, the attachment 3001 may locally compress the thickness of the sidewall 3014 such that the proximal tip 3091 of the anchor 3090 extends at the angle B for the length L beyond the outer surface 3016 of the foam body 3002. The attachment 3001 may be located proximally to the anchor 3090 as shown, or in other location, such as distally to the anchor 3090, adjacent the base of the anchor 3090, farther proximally/ distally from the base of the anchor 3090, etc. The attachment 3090 may be located and configured to allow for local compression of the sidewall 3014 to allow the tip 3091 of the anchor 3090 to extend beyond the outer surface 3016 of the foam that is located directly radially inwardly of the tip 3091 of the anchor 3090. In some embodiments the attachment 3001 may be located directly radially inwardly of the tip 3091 of the anchor 3090 (e.g., directly "below" the tip 3091 of the anchor 3090 as oriented in the figure). In some embodiments, there may be multiple attachments 3001 distributed axially along the frame 3040 and all contributing to a single local compression of the foam body 3002 about a particular one of the anchors 3090.

The foam sidewall 3014 may be compressed into the configuration shown in FIG. 12C in an unconstrained configuration. The foam sidewall 3014 may be compressed into the configuration shown in FIG. 12C in a constrained configuration, for example within the delivery catheter or after deployment from the delivery catheter. The foam sidewall 3014 may be compressed into the configuration shown in FIG. 12C from the configurations shown or described with respect to FIG. 12A or 12B. Thus in FIG. 12C, the height H may equal to or approximately equal to the thickness T, or the height H may be greater or less than the thickness T. In some embodiments, in an unconstrained configuration, the length L is 2.5 mm or about 2.5 mm, the angle B is 30° or about 30°, and the thickness T is 2.5 mm or about 2.5 mm.

Design of the anchor length may be based on a balance between longer length to provide flexibility to assist with removal, and shorter length for not penetrating through the LAA wall. The anchors 3090, 3094 may be flexible and capable of bending in the distal direction due to their length. The anchors 3090, 3094 are thus less likely to tear tissue during repositioning and therefore less traumatic. The anchors 3090, 3094 may be longer than other tissue engaging features of existing solutions for LAA occlusion. In some embodiments of the device 3000, the anchors 3090, 3094 are designed to be long enough to effectively anchor into the LAA wall. The foam body 3002 and corresponding thickness of the sidewall 3014 allows the anchors 3090, 3094 to have longer length. An advantage of making the anchors 3090, 3094 longer is to increase their flexibility, making them less damaging to tissue during removal and repositioning. However, anchors 3090, 3094 beyond a certain length may penetrate through the LAA wall, which is not desirable. The foam body 3002 and thickness thereof assists with preserving the advantageous longer length of the anchors 3090, 3094 while mitigating the risk of the anchors 3090, 3094 penetrating through the LAA wall. For example, the foam sidewall 3014 between the struts of the frame 3040 and the tips 3091 of the anchors 3090, 3094 limits how far the anchors 3090, 3094 will penetrate allowing for longer and therefore more flexible anchors 3090, 3094.

For example, with a 2.5 mm foam sidewall 3014 thickness, the anchors 3090, 3094 may be 2.5 mm in axial length and formed at an angle between 30-40 degrees, or 25-45 degrees, off the struts. In some embodiments, as discussed, when the frame 3040 is first placed into the foam body 3002 and anchors 3090, 3094 pierce into the foam sidewall 3014, the tips 3091 of the anchors 3090, 3094 may not extend all the way through the foam as the anchors 3090, 3094 may be radially too short. In some embodiments, the frame 3040 OD is about 24 mm and the foam body 3002, such as foam cup shape, has a sidewall 3014 with an ID of about 22 mm. So there may be an interference fit where the frame 3040 bulges into the foam sidewall 3014. With the anchor 3090, 3094 length and angle, the tips 3091 of the anchors 3090, 3094 are at about 27 mm diameter, which corresponds to just getting to the outer surface 3016 of the sidewall 3014. As discussed, the assembly may be attached by suturing the foam body 3002, and the frame 3040 (and in some locations the cover 3100) together at every anchor-frame interface location. This may cause a dimpling of the foam body 3002 local to the corresponding anchor 3090, 3094, thus exposing a length of the anchor 3090, 3094 at the outer surface 3016. The exposed length of the anchor 3090, 3094 may be a fraction of the total anchor 3090, 3094 length. Further, the anchor 3090, 3094 length and radial height of the foam sidewall 3014 surrounding the anchor 3090, 3094 can be adjusted to expose the desired amount of the anchor 3090, 3094.

In some embodiments, the tip 3091 may be exposed beyond the foam body 3002 when the foam is compressed, but the tip 3091 may be positioned within the foam, below the outer surface 3016, when the foam is uncompressed. Thus, with the foam uncompressed the tip 3091 may not be positioned radially outwardly relative to the outer surface 3016, but with the foam compressed the tip 3091 may be positioned radially outwardly relative to the adjacent portion of the outer surface 3016. Therefore, the tip 3091 may not be exposed with "H" less than "T" in the uncompressed configuration, and the tip 3091 may be exposed with "H" greater than "T" in the compressed configuration.

11. Device Compliance

The device 3000 is capable of conforming to the geometry of the LAA. The device 3000 is designed for compliance such that it can conform to the LAA and reduce or minimize remodeling of the LAA. For example, the device 3000 may be implanted into the LAA and after a period of time the ostium or opening of the LAA may have the same or similar profile as before implantation of the device 3000. Further, the device 3000 may exhibit such properties while conforming to extreme non-circular shapes, both at the opening of the LAA and within the LAA. A single size of the device 3000 may be used for all or a wide range of patients with varying geometries, due to the compliance and other advantages.

Figure 13A:
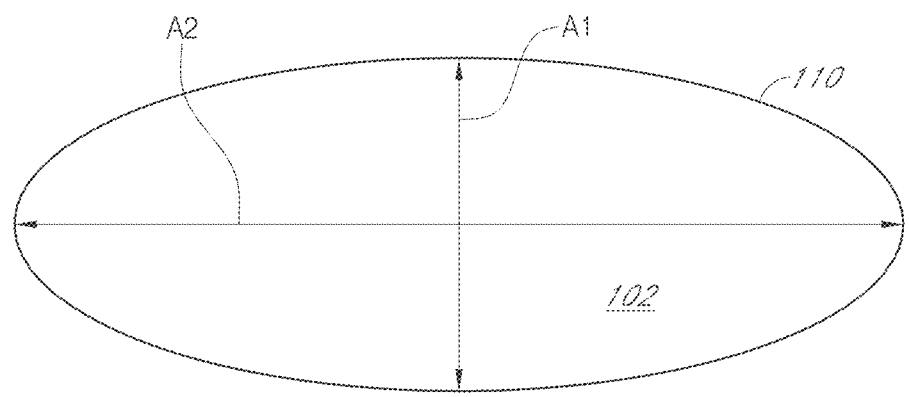
FIG. 13A is a schematic showing an embodiment of a profile of an ostium and an LAA.

FIG. 13A is a schematic showing an embodiment of a profile of the ostium 110. The view shown may be looking into the LAA, for example in a plane that is perpendicular to a geometrically centered axis at the ostium. The geometry of the ostium 110 may vary greatly, as described herein, for example with respect to FIG. 1. As shown in FIG. 13A, the ostium may be approximated as an oval or ellipse having a relatively shorter minor axis A1 and relatively longer major axis A2. The ostium 110 is shown as generally symmetric about the axes A1, A2, but the ostium 110 may have asymmetries, other local grooves, discontinuities, etc. Thus the ostium 110 schematic shown is merely for illustrative purposes to describe the enhanced compliance capabilities of the device 3000. In some embodiments, the minor axis A1 may refer to a maximum width of the ostium 110 in a first direction, and the major axis A2 may refer to a maximum width in a second direction. The first direction may be perpendicular to the second direction.

The lengths of the axes A1, A2 may have a variety of values or ranges of values. The minor axis A1 may be from about 5 mm to about 30 mm, from about 7.5 mm to about 20 mm, from about 10 mm to about 17.5 mm, from about 12 mm to about 15 mm, about 14 mm, or 14 mm. The major axis A2 may be from about 10 mm to about 40 mm, from about 15 mm to about 37 mm, from about 20 mm to about 35 mm, from about 22 mm to about 32 mm, from about 25 mm to about 30 mm, about 27 mm, or 27 mm.

Figure 13B:
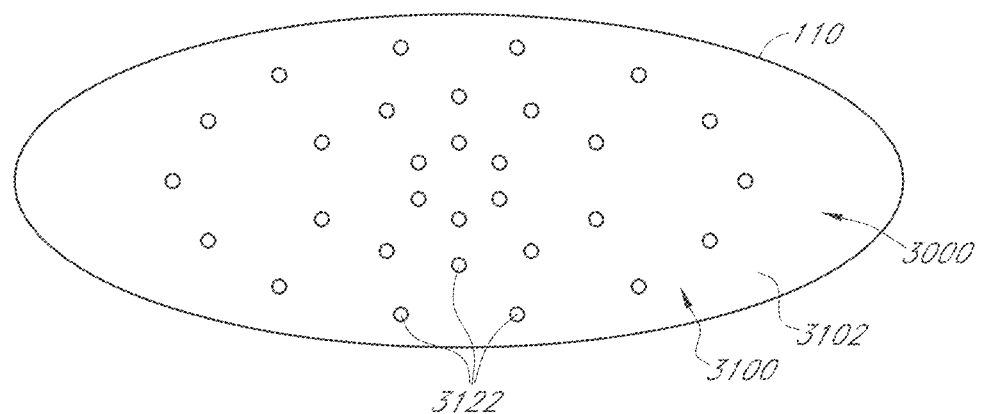
FIG. 13B is a schematic of the LAA occlusion devices of FIGS. 3A-6E as implanted in the ostium and LAA of FIG. 13A, illustrating the conforming capabilities of the devices.

FIG. 13B shows the ostium 110 from the same perspective but with the device 3000 implanted into the LAA. The cover 3100 is visible, showing the proximal surface 3102 with proximal openings 3122. Other covers as described herein may be included, such as the cover 3150, etc. The ostium in 110 with the device 3000 may have the same or similar shape and size as the ostium shown in FIG. 13A without the device 3000. The other portions of the LAA may also have the same shape and sizes before and after implantation of the device 3000. The device 3000 may therefore conform to the shape of the LAA, such as the ostium 110. The device 3000 may conform to the anatomical shape due to the configuration of the foam body 3002 and frame 3040 as described herein. The device 3000 may exhibit sufficient compliance to assume the anatomical shape to provide a sufficient occluding function and without remodeling or otherwise deforming the shape of the LAA, such as the ostium 110.

The LAA may retain the same or similar original size and shape of the LAA immediately after implantation of the device 3000 and for a period of time thereafter. In some embodiments, the anatomical geometry, for example size and shape, of the LAA will still be the same or approximately the same after implantation of the device 3000 after a period of twenty four hours or more, seven days or more, thirty days or more, six months or more, one year or more, five years or more, or longer periods. A test construct having approximately the same geometry, stiffness, etc. may be constructed to confirm the minimal long-term changes in the construct due to the device 3000. A construct having an opening with a minor axis of about 14 mm and a major axis of about 27 mm and with a stiffness generally present in normal LAA ostiums of patients may have the same or similar size and shape after implanting the device 3000 for the aforementioned periods. The device 3000 may allow for the same or similar geometry along the length of the LAA, e.g. distal to the ostium 110, for these periods of time as well, as further described.

In one example use, the device 3000 may be configured to insert into a non-cylindrical opening, having a non-cylindrical profile, of a test body. The test body may be rigid such that the test body does not deform in response to the device 3000 being implanted therein. The test body may be formed of rigid plastics, metals, etc. The opening and profile may have a size and shape substantially similar to that of a native left atrial appendage. The device 3000 may expand radially within the non-cylindrical opening, and conform to the non-cylindrical profile, which may be at least at the opening of the test body. The device 3000 may conform to the opening and have no visible gaps between the device 3000 and the opening. There may be one or more radial gaps that are each no more than five, four, three, two and/or one millimeter across at their widest portion. Such gaps may be measured radially, or perpendicularly to a longitudinal axis extending through the geometric center of the test body opening. The gap may be measured between the outer surface of the device 3000 and the inner surface of the opening of the test body. The gap may be measured at the location of maximum space between the device 3000 and the test body. The device may conform to this shape after a period of at least thirty days, at least sixty days, and/or at least one hundred twenty days after implantation. In another example use, the device 3000 may be configured to insert into a non-cylindrical opening of a test body having a size and radial stiffness substantially similar to that of a native left atrial appendage, expand radially within the non-cylindrical opening, and assume a non-cylindrical profile at least at the opening of the test body after a period of at least thirty days, at least sixty days, and/or at least one hundred twenty days.

Figure 14B:
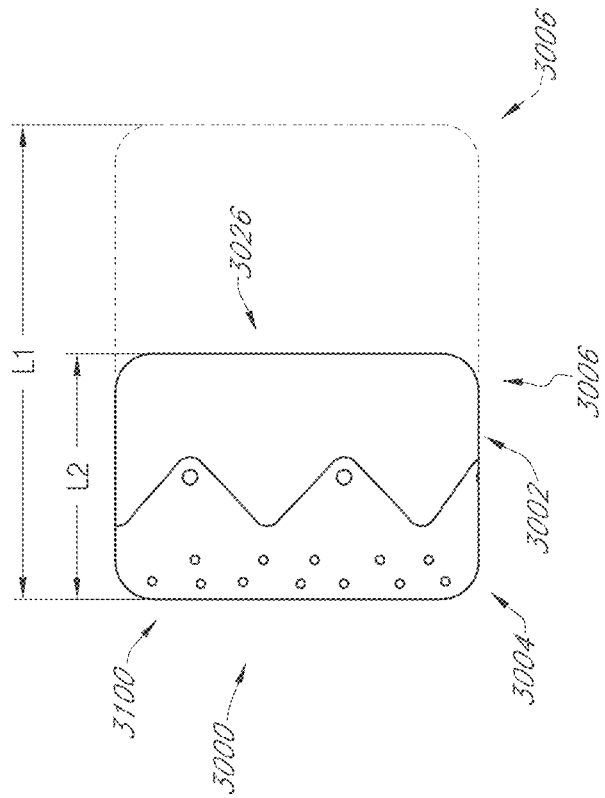
FIG. 14B is a schematic of an LAA occlusion device illustrating the axial compression capabilities of the device of FIGS. 3A-6E.
Figure 14A:
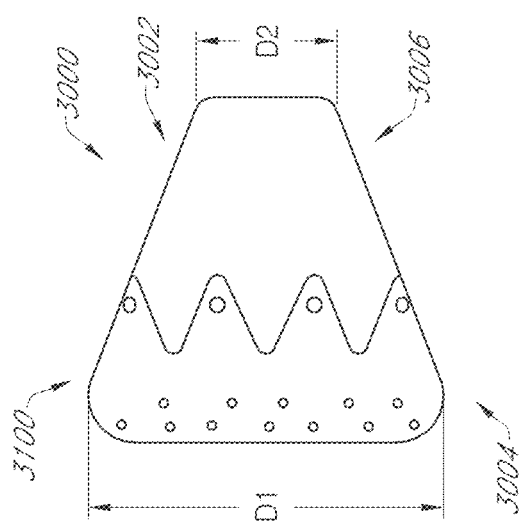
FIG. 14A is a schematic of an LAA occlusion device illustrating the radial compression capabilities of the devices of FIGS. 3A-6E.

FIG. 14A depicts a side view of the device 3000 in a radially constrained configuration. The device 3000 may have the configuration shown after implantation in the LAA, for example after the aforementioned time periods above. The device 3000 is shown with a proximal end 3004 having a width D1 and a distal end having a width D2. The widths D1, D2 may be diameters, or they may be maximum widths of the respective ends of the device 3000. The width D1 is greater than the width D2. In some embodiments, the width D1 may be less than the width D2. In some embodiments, the width D1 may be equal to or approximately equal to the width D2. In some embodiments, the width D2 may be about 15% of the width D1. The width D2 may be 95% or less, 90% or less, 85% or less, 80% or less, 75% or less, 70% or less, 65% or less, 60% or less, 55% or less, 50% or less, 45% or less, 40% or less, 35% or less, 30% or less, 35% or less, 30% or less, 25% or less, 20% or less, 19% or less, 18% or less, 17% or less, 16% or less, 15% or less, 14% or less, 13% or less, 12% or less, 11% or less, or 10% or less of the width D1. In some embodiments, the width D2 may be at other locations along the device 3000 alternatively or in addition to the distal end of the device 3000, for example a portion proximal to and adjacent or near the distal end, a middle portion of the device 3000, etc. In some embodiments, the entire device 3000 or a substantial portion of the device 3000 may have the width D2. For example, the entire device may have the width D2 when constrained within the delivery catheter, as described herein for example in the section "Loading System."

FIG. 14B depicts a side view of the device 3000 in an axially constrained configuration relative to an axially unconstrained configuration. The device 3000 has an axial length L1 in an unconstrained state, and an axial length L2 in the constrained state. The lengths L1, L2 between the proximal end 3004 and the distal end 3006 of the device 3000 in the respective configurations. The device 3000 may have the configuration shown with the length L2 after implantation in the LAA, for example after the aforementioned time periods above. The length L2 is less than the length L1. The length L2 may be 95% or less, 90% or less, 85% or less, 80% or less, 75% or less, 70% or less, 65% or less, 60% or less, 55% or less, 50% or less, 45% or less, or 40% or less of the length L1. In some embodiments, L2 may be equal to or approximately equal to L1.

In some embodiments, the bumper 3026 may allow for extreme shortening of the distal end 3006 of the device. In some embodiments, the bumper 3026 may fold inward to accommodate radial and/or axial constraining of the device 3000. The bumper 3026 may fold radially inward and/or proximally inward. Further, the compliant frame 3040 within the foam body 3002 may allow for further axial shortening beyond the length of the bumper 3026. The frame 3040 may fold radially and/or axially inward.

Further, the cylindrical shape of the device 3000 facilitates with sealing the LAA, even with atypical geometries of the LAA anatomy. The cylindrical shape ensures that the anchors are located at the locations of maximum width of the device 3000. The tubular body 3080 may provide a cylindrical foundation for the anchors 3090, 3094, as described herein, such that the anchors are located at the radially outer most portion of the device 3000. Such cylindrical shape of the device along its longitudinal axis assists with the device 3000 performing the necessary sealing, even in the constrained configurations shown in FIGS. 14A and 14B. In some embodiments, the device 3000 may be constrained both axially and radially, for example with both of the deformations shown in FIGS. 14A and 14B. The compliance of the device 3000 along with the cylindrical shape can ensure superior sealing performance compared to currently available typical LAA occlusion devices.

Figure 15:
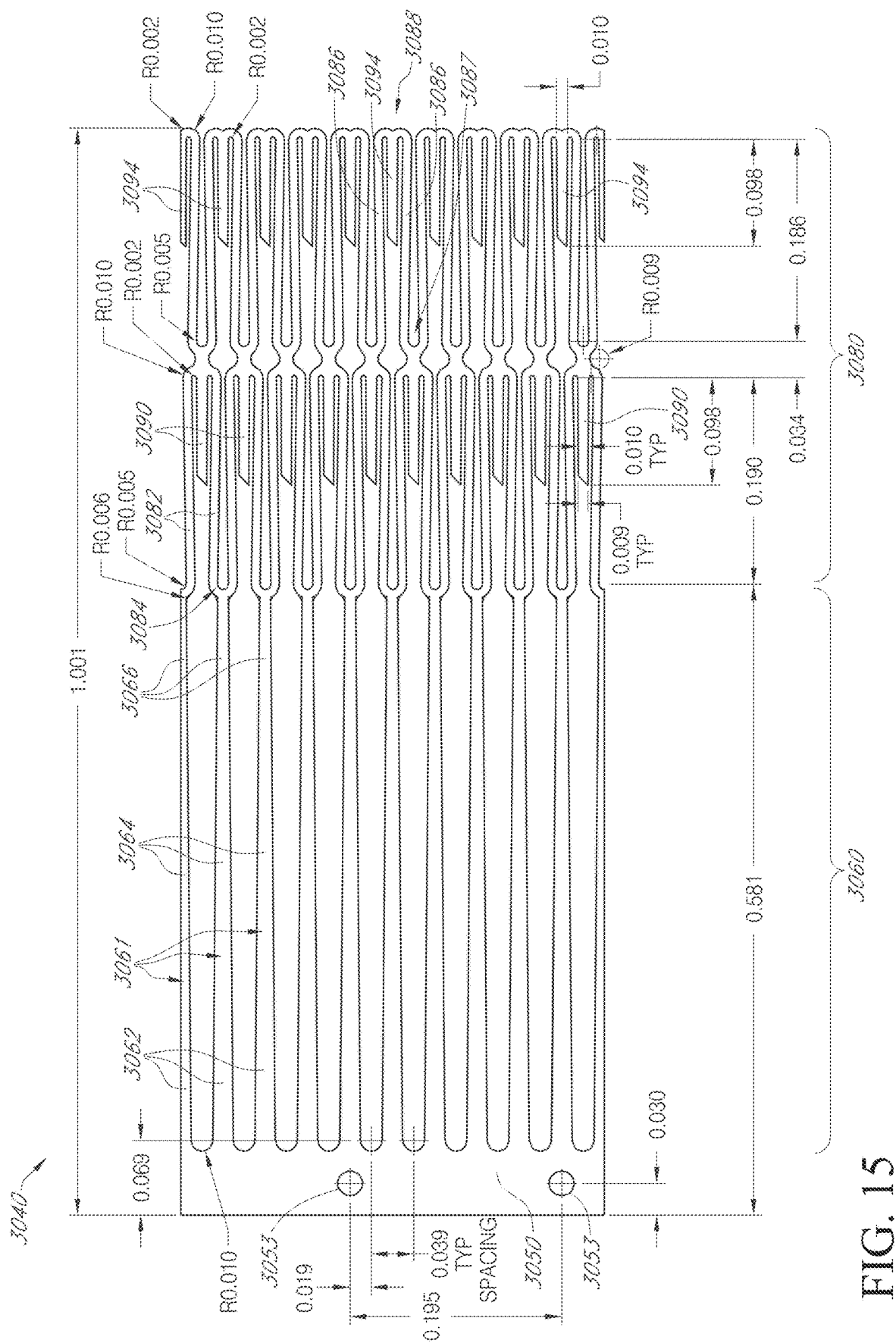
FIG. 15 is a plan view of an embodiment a laser cut tube frame shown in a flat configuration that may be used as the frame for the LAA occlusion devices of FIGS. 3A-6E.

FIG. 15 is a side view of an embodiment a laser cut tube frame 3040 shown in a flat configuration. The frame 3040 may have the various dimensions as shown in inches. The dimensions are just one embodiment and some or all dimensions may be different in other embodiments. The hub 3050 is located at a proximal end having holes 3053. The struts 3061 extend distally from the hub 3050, having curved (when assembled) proximal portions 3062, straight portions 3064, and outer curved (when assembled) portions 3066. The struts 3061 connect at proximal apexes 3084 to the proximal struts 3082. Proximal anchors 3090 extend proximally from intermediate vertices 3087. Distal struts 3086 extend from the vertex 3087 to form the distal apexes 3088, from which the distal anchors 3094 extend proximally. The frame 3040 may have approximately the dimensions shown, or they may vary therefrom. The frame 3040 shown may be used with the device 3000 having a width of 27 mm or about 27 mm.

The device 3000 provides many advantages over existing solutions to LAA occlusion, as described herein. A key advantage is that the device is highly compliant while still providing superior resistance to embolization. This unique feature of being more compliant yet better anchoring is counterintuitive. As compared to existing solutions, the device 3000 is much more conformable and thus able to take the oval shape of the LAA ostium, as described, while also providing superior dislodgement resistance, in some embodiments with a pull out force in bench testing of greater than 0.8 pounds (lbs).

12. Conformability

The device 3000 provides superior conformability to a range of different shapes and sizes of LAA's compared with existing solutions to LAA occlusion. This section further details some of the features of the device 3000 that contribute to its conformability, among other advantages. For example, some of the features described herein relate to the shape or contour of the proximal face 3060, the angular transition between the proximal face 3060 and the tubular body 3080, the lengths of the struts 3082, 3086 forming the diamond or square shapes along the tubular body 3080, and the angles of the proximal and distal apexes 3084, 3088 of the diamond or square shapes. For instance, and as further detailed herein, the frame 3040 may have a flat or substantially flat shape or contour of the proximal face 3060, a 90° or approximately 90° angular transition between the proximal face 3060 and the tubular body 3080, relatively short lengths of the struts 3082, 3086 forming the diamond or square shapes along the tubular body 3080, and relatively larger angles of the proximal and distal apexes 3084, 3088 of the diamond or square shapes.

Figure 16A:
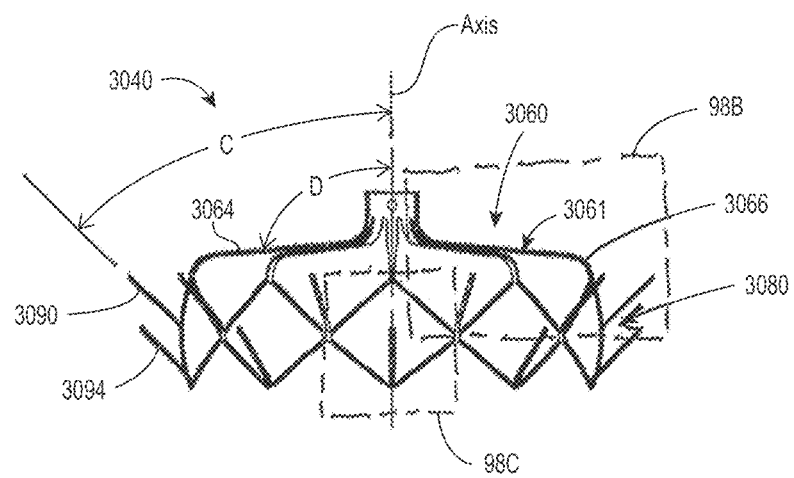
FIGS. 16A-16C are various detail views of the frame of FIGS. 7A-8C indicating some of the structural aspects contributing to the LAA occlusion device's conformable capabilities.
Figure 16B:
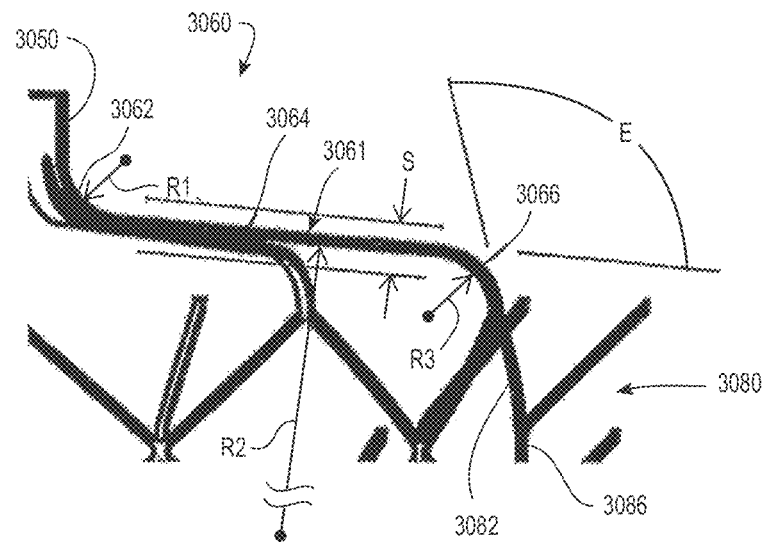
Figure 16C:
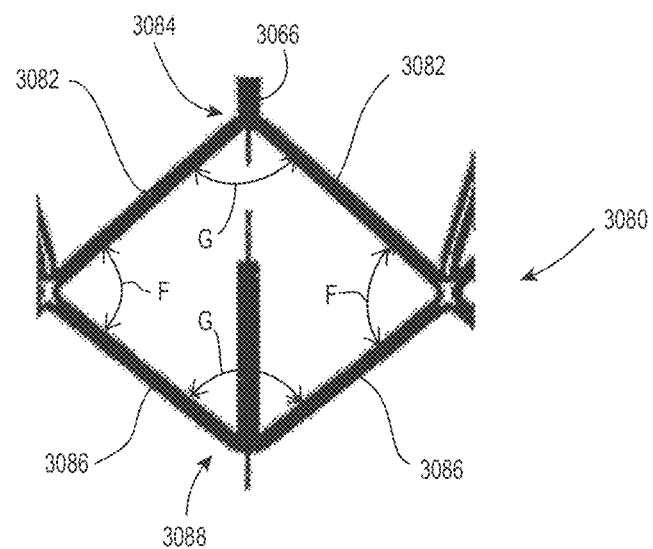

FIGS. 16A-16C are various views of the frame 3040 indicating some of the structural aspects contributing to the LAA occlusion device's 3000 conformable capabilities. FIG. 16A is a side view of the frame 3040. FIG. 16B is a detail view of a portion of the frame 3040 showing the detail region 98B as labelled in FIG. 16A. FIG. 16C is a detail view of a portion of the frame 3040 showing the detail region 98C as labelled in FIG. 16A. The frame 3040 in FIGS. 16A-16C is shown in an unconstrained configuration, for example after deployment from a delivery catheter and without any outside forces acting radially inwardly on the device frame 3040.

As shown in FIG. 16A, the frame 3040 includes the proximal face 3060 having a plurality of the proximal struts 3061, and a tubular body 3080 or "landing zone" extending distally from the proximal face 3060, between a proximal transition and a distal end. The frame 3040 includes the proximal anchors 3090 and distal anchors 3094 extending from the tubular body 3080, as described. The anchors 3090, 3094 incline radially outward in a proximal direction from the tubular body 3080.

As indicated in FIG. 16A, the anchors 3090 in an unconstrained configuration may extend at an angle C with respect to the central longitudinal axis defined by the frame 3040. The angle C may be from 25° (degrees) to 45°, about 35°, or 35°. In some embodiments, the angle C may be from 5° to 65°, from 10° to 60°, from 15° to 55°, from 20° to 50°, from 25° to 45°, or from 30° to 40°. In some embodiments, the angle C is 25°, 26°, 27°, 28°, 29°, 30°, 31°, 32°, 33°, 34°, 35°, 36°, 37°, 38°, 39°, 40°, 41°, 42°, 43°, 44°, or 45°. The distal anchor 3094 may also be inclined at any of the angles C as described with respect to the proximal anchor 3090. The distal anchor 3094 may be inclined at the same or different angle as the proximal anchor 3090. Each of the proximal anchors 3090 may be inclined at the same angle 25 as the other proximal anchors 3090, or some may be inclined at different angles as compared to others of the proximal anchors 3090. Similarly, each of the distal anchors 3094 may be inclined at the same angle as the other distal anchors 3094, or some may be inclined at different angles as compared to others of the distal anchors 3094.

The frame 3040 further includes the proximal face 3060 defined at least partially by a plurality of the proximal struts 3061, as described. The struts 3061 each include a straight portion 3064 extending radially outward and defining a line. The plurality of straight portions 3064 may extend radially outward and together define a geometric surface.

As indicated in FIG. 16A, the straight portions 3064, or the lines or surface defined thereby, in an unconstrained configuration may extend at an angle D with respect to the central longitudinal axis. The angle D may be from 85° (degrees) to 110°, about 100°, or 100°. Thus the straight portions 3064 in an unconstrained configuration may extend radially outward in a distal direction or directly radially outward. In some embodiments, the straight portions 3064 in an unconstrained configuration may extend radially outward in a proximal direction. In some embodiments, the angle D may be from 80° to 120°, from 85° to 115°, or from 95° to 105°. In some embodiments, the angle D may be greater than 90°. In some embodiments, the angle D may be greater than 80°, greater than 85°, greater than 95°, greater than 100°, greater than 105°, or greater than 110°.

The angle D is measured relative to a straight colinear extension of the part of the strut 3061, which may be or include the straight portion 3064, as mentioned. In some embodiments, the straight portion 3064 may not be perfectly straight. It may be slightly curved, have one or more curved portions therein, or not be perfectly flat, for example as further described with respect to FIG. 16B. In such cases, the angle D may be measured from a straight part of the strut 3061, if any, or the angle D may be measured from a line of best fit as determined by the straight portion 3064.

FIG. 16B shows a detail of the region 98B as indicated in FIG. 16A. As shown in FIG. 16B, the strut 3061 extends radially outward from the hub 3050 to the proximal strut 3082. The strut 3082 may be part of the tubular body 3080 or "landing zone" as described herein. In particular, the strut 3061 includes the inner curved portion 3062 extending arcuately from the hub 3050 in the distal and radially outward directions, to the straight portion 3064 extending radially outwardly, and to the outer curved portion 3066 extending arcuately in the distal direction, as described herein. The outer curved portion 3066 is connected with the proximal strut 3082 of the tubular body 3080, as described.

As indicated in FIG. 16B, the straight portion 3064 of the proximal face strut 3061 and the proximal strut 3082 of the tubular body 3080 may be angled relative to each other at an angle E. The angle E may be measured relative to the straight portion 3064, for example relative to a line, plane and/or surface defined by the straight portion 3064, as described with respect to FIG. 16A. The angle E may be measured relative to the outer surface of tubular body 3080 or portions thereof. For example, the proximal strut 3082 may extend distally along a linear or curved path, as viewed from the side. The strut 3082 is shown as curved, but it may be straight or define a line of best fit. Similarly, the distal struts 3086 of the tubular body 3080 may be curved, straight, and/or define a line of best fit, as viewed form the side. Further, the proximal and distal struts 3082, 3086 may together define a line, plane, and/or surface, as viewed from the side. For example, the tubular body 3080 may be cylindrical or generally cylindrical, as described, and thus the proximal and distal struts 3082, 3086 may together define a line, plane, and/or surface, that as viewed from the side is parallel or substantially parallel to the longitudinal axis. In some embodiments, the proximal and distal struts 3082, 3086 may together define a curved path and/or surface, that as viewed from the side initially extends distally and radially outward and then distally and radially inward, and from which a line of best fit may be determined. The angle E may thus be measured relative to any of these geometric references of the tubular body 3080.

In some embodiments, the angle E is measured relative to portions of the frame located on either side of the curved portion 3066. The proximal end of the curved portion 3066 may be attached to a radial outer end of the straight portion 3064. The angle E may be measured relative to this radial outer end of the straight portion 3064. The distal end of the curved portion 3066 reaches a transition to a proximal end of the proximal strut 3082, for example at the proximal apex 3084 as described herein and as shown in FIG. 16C. The angle E may be measured relative to this proximal end of the proximal strut 3082.

The angle E may be 90° or about 90°. In some embodiments, the angle E is from 70° to 110°, from 75° to 105°, from 80° to 100°, or from 85° to 95°. In some embodiments, the angle E is greater than 90°. In some embodiments, the angle E is greater than 70°, greater than 75°, greater than 80°, greater than 85°, greater than 95°, or greater than 100°.

Further, the inner curved portion 3062 may have a radius R1 as indicated in FIG. 16B. The radius R1 may have a proximally-facing concavity as shown, i.e. a positive or upward concavity as oriented in the figure.

The substantially straight portion 3064 may have a radius R2 to produce a distally facing concavity and proximally facing convex surface. In some embodiments, the radius R2 is infinite, where the straight portion 3064 is linear. The straight portion 3064 as shown may therefore not have a concavity, whether proximally-facing or distally-facing. In some embodiments, the straight portion 3064 may have a slight concavity proximally and/or distally. The portion 3064 may have a single concavity from inner transition to curve 3062 to outer transition 3066 without any points of inflection. The concavity may have a radius R2 of at least about 2 cm, 5 cm or 10 cm or more.

As shown, the straight portion 3064 extends radially inwardly to an inner transition to the inner curved portion 3062. The entire straight portion 3064 may therefore be located distally of the inner curved portion 3062 in the unconstrained configuration as shown. In some embodiments, the entire straight portion 3064 is located distally of a distal end of the inner curved portion 3062. In some embodiments, all portions of the strut 3061 besides the inner curved portion 3062 are located distally of the inner curved portion 3062, and there are no points of inflection along the strut portion 3064.

The straight portion 3064 may have a flatness defined by a width S as indicated in FIG. 16B. The straight portion 3064 may extend radially outward between the two parallel closest fit geometric reference lines that are separated by the width S. The width S may be the strut width, for example where the straight portion 3064 is perfectly straight. In some embodiments, the width S may be no greater than 0.2 mm, no greater than 0.3 mm, no greater than 0.4 mm, no greater than 0.5 mm, no greater than 0.6 mm, no greater than 0.7 mm, no greater than 0.8 mm, no greater than 0.9 mm, no greater than 1 mm, no greater than 1.1 mm, no greater than 1.2 mm, no greater than 1.3 mm, no greater than 1.4 mm, or no greater than 1.5 mm more than the strut width.

The outer curved portion 3066 may have a radius R3 as indicated in FIG. 16B. The radius R3 may have a distally-facing concavity as shown, i.e. a downward concavity as oriented in the figure. The radius R3 may be 1 mm or about 1 mm. In some embodiments, the radius R3 may be from about 0.2 mm to 2 mm, from about 0.3 mm to 1.8 mm, from about 0.4 mm to 1.6 mm, or from about 0.5 mm to 1.4 mm.

The radius R3 may extend along an arc having an arc length. The arc length may be measured from a first transition between a radially outward end of the straight portion 3064 to a second transition to the proximal end of the strut 3082, for example at the proximal vertex 3084 (shown in FIG. 16C, for example). This arc length may be no greater than 0.2 mm, no greater than 0.3 mm, no greater than 0.4 mm, no greater than 0.5 mm, no greater than 0.6 mm, no greater than 0.7 mm, no greater than 0.8 mm, no greater than 0.9 mm, no greater than 1.0 mm, no greater than 1.1 mm, no greater than 1.2 mm, no greater than 1.3 mm, no greater than 1.4 mm, no greater than 1.5 mm, no greater than 1.6 mm, no greater than 1.7 mm, no greater than 1.8 mm, no greater than 1.9 mm, or no greater than 2.0 mm.

FIG. 16C shows a detail of the region 98C as indicated in FIG. 16A. As shown in FIG. 16C, the quadrilateral shape defined by the struts 3082 and 3086 may define angles G and F as indicated. The angles G may be defined by the proximal and distal apexes 3084, 3088. The angles G may therefore be measured between adjacent proximal struts 3082 and between adjacent struts 3086. The two angles G may be the same or within about 2° or 4° of each other. In some embodiments, the angles G may be different for the proximal apex 3084 as compared to the distal apex 3088, for example where one or more of the struts 3082, 3086 forming the quadrilateral shape are a different length than the other struts. The angles F are defined between adjacent proximal and distal struts 3082, 3086 as indicated.

The angles G and F may each be 90° in the unconstrained configuration. In some embodiments, the angles G and F may each be approximately 90° such as within about ±1°, ±2°, ±4° or ±6° of 90°. Thus the quadrilateral formed by the struts 3082, 3086 may be a square or approximately a square. The angles G may be no less than 85°. In some embodiments, the angles G may be no less than 45°, no less than 50°, no less than 55°, no less than 60°, no less than 65°, no less than 70°, no less than 75°, no less than 80°, or no less than 90°. The sum of the four angles G and F may be 360°. Thus, the angles F may each be equal to (360°−(2×G))/2.

The quadrilateral shapes defined by the struts 3082, 3086 may define a longitudinal length between opposing apexes 3084 and 3088, for example between opposing apexes forming angles G. A longitudinal distance between a proximal apex 3084 and an opposing distal apex 3088 may be no more than 5 mm, no more than 4.5 mm, no more than 4 mm, no more than 3.5 mm, no more than 3 mm, no more than 3 mm, or no more than 2.5 mm.

The various structural aspects detailed in this section and elsewhere contributes to the enhanced conformability of the device 3000. For example, the struts 3082, 3086 of the tubular body 3080 may be mechanically independent such that applying a radially inward force on one strut of the struts 3082, 3086, or on one of the quadrilateral shapes defined by four adjacent struts 3082, 3086, does not cause the adjacent struts or quadrilateral shapes to collapse in a similar manner. Such radial force may cause the perimeter of the frame 3040 to instead bulge out. The struts 3082, 3086 may therefore behave independently which contributes to allowing the device 3000 to conform to various and extremely non-circular, for example oval, cross sectional shapes of LAA's, as further described herein, for example with respect to FIGS. 13A-13B and 17A-17B, while still providing a fully sealed and occluded LAA. In some embodiments, the device 3000 may conform to non-uniform (not circular and not oval) shapes to form a seal with non-uniform anatomy.

Further, the relatively shorter longitudinal lengths between opposing apexes 3084, 3088, the flat shape of the proximal face 3060, and the approximately 90° transition between the proximal face 3060 and the tubular body 3080 each provides enhanced conformability capabilities, as further described herein for example with respect to FIGS. 13A-13B and 17A-17B.

This conformability of the device 3000 allows the device 3000 to be sized based on the average diameter of a patient's LAA, and not the maximum diameter which is used for other existing LAA occluders. This allows a given size of the device 3000 to effectively seal a much larger range of LAA sizes, simplifying the implantation procedure and reducing costs associated with design and manufacturing.

An advantage of the device 3000 that contributes to its conformability is that when the device 3000 is compressed radially along a first, transverse axis, the average diameter remains relatively constant. As the frame 3040 is compressed to create a short, minor axis, the opposing major axis lengthens, maintaining the overall circumference or average diameter. This is in contrast to existing solutions for LAA occlusion devices, where compression of the outer diameter causes an inward collapse of the struts on the proximal side, resulting in an overall lengthening of the device in the distal and proximal directions.

Figure 17A:
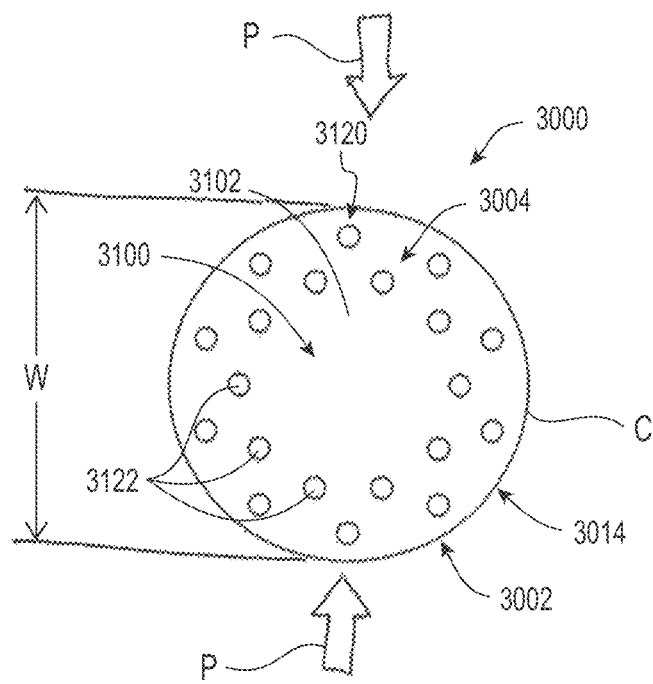
FIGS. 17A-17B are top views of the device of FIGS. 3A-6E shown, respectively, in an uncompressed configuration and a compressed configuration.
Figure 17B:
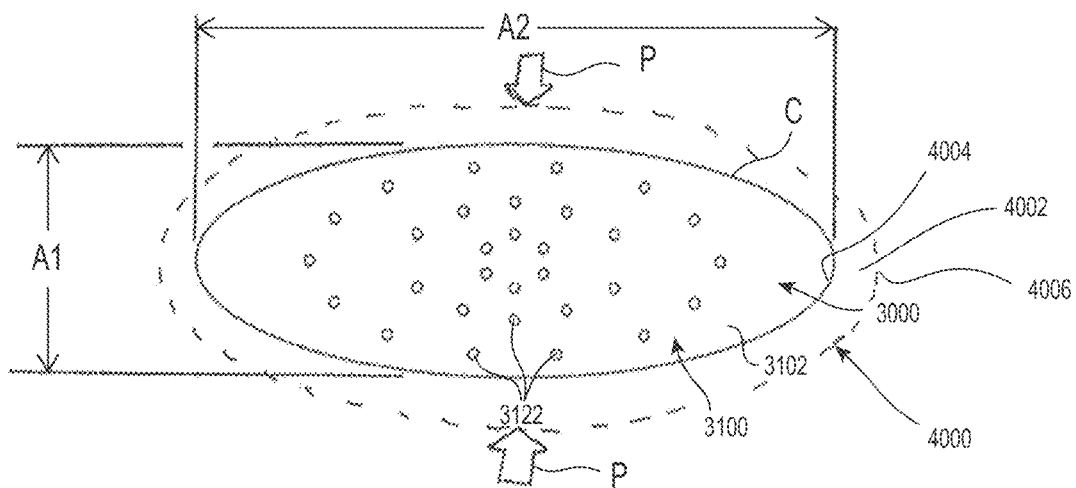

FIGS. 17A-17B are top views of the device of FIGS. 3A-6E shown, respectively, in an uncompressed configuration and a compressed configuration. The device 3000 shown may have the same or similar features and/or functions as the devices described herein, for example with respect to FIGS. 3A-6E.

FIG. 17A shows the device 3000 unconstrained prior to application of a compressive radial force P on opposing sides of the device 3000. The force P may be applied by two planar plates located on opposite sides of the device 3000. The plates may be brought together a desired distance to compress the device 3000, where the device 3000 takes an oval-like shape, such as that shown in FIG. 17B.

FIG. 17B shows the device 3000 compressed after being inserted into a collapsible tube 4000 and compressed to form a minor axis and mimic deployment within a non-cylindrical LAA. The tube 4000 has a wall 4002 with an inner surface 4004 and an outer surface 4006. The wall 4002 may extend along the longitudinal length of the device 3000. The tube 4000 may be compressed by the compressive radial forces P as shown such that the device 3000 takes the oval-like shape shown. The tube 4000 may be an elastic tube capable of compression, either by hand or by two plates as mentioned. The device 3000 may be placed into the circular tube 4000 and then the tube 4000 may be compressed. Or the tube 4000 may be pre-compressed to have the oval-like shape, and then the device 3000 may be deployed within the tube 4000 to take the pre-existing shape of the tube 4000.

The compressed device 3000 may have a minor axis A1 and a major axis A2, where the minor axis A1 is shorter than the major axis A2. As the device 3000 is compressed, A1 may decrease relative to a starting uncompressed width W (see FIG. 17A) as A2 increases relative to the starting uncompressed width W. A mean diameter "MD" may be calculated based on the resulting minor axis A1 and major axis A2. MD may be equal to (A1+A2)/2. The mean diameter MD may remain constant or relatively constant before, during and after compression. Thus the MD as calculated for the configuration in FIG. 17A (for example, where A1=A2=W) may be equal to or approximately equal to the MD as calculated for the configuration in FIG. 17B. In some embodiments, the compressed MD for the device 3000 may be within 98% or more, within 96% or more, within 94% or more, within 92% or more, within 90% or more, within 88% or more, within 86% or more, within 84% or more, within 82% or more, or within 80% or more of the uncompressed MD for the device 3000.

In some embodiments, the device 3000 may seal LAA's having widths that are larger than the uncompressed MD of the device 3000, as long as the MD of the LAA is less than or equal to the uncompressed MD of the device minus 2 mm. In other words, for this embodiment, $MD_{LAA} \leq (MD_{DEVICE} - 2 \text{ mm})$. Thus the device 3000 may be used for extreme oval shapes where the major diameter of the oval shape is larger than the uncompressed diameter of the device 3000, due to the conformable features of the device 3000. Other sizes of the device 3000 for other ranges of sizes of ostia may be similarly determined based on the MD.

As an example, the device 3000 having an uncompressed MD of 27 mm may be used to seal and anchor in a 25 mm diameter or smaller circular hole. Thus, for oval-shaped holes, the device 3000 having an uncompressed MD of 27 mm may be used to seal any oval having an MD that is less than or equal to 25 mm. For example, an oval having a major diameter of 27 mm and a minor diameter 20 mm results in an MD of 23.5 mm, which is less than or equal to 25 mm, and thus the device 3000 having an uncompressed MD of 27 mm may be used for that oval shaped ostium. As further example, an oval having a major diameter of 30 mm and a minor diameter 16 mm results in an MD of 23 mm, which is less than or equal to 25 mm, and thus the device 3000 may be used for that oval shaped ostium. As further example, an oval having a major diameter of 38 mm and a minor diameter 10 mm results in an MD of 24 mm, which is less than or equal to 25 mm, and thus the device 3000 may be used for that oval shaped ostium.

Any of the above relationships for the compressed and uncompressed MD may apply for various compressions of the device 3000 from a starting uncompressed width W, as shown in FIG. 17A. The above relationships between the compressed and uncompressed MD may apply where the device 3000 is compressed such that the compressed minor diameter A1 (shown in FIG. 17B) is no more than 90%, no more than 80%, no more than 70%, no more than 60%, no more than 50%, no more than 40%, no more than 30%, or no more than 20% of W. Thus, for example, in some embodiments, the compressed MD for the device 3000 may be within 90% or more of the uncompressed MD for the device 3000 when the device 3000 is compressed such that the compressed minor diameter A1 is less than 30% of W.

Further, the major axis A2 of the compressed device 3000 may be larger than, and in some cases much larger than, the starting width W of the uncompressed device 3000. In some embodiments, the major axis A2 may be more than 100%, more than 105%, more than 110%, more than 115%, more than 120%, more than 125%, more than 130%, more than 135%, more than 140%, more than 145% or more than 150% of W.

Further contributing to the enhanced sealing capability of the device 3000 is the behavior of the circumference of the device 3000. As shown in FIGS. 17A and 17B, the device 30 may have a circumference C as measured along a perimeter of the device 3000, which may be at or near a proximal end of the device 3000. In cylindrical embodiments, the circumference C may also be measured in other locations, for example at or near the distal end of the device 3000, or between proximal and distal ends.

The circumference C, as measured at a given longitudinal point along the length of the device 3000, may be the same or approximately the same in the uncompressed and compressed configurations, for example in the configurations of FIG. 17A and FIG. 17B respectively. In some embodiments, the circumference C of the compressed device 3000 may be within 1%, within 2%, within 3%, within 4%, within 5%, within 6%, within 7%, within 8%, within 9%, within 10%, or within 15% of the circumference C of the uncompressed device 3000 measured at the same longitudinal transverse plane. Such relationships for the compressed and uncompressed circumferences may apply along with any of the other described relationships herein, such as the relationships between A2 and W, between A1 and W, and/or between the compressed MD and uncompressed MD.

The above relationships of the device 3000 may be tested using the plates (for example a vice) or tube as shown and described with respect to FIGS. 17A and 17B, respectively. For example, the device 3000 having a 27 mm diameter (width W) may be placed in a metal vice submerged within a body temperature saline bath. The vice may be initially set with an opening of 25 mm. The vice may then be closed to discrete distances between the plates. At each measurement point, the minor axis A1 (equal to the opening of the vice) and major axis A2 of the compressed device 3000 may be determined. The mean diameter MD may be calculated based on the determined lengths A1 and A2. The circumference may be measured, or otherwise determined based on known geometric equations for calculating a circumference based on A1 and A2.

Another feature of the device 3000 that contributes to the enhanced sealing capability is the foam body 3002. The foam material of the body 3002 has a stiffness that may naturally bow radially outward, as opposed to collapsing inwards like the existing prior art devices that have polyester or ePTFE fabric which can "scallop" to form outward concavities between struts which may cause residual leaks. In contrast, the device 3000 has foam in the body 3002 which provides more stiffness and shape memory than knitted or woven polyester fabric or the like, contributing to the device's 3000 ability to conform to the irregular geometry of the interior surface of the LAA and thereby provide a better seal.

The device 3000 may also apply less of a radial outward force on the LAA while providing a superior seal, as compared to existing LAA occlusion devices. Thus the device 3000 may provide a "softer" solution for LAA occlusion devices. The radial stiffness of the device, which is an indication of the radial outward force the device 3000 would apply to an LAA, may be tested. For example, the device 3000 may be compressed, for example using the vice discussed in connection with FIG. 17A and/or a compressive force gauge, to measure the applied force. The applied force may then be compared to the resulting change in the width W of the device 3000 due to the applied force. In some embodiments, the required force in pounds (lbs) to compress the device 3000 a distance of D in inches (in) may be within 20%, within 15%, within 10%, or within 5% of F, where $F=0.23 D+0.04$.

Figure 18A:
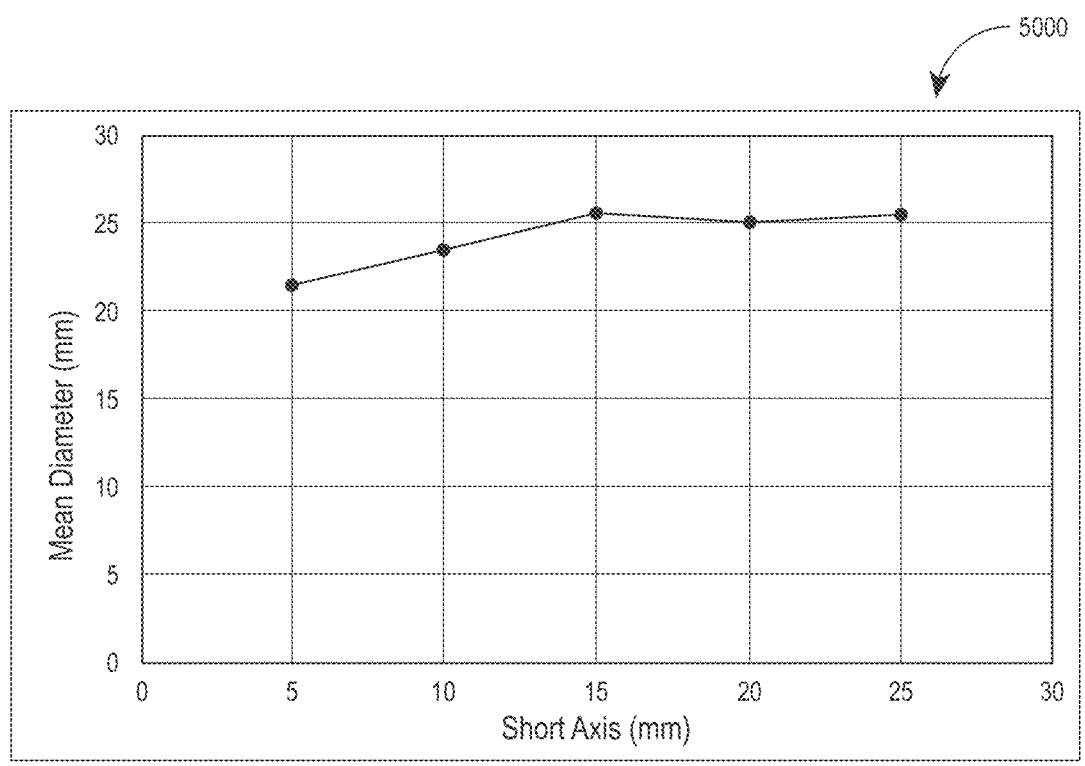
FIGS. 18A-18C are data plots of test results showing various structural characteristics for certain embodiments of the device of FIGS. 3A-6E.
Figure 18B:
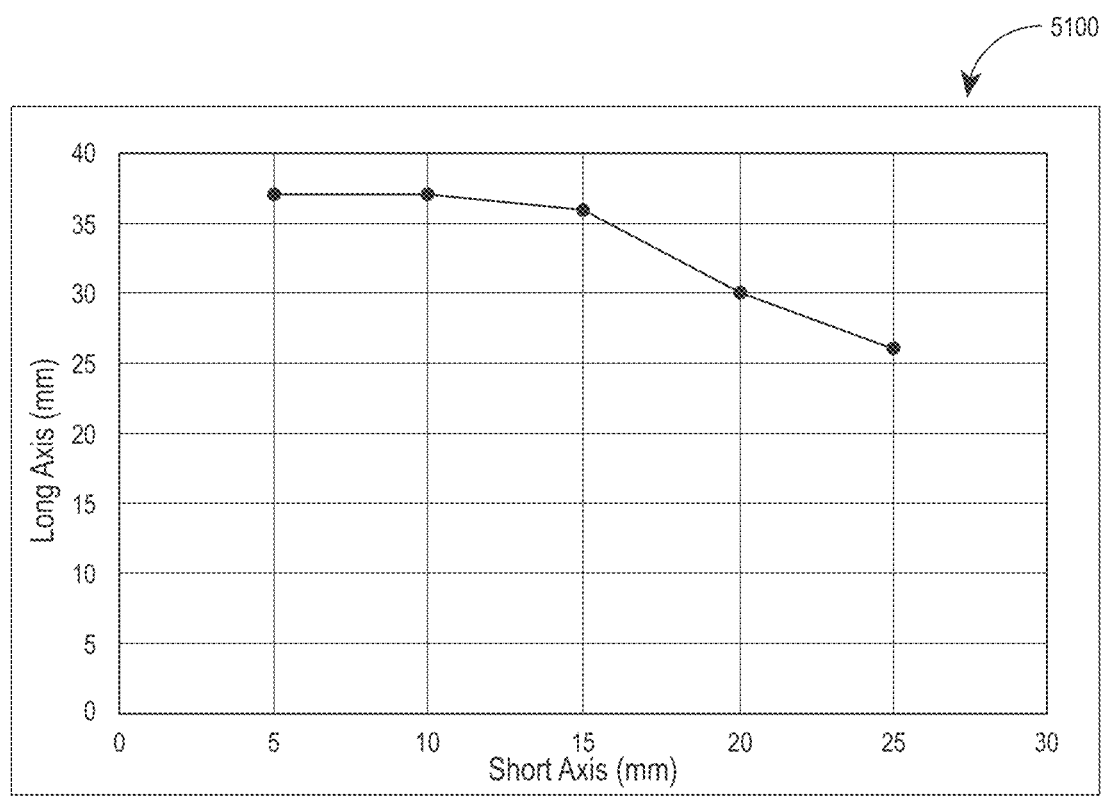
Figure 18C:
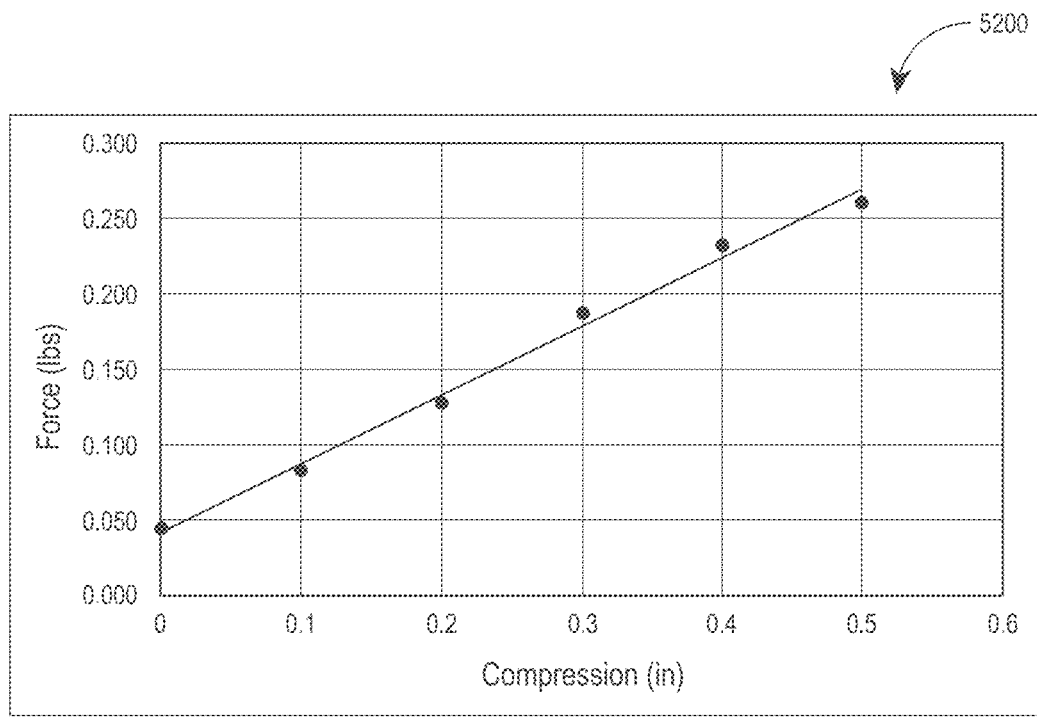

FIGS. 18A-18C are data plots 5000, 5100, 5200 respectively of test results showing various structural characteristics for certain embodiments of the device of FIGS. 3A-6E. FIG. 18A shows the data plot 5000 for the relationship between the mean diameter MD of the device 3000 (on the Y axis) and the minor diameter A1 or "short axis" of the device 3000 (on the X axis). FIG. 18B shows the data plot 5100 for the relationship between the major diameter A2 or "long axis" of the device 3000 (on the Y axis) and the minor diameter A1 or "short axis" of the device 3000 (on the X axis). FIG. 18C shows the data plot 5200 for the relationship between an applied compressive force to the device 3000 (on the Y axis) and the decrease in the width W of the device or "compression" (on the X axis).

As the minor axis is compressed by 10 mm from an unconstrained diameter such as from 25 mm (in an unconstrained 25 mm device, or at a starting diameter of 25 mm in a larger device) to 15 mm, the mean diameter has a reduction of no more than about 5 mm, and preferably no more than about 3 mm or 2 mm or 1 mm or less. As the minor axis is compressed by 15 mm such as from 25 mm to 10 mm, the mean diameter has a reduction of no more than about 8 mm, and preferably no more than about 6 mm or 4 mm or 3 mm or less. As the implant is compressed from an unconstrained configuration starting diameter to a minor axis diameter that is 15 mm less than the starting diameter, the mean diameter has a reduction of no more than about 10 mm and in some implementations no more than about 8 mm or 6 mm or 4 mm or 3 mm or 2 mm or less, depending in part upon the starting diameter.

Referring to FIG. 18B, reduction of the short axis by 10 mm such as from 25 mm (unconstrained) to 15 mm produces an elongation of the major axis of at least about 2 mm and in some implementations at least about 4 mm or 6 mm or 8 mm or 10 mm or more. Reduction of the short axis by 20 mm such as from 25 mm (unconstrained) to 5 mm produces an elongation of the major axis of at least about 2 mm and in some implementations at least about 4 mm or 8 mm or 10 mm or more, enabling the implant to conform to a wide variety of non cylindrical LAA configurations.

Referring to FIG. 18C, Application of 0.10 lbs compressive force produces a compression along the minor axis of at least about 0.05 inches or 0.10 inches or 0.20 or more. Application of 0.20 lbs compressive force produces a compression along the minor axis of at least about 0.15 inches or 0.20 inches or 0.25 inches or 0.30 inches or 0.40 inches or more. Application of no more than about 0.37 lbs or 0.33 lbs. or 0.30 lbs or 0.27 lbs or less compressive force produces a compression along the minor axis of at least about 0.35 inches or 0.40 inches or 0.45 inches or 0.50 inches or more to produce a soft and conformable implant.

The foregoing relationships can be scaled and converted to a percent basis to apply to implants having an unconstrained expanded diameter that differs from 25 mm.

Figure 19A:
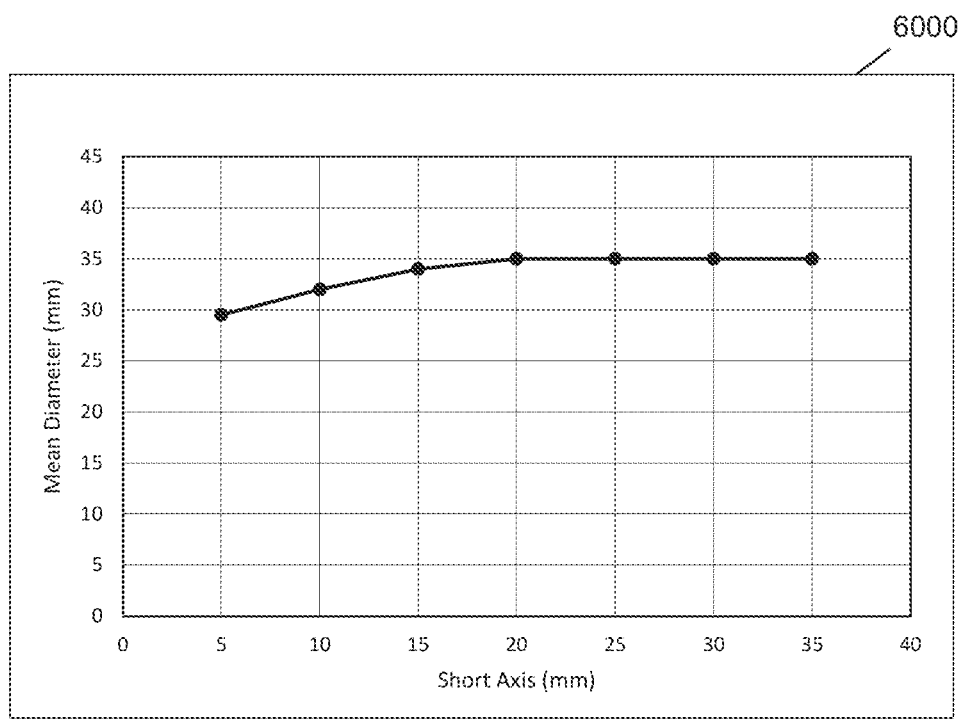
FIGS. 19A-19C are data plots of test results showing various structural characteristics for certain other embodiments of the device of FIGS. 3A-6E
Figure 19B:
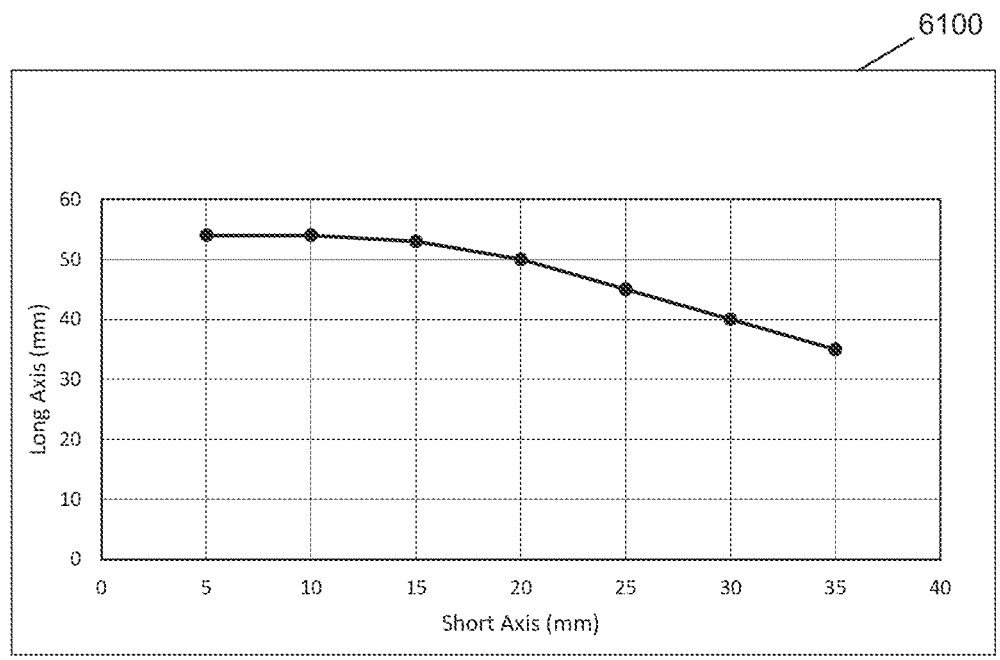
Figure 19C:
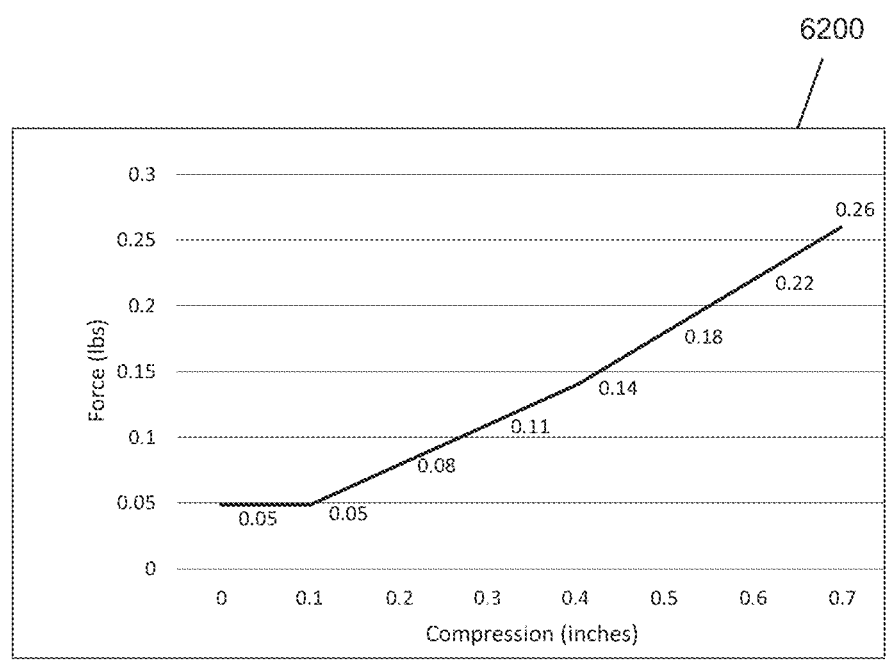

FIGS. 19A-19C are data plots 6000, 6100, 6200 respectively of test results showing various structural characteristics for embodiments of the device of FIGS. 3A-5E having an unconstrained outer diameter of 35 mm. FIG. 19A shows the data plot 6000 for the relationship between the mean diameter MD of the device 3000 (on the Y axis) and the minor diameter A1 or "short axis" (under compression) of the device 3000 (on the X axis). FIG. 19B shows the data plot 6100 for the relationship between the major diameter A2 or "long axis" (under compression) of the device 3000 (on the Y axis) and the minor diameter A1 or "short axis" of the device 3000 (on the X axis). FIG. 19C shows the data plot 6200 for the relationship between an applied compressive force to the device 3000 (on the Y axis) and the decrease in the width W of the device or "compression" (on the X axis).

Table 2 below lists the compression data points from FIG. 19A along with the corresponding maximum or major diameter (Dmax), corresponding to certain embodiments of the device 3000 having a 35 mm unconstrained outer diameter.

TABLE 2

| Dmin (mm) | Dmax (mm) | Dmean (mm) |
|---|---|---|
| 35 | 35 | 35 |
| 30 | 40 | 35 |
| 25 | 45 | 35 |
| 20 | 50 | 35 |
| 15 | 53 | 34 |
| 10 | 54 | 32 |
| 5 | 54 | 29.5 |

As shown in FIG. 19A and in Table 2, as the minor axis is compressed by 10 mm from an unconstrained diameter such as from 35 mm (in an unconstrained 35 mm device, or at a starting diameter of 35 mm in a larger device) to 25 mm, the mean diameter has a reduction of no more than about 5 mm, and preferably no more than about 3 mm or 2 mm or 1 mm or less. As the minor axis is compressed by 15 mm such as from 35 mm to 20 mm, the mean diameter has a reduction of no more than about 5 mm, and preferably no more than about 3 mm or 2 mm or 1 mm or less. As the minor axis is compressed by 20 mm such as from 35 mm to 15 mm, the mean diameter has a reduction of no more than about 5 mm, and preferably no more than about 3 mm or 2 mm or 1 mm or less. As the minor axis is compressed by 25 mm such as from 35 mm to 10 mm, the mean diameter has a reduction of no more than about 8 mm, and preferably no more than about 6 mm or 4 mm or 3 mm or less. As the minor axis is compressed by 30 mm such as from 35 mm to 5 mm, the mean diameter has a reduction of no more than about 15 mm and in some implementations no more than about 12 mm or 10 mm or 8 mm or 6 mm or 5.5 mm or less.

Referring to FIG. 19B, reduction of the short (minor) axis by 10 mm such as from 35 mm (unconstrained) to 25 mm produces an elongation of the long (major) axis of at least about 2 mm and in some implementations at least about 4 mm or 6 mm or 8 mm or 10 mm or more. Reduction of the short axis by 15 mm such as from 35 mm (unconstrained) to 20 mm produces an elongation of the major axis of at least about 4 mm and in some implementations at least about 6 mm or 8 mm or 10 mm or 12 mm or 14 mm or 15 mm or more. Reduction of the short axis by 20 mm such as from 35 mm (unconstrained) to 15 mm produced an elongation of the major axis of at least about 6 mm and in some implementations at least about 8 mm or 10 mm or 12 mm or 14 mm or 16 mm or 18 or more. Reduction of the short axis by 25 mm such as from 35 mm (unconstrained) to 10 mm produced an elongation of the major axis of at least about 6 mm and in some implementations at least about 8 mm or 10 mm or 12 mm or 14 mm or 16 mm or 18 or 19 or more. Reduction of the short axis by 30 mm such as from 35 mm (unconstrained) to 5 mm produced an elongation of the major axis of at least about 6 mm and in some implementations at least about 8 mm or 10 mm or 12 mm or 14 mm or 16 mm or 18 or 19 or more, enabling the implant to conform to a wide variety of non cylindrical LAA configurations.

Referring to FIG. 19C, for some embodiments of the 35 mm unconstrained outer diameter device, application of 0.10 lbs compressive force produces a compression along the minor axis of at least about 0.05 inches or 0.10 inches or 0.20 inches or 0.25 inches or more. Application of 0.20 lbs compressive force produces a compression along the minor axis of at least about 0.45 inches or 0.40 inches or 0.45 inches or 0.50 inches or 0.55 inches or more. Application of no more than about 0.37 lbs or 0.33 lbs. or 0.30 lbs or 0.26 lbs or less compressive force produces a compression along the minor axis of at least about 0.5 inches or 0.55 inches or 0.6 inches or 0.65 inches or more to produce a soft and conformable implant.

The foregoing relationships can be scaled and converted to a percent basis to apply to implants having an unconstrained expanded diameter that differs from 35 mm.

Table 3 includes test results showing various structural characteristics for certain embodiments of the devices of FIGS. 3A-6E. Table 3 illustrates the results of a visual evaluation of a seal between certain embodiments of the device of FIGS. 3A-6E and a Silicon (Si) test tube in which the tube includes a visible amount of fluid, the device is placed inside the tube, and the tube and device are then placed under compression.

TABLE 3

| Dmin (mm) | Dmax (mm) | Dmean (mm) | Seal |
|---|---|---|---|
| 33 | 33 | 33 | Sealed |
| 30 | 35 | 32.5 | Sealed |
| 25 | 38 | 31.5 | Sealed |
| 20 | 40 | 30 | Sealed |
| 15 | 44 | 29.5 | Not Sealed |

With respect to Table 3, an unconstrained 35 mm device was placed within a Si tube having an internal diameter of 33 mm and compressed. As the minor axis is compressed by 3 mm so that the mean diameter is between 33 and 30 mm, a seal is present between the device and the Si tube. As the minor axis is compressed so that the major axis is between 33 mm and 40 mm, a seal is present between the device and the Si tube. In some embodiments, the 35 mm device can seal in oval openings with a mean diameter of 33 mm or 32 mm or less and a maximum diameter of 40 mm or less. In some embodiments, the device can seal in non-uniform (not round or oval) openings. "Seal" as used in this context includes visual verification of no drops of fluid located behind the device inside the tube. The seal may also include devices tested as described above with escape of fluid having a volume of 5 ml or 4 ml or 3 ml or less when the tube with the device inside is held upside down, with the fluid above the device, for a time period of 15 seconds or 30 seconds or 1 minute or 2 minutes or more. The fluid may be saline, water, or combinations thereof.

Figure 20:
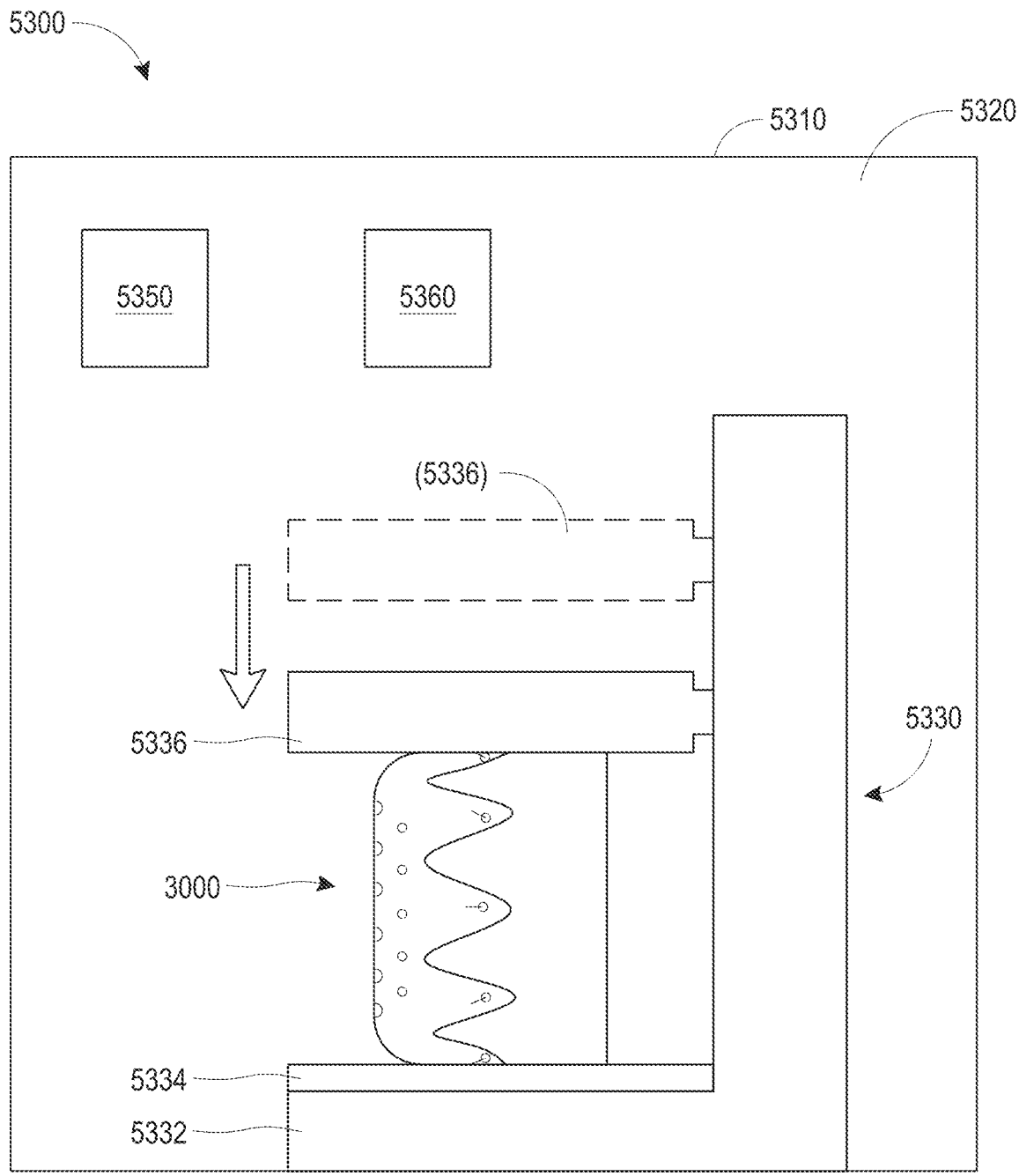
FIG. 20 is a schematic of an embodiment of a test setup that may be used to perform a flat plate test to characterize the stiffness and other structural attributes of the device of FIGS. 3A-6E.

FIG. 20 is a schematic of an embodiment of a test setup 5300 that may be used to perform a flat plate test method, such as described herein, to characterize the stiffness and other structural attributes of the device 3000. The data plots 5000, 5100, 5200, 6000, 6100, and 6200 in FIGS. 18A-19C and the data of Tables 2 and 3 may be generated using the test setup 5300. The data of Table 3 may be generated using the test setup 5300 with the device 3000 positioned within an Si tube. The test setup 5300 may thus be used for determining whether a given occlusion device exhibits the same or similar structural characteristics as the device 3000.

As shown in FIG. 20, the test setup 5300 includes a volume 5310, which may be a bath. The volume 5310 contains water 5320. The water 5320 may partially or completely fill the volume 5310. A thermal conditioner 5350, such as heating or cooling device, may be used to heat or cool the water to the desired temperature. A recirculator 5360, such as a pump, may be used to recirculate the water to provide a uniform distribution of temperature in the water.

The test setup 5300 further includes a mechanical press 5330. The press 5330 may be a compression test stand. A variety of suitable compression test apparatuses known in the art may be used for the press 5330. The press 5330 may be submerged, partially or completely, in the water 5320. The press 5330 may be a vertical press as shown. A horizontal arrangement may be used. The press 5330 may have a graduated scale or scales. The press 5330 includes a lower plate 5332 having a force gage 5334 thereon. The force gage 5334 may instead be located on an upper plate. The force gage 5334 detects a compressive force and provides output indicative of the compressive force applied to the gage 5334. The gage 5334 may be fitted with or include a flat surface for applying compression to the device 3000. The occlusion device 3000 is shown located on top of the force gage 5334, with an upper moveable plate 5336 located above the device 3000. In some embodiments, the force gage 5334 may be located on top of the device 3000, for example on an underside (as oriented in the figure) of the upper plate 5336.

The upper plate 5336 is lowered from the position shown by dashed outline to contact the upper side of the device 3000 (as oriented in the figure) to the current location of the upper plate 5336 shown in solid line in the figure. The upper plate 5336 may be lowered farther to compress the device 3000. The resulting compressive load as registered by the force gage 5334 as the upper plate 5336 is lowered may be recorded and plotted. The resulting plot of force versus amount of compression of the device 3000 may be the same or similar as the data plot 5200 shown in FIG. 18C or the plot 6200 shown in FIG. 19C. In some embodiments, the resulting data plot using the test setup 5300 may be within +/−5%, +/−10%, +/−15%, +/−20% or +/−25% of the data points or line of best fit shown in FIG. 18C.

The test setup 5300 may also be used to measure or approximate dimensions of the device 3000 as the device 3000 is compressed. As described herein, for example with respect to FIGS. 17A-17B, the minor and major axes of the device 3000 may be measured. The test setup 5300 may have dimensions located on the setup 5300 showing vertical and horizontal scales for determining the lengths of the major and minor axes of the device 3000 as the device 3000 is compressed. In some embodiments, a separate measurement device, such as a ruler, may be used to measure the lengths. The resulting plot of minor (short) axis versus major (long) axis of the device 3000, or parameters related thereto such as the mean diameter, may be the same or similar as the data plots 5000 and 5100 show respectively in FIGS. 18A-18B and the plots 6000 and 6100 shown respectively in FIGS. 19A-19B. In some embodiments, the resulting data plots using the test setup 5300 may be within +/−5%, +/−10%, +/−15%, +/−20% or +/−25% of the data points or lines of best fit shown in FIGS. 18A-18B or 19A-19B.

Figure 21:
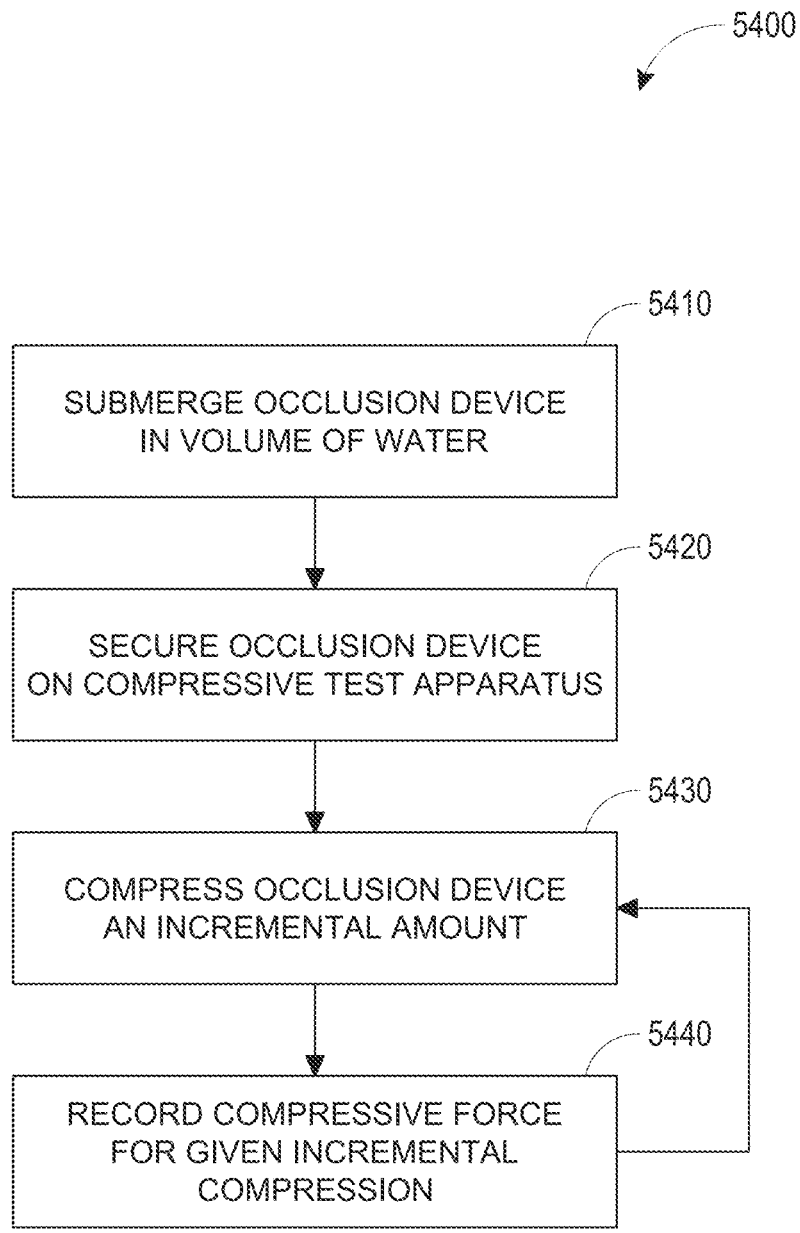
FIG. 21 is a flow chart depicting an embodiment of a flat plate test method that may be performed with the test setup of FIG. 20 and the device of FIGS. 3A-6E.

FIG. 21 is a flow chart depicting an embodiment of a flat plate test method 5400. The method 5400 may be performed using the test setup 5300. The method 5400 may be performed to characterize the stiffness and other structural attributes of the device 3000. The data plots 5000, 5100, 5200, 6000, 6100, and 6200 in FIGS. 18A-19C and the data of Tables 2 and 3 may be generated using the method 5400. The method 5400 may thus be used for determining whether a given embodiment of an occlusion device exhibits the same or similar structural characteristics as the device 3000.

The method 5400 begins with step 5410 wherein the device 3000 is submerged in a bath or other volume of water, such as the volume 5310 having the water 5320. The device 3000 may be submerged and placed onto a lower test plate, such as the lower plate 5332 having the force gage 5334. The device 3000 may be submerged within the volume for a sufficient amount of time to equilibrate to the temperature within the volume of water. In some embodiments, the device 3000 may be submerged for one minute. In some embodiments, the device 3000 may be submerged for two, three, four, five or more minutes. The volume of water may be at a temperature of 37° C. (98.6° F.). The method 5400 may be performed at or near sea-level, or otherwise under sea-level conditions (e.g. sea-level atmospheric pressure). A thermometer may be used to determine the temperature at or near the device 3000. A water heater and/or water recirculator, such as the thermal conditioner 5350 or recirculator 5360, and/or other tools, may be used to achieve the desired temperature.

The method 5400 next moves to step 5420 wherein the device is secured on the compressive test apparatus, such as the test setup 5300. The device 3000 may be placed and secured between the compressive test plates of the test setup. The distance between the two plates may be reduced. The upper plate 5336 may be lowered to contact and secure the device 3000 between the two plates. The upper plate 5336 may be lowered as shown in FIG. 20 to contact a side of the device 3000. The initial compressive load on the device 3000 may be measured and recorded with just enough contact from the upper plate 5336 on the device 3000 to hold the device 3000 in position. This may be about 0.05 lbs.

The method 5400 next moves to step 5430 wherein the device 3000 is compressed an incremental amount by reducing the distance between the plates an incremental amount. The upper plate 5336 may be lowered a first increment to compress the device 3000 radially inwardly. The upper plate 5336 may be moved 0.10". In some embodiments, a larger or smaller compressive increment may be used.

The method 5400 next moves to step 5440 wherein the resulting compressive force for the given incremental compression is measured and recorded. Thus the compressive load may be measured with the upper plate having been lowered 0.10" in step 5400.

The method 5400 may next return to step 5430 and compress the device 3000 another incremental amount, after which step 5440 may be performed again to record the corresponding compressive load. Steps 5430 and 5440 may be repeated until a desired amount of compression is obtained. In some embodiments, steps 5430 and 5440 may be repeated at compressive increments of 0.10", 0.20", 0.30", 0.40", and 0.50". In some embodiments, the order of steps 5430 and 5440 as shown in FIG. 21 may be reversed. For example step 5440 may include applying a specified load (e.g. 0.05 lbs., 0.1 lbs., 0.15 lbs., 0.2 lbs., 0.25 lbs.) and step 5430 may include measuring the resulting compressive change in width, if any, of the device 3000 under each incremental given load. The method 5400 in this manner may be repeated for each incremental applied load.

The method 5400 may be repeated with the device 3000. The device 3000 may be rotated an angular amount and the method 5400 may be performed again. This may be repeated several times after completing the method 5400 as described. For example, the method 5400 may be performed a first time, then the device 3000 may be rotated in first direction about its longitudinal axis sixty degrees, then the method 5400 may be repeated, then the device 3000 may be rotated in the first direction about the longitudinal axis another sixty degrees, and the method 5400 may be repeated. The load measurements during repeated tests at different angular amounts may be averaged for a given compression amount at a particular angle. In some embodiments, the averages of three measurements may be calculated, after initially testing the device 3000 and then rotating the device 3000 by sixty degrees twice as described, and the resulting plot may be the same or similar as the data plot 5200 shown in FIG. 18C or the data plot 6200 shown in FIG. 19C. In some embodiments, the resulting data plot using the averages may be within +/−5%, +/−10%, +/−15%, +/−20% or +/−25% of the data points or line of best fit shown in FIG. 18C or FIG. 19C.

B. Loading Tool with Ribs, Submersion, and Catheter Locking

Figure 22A:
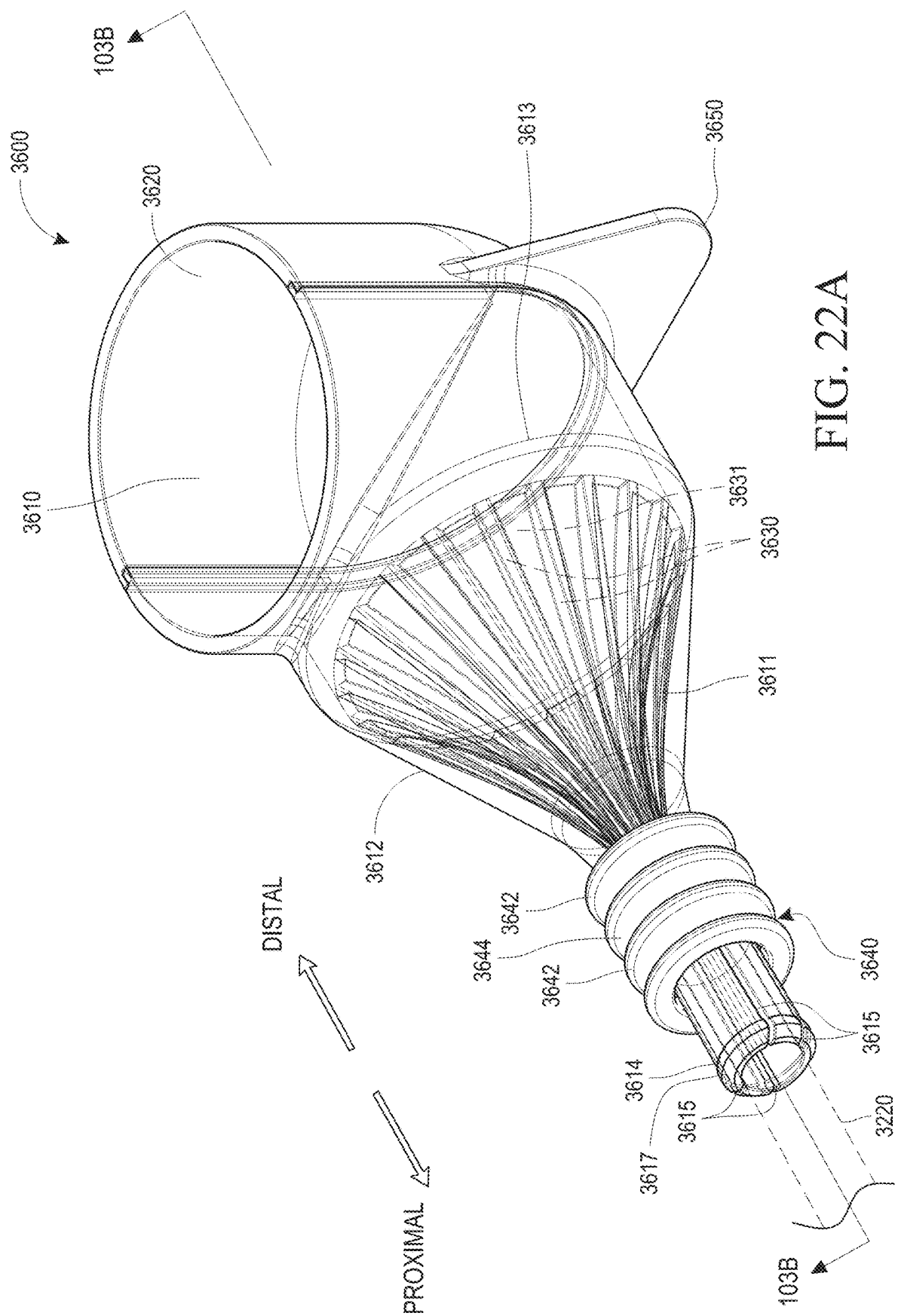
FIGS. 22A and 22B are perspective and cross-section views, respectively, of an embodiment of a loading tool having guides, a locking connection for securing a catheter, and configured to hold fluid.
Figure 22B:
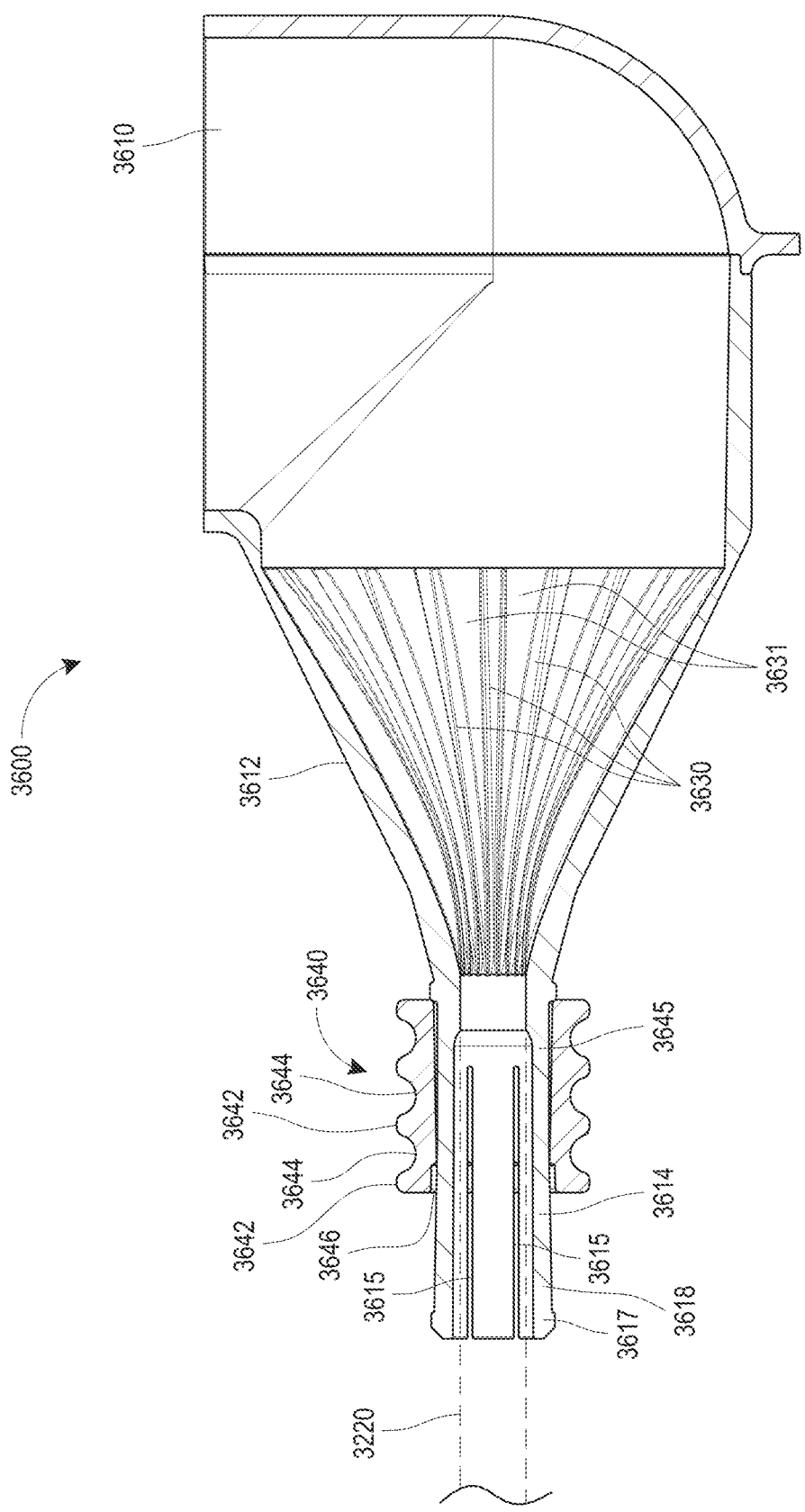

FIGS. 22A and 22B are perspective and cross-section views, respectively, of an embodiment of a loading tool 3600. The cross-section view of FIG. 22B is taken along the line 103B-103B as indicated in FIG. 22A. The loading tool 3600 may have the same or similar features and/or functions as other loading tools described herein, such as the loading tool 3210, and vice versa. The loading tool 3600 may be used with any of the embodiments of the LAA implant and related devices and systems described herein, such as the device 3000, and vice versa.

As further described herein, the tool 3600 includes radially inwardly projecting ribs forming grooves therebetween, which among other things improves implant folding and helps align the barbs. Further, the tool 3600 includes a locking connection between the loader and catheter, to provide among other things a seal and eliminate gaps while assuring alignment (e.g., to prevent implant damage). Further, the tool 3600 is configured to hold fluid, so that among other things the implant can be fully submerged during loading, thus eliminating air bubbles from within the foam.

The loading tool 3600 includes a distal reservoir 3610 attached to a conical portion 3612. A proximal projection 3614 attaches at a proximal end of the conical portion 3612. The device 3000 is placed into the reservoir 3610 and pulled through the conical portion 3612 and then the projection 3614. A delivery catheter is attached at the projection 3614 so that the device 3000 is constrained and delivered to the delivery catheter for implantation into the patient. For clarity, the reservoir 3610, the conical portion 3612, and the projection 3614 are shown as transparent in FIG. 22A.

The conical portion 3612 includes ribs 3611. The loading tool 3600 may include a plurality of internal guides such as at least four or ten or twenty or more axially oriented ribs 3611. The ribs 3630 are formed between adjacent internal grooves 3631 formed on the inner surface of a conical portion 3612. In one implementation, the grooves 3631 have a substantially constant width along their axial lengths, resulting in ribs 3611 having a width that increases in the distal direction as the inside diameter of the conical portion 3612 increases. The ribs 3630 may be longitudinally elongated, radially inwardly projecting structures located along the radially inwardly facing surface of the conical portion 3612. Between adjacent ribs 3630 the may be one of the internal grooves 3631 defined partially by the adjacent ribs 3611 and the inner surface of the conical portion 3612. The ribs 3630 improve implant folding and help align the anchors 3090, among other advantages. Such alignment may be through the foam sidewall of the implant, for example where the anchors 3090 press against the foam sidewall and occupy the grooves 3631 between the ribs 3611. In some embodiments, some or all of the anchors 3090 may protrude through the foam sidewall of the implant to contact and be directly guided by the grooves 3631 and ribs 3630. For clarity only some of the ribs 3611 and grooves 3631 are labelled in the figures.

The conical portion 3612 terminates at the distal end at a conical portion opening 3613. The opening 3613 may open into the fluid reservoir 3610. The fluid reservoir 3610 has a distal opening 3620 and an outwardly extending support flange 3650. In some embodiments the location of the support flange 3650 may be different. The flange 3650 may extend outward in two opposite directions. The flange 3650 may secure the tool 3600 in an upright position on a table top for loading. The fluid reservoir 3610 may be defined within a housing having the distal opening 3620 and one or two or more stabilizing feet such as the transverse support flange 3650 for helping the loading tool 3600 to sit upright on a counter surface.

The reservoir 3610 is designed to hold fluid (e.g., saline) with the device 3000 also located therein so the implant can be fully submerged during loading, thus eliminating air bubbles from within the foam. In some embodiments the fluid reservoir 3610 may have a tubular, e.g., cylindrical side wall, with a closed base which incorporates a ramp such as a quarter-spherical portion to facilitate entry of the implant from the reservoir 3610 into the opening 3613.

The distal opening 3620 of the fluid reservoir 3610 allows the device 3000 to be inserted into the loading tool 3600. The reservoir 3610 is configured to receive the device 3000 therein, and the device 3000 may be oriented therein such that the proximal end of the device 3000 faces the conical portion 3612 and a sidewall of the device 3000 faces the proximal opening 3620 of the tool 3600. For clarity, the tool 3600 in FIGS. 22A and 103B is shown without the device 3000 loaded therein.

The projection 3614 includes a sidewall 3618 that extends longitudinally away from the proximal end of the conical portion 3612 and defines a channel therethrough configured to receive a distal end of the delivery catheter therein. "Distal end" of the catheter here refers to the end of the catheter in the delivery context, where the distal end is advanced to the heart. The projection 3614 at a proximal end thereof includes a radially outwardly protruding lip 3617. The lip 3617 projects outward and has a greater outer radius than the sidewall 3618. The sidewall 3618 includes a series of longitudinal notches 3615. There are four notches 3615 as shown, but there may be two, three, five, six, or more notches 3615. The notches 3615 extend distally from the proximal end of the projection 3614.

The loading tool 3600 may also include a lock 3640. In FIGS. 22A-22B the delivery catheter 3220 is shown as a dotted line for clarity. A proximally extending projection 3614 of the loading tool is configured to abut against or fit inside of the distal opening into the lumen of the delivery catheter to facilitate transfer of the implant. At least one or two or three or more axially extending slits 3615 through the sidewall 3618 of the projection 3614 allow the inside diameter of the projection 3614 to adjust slightly in response to radial force from the compressed implant. The lock 3640 may include a sliding collar for sealing and aligning with the distal end of the delivery catheter 3220. The collar is axially movable between a distal position as seen in FIG. 22A to expose the proximal projection 3614 for mounting within the delivery catheter, and a proximal position in which it overlaps over the outside surface of the delivery catheter sidewall to reversibly support the connection. The lock may include grooves 3644 and ridges 3642 to provide a friction surface and improve user handling. The collar is configured to slide concentrically over the cylindrical portion 3614 and lock the delivery catheter 3220 between the projection 3614 and the collar. In some embodiments the projection 3614 may be cylindrical or a shape other than cylindrical.

In some embodiments, the lock 3640 may be a sliding cylindrical structure surrounding the projection 3614, for sealing and aligning the catheter 3220. The lock may include outer grooves 3644 defined between adjacent radially outwardly protruding ridges 3642. For clarity only some of the ridges 3642 and grooves 3644 are labelled in the figures. The lock 3640 includes an inner channel 3645 extending longitudinally therethrough and defined by the sidewall of the lock 3640. At a proximal end of the channel 3645 is a relatively wider opening 3646. The opening 3646 is configured to surround the lip 3617 of the projection 3614 when the lock 3640 is slid to the proximal end of the projection 3614.

In some embodiments, in a free state, where the lock is in the distal location as shown in FIGS. 22A and 22B, the projection 3614 has a wider inner diameter relative to the diameter when inward compressive forces are applied, so that the catheter can be easily inserted. The lock 3640 may then be slid proximally with the catheter inside the projection 3614. The lock 3640 in a proximal location will cause the portions of the sidewall 3618 located adjacent the notches 3615 to move circumferentially closer to each other and to compress radially inwardly, to thereby reduce the inner diameter defined by the sidewall 3618. The catheter tip will then be "sandwiched" by the inner surfaces of the sidewall 3618 to create radially inward securement forces acting on the catheter tip to secure the catheter. The opening 3646 may contact and secure therein the lip 3617 of the projection 3614 when the lock 3640 is slid to the proximal end of the projection 3614. The inner diameter of the opening 3646 may be the same or less than the outer diameter of the lip 3617, for example to create a compressive force thereon.

In some embodiments, in a free state, the outer surface of the sidewall 3618 may be tapered such that the outer surface has a greater outer width, e.g. radius or diameter, at a proximal end thereof (left end as oriented in the figures) as compared to a distal end thereof (right end as oriented in the figures). The lock 3640 may then be moved proximally and contact the outer surfaces of the sidewall 3618 to thereby decrease the inner diameter of the sidewall 3618, as described. The lock 3640 is advantageous to provide a seal and eliminate gaps while assuring alignment of the catheter 3220 to the loading tool 3600, among other advantages. For example, the seal, alignment and gap reduction serve to reduce the chance of the implant being damaged during loading. The tool 3600 and components thereof may be made of plastic, polymer, metal, other suitable materials, or combinations thereof.

C. Delivery Catheter Handle

Figure 23A:
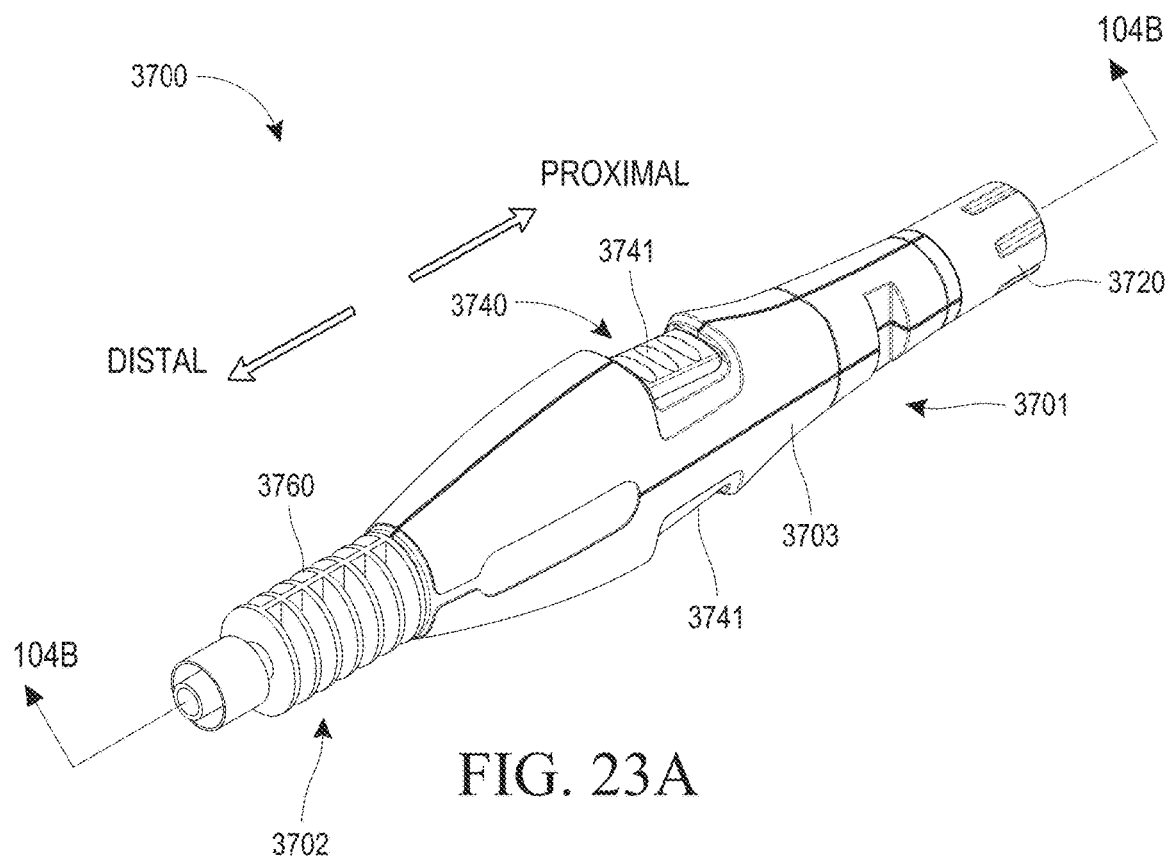
FIGS. 23A-23D are various views of an embodiment of a delivery catheter handle that may be used with the LAA implant and associated devices and systems described herein.
Figure 23B:
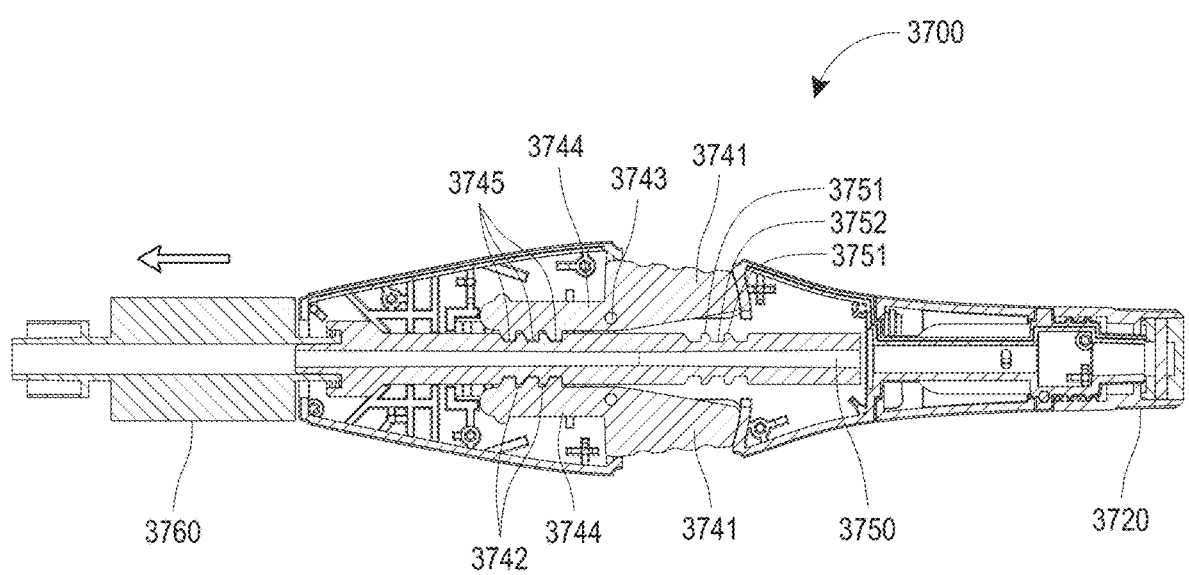
Figure 23C:
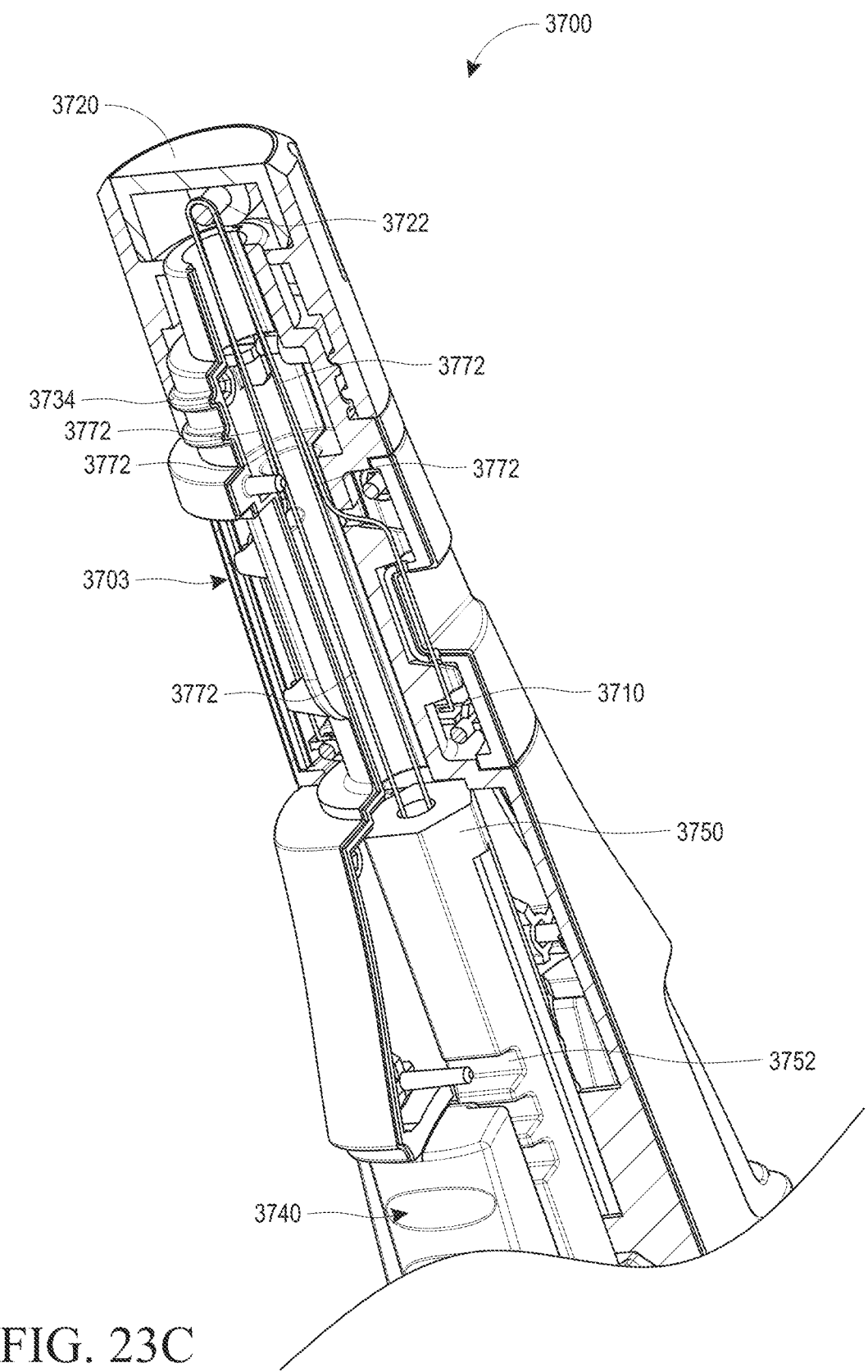
Figure 23D:
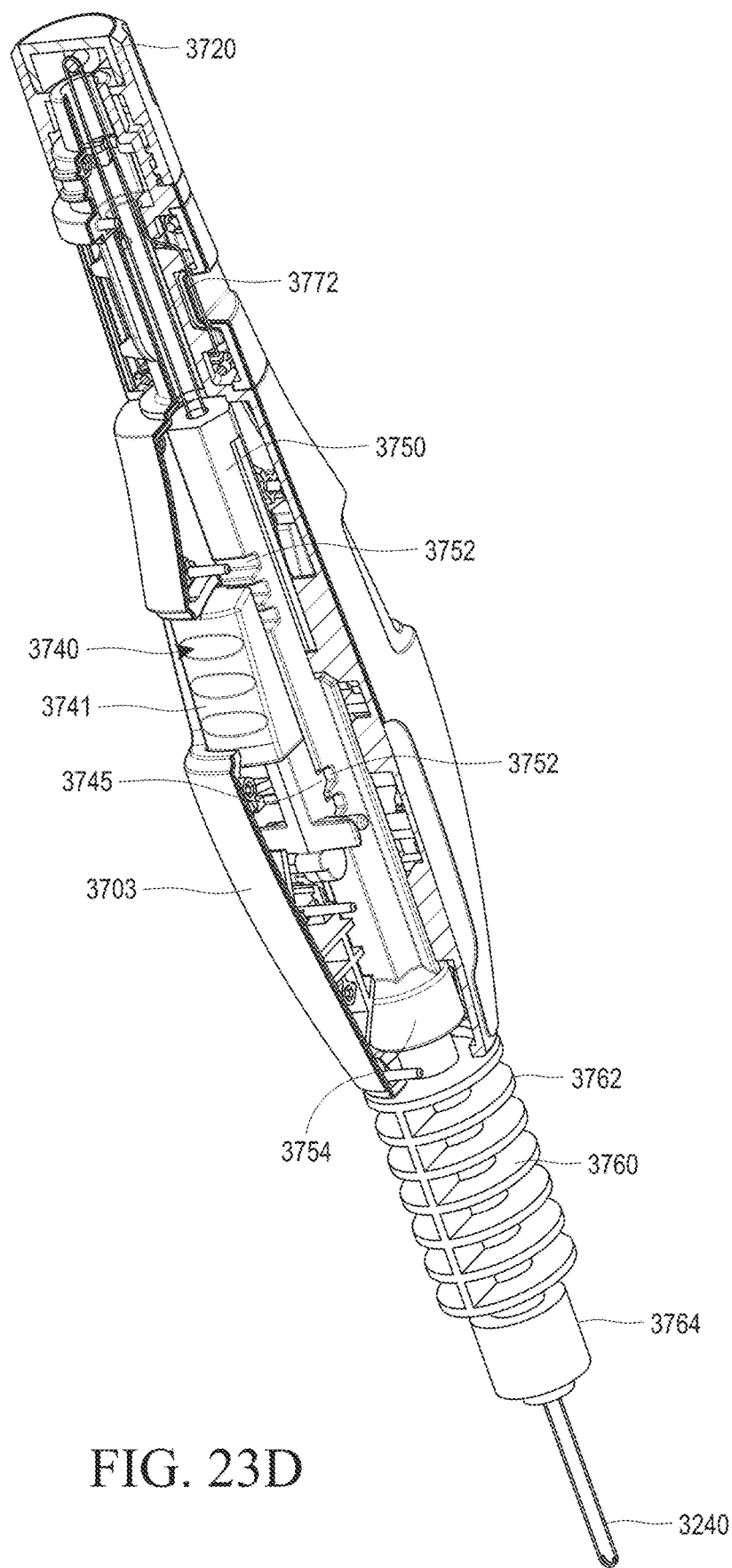
Figure 26:
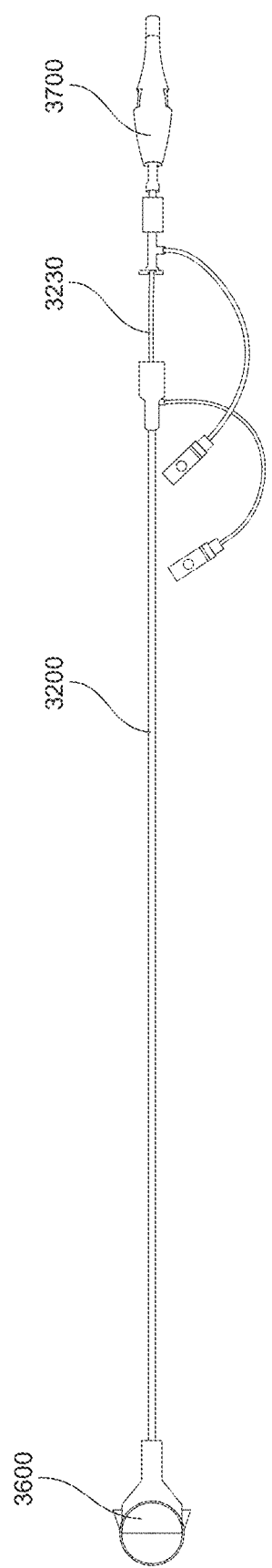
FIG. 26 is a side view of a catheter delivery system that may be used with the various occlusion devices described herein.

FIGS. 23A-23D depict an embodiment of a delivery catheter handle 3700. FIG. 23A is a perspective view, FIG. 23B is a cross-section view as taken along the line 104B-104B indicated in FIG. 23A, FIG. 23C is a detailed partial cross-section view, and FIG. 23D is a partial cross-section view of the handle 3700. The handle 3700 may be used with the various LAA implants and associated devices and methods described herein. For example, the handle 3700 may be used to deliver the device 3000. The loading tool 3600 may be used to load the device 3000 into a delivery catheter, which then may be used with the handle 3700 to deliver and secure the device 3000 within the human body. FIG. 26 depicts an embodiment of a delivery system comprising the delivery catheter handle 3700, the loading tool 3600, the delivery catheter 3220, and the pusher 3230.

The handle 3700 extends from a proximal end 3701 to a distal end 3702. A main body 3703 attaches at a proximal end to a cap 3720 and at a distal end to a ribbed body 3760. The ribbed body 3760 may be a tether control switch 3780, as described with respect to FIGS. 24A-24C. The cap 3720 attaches to a tether 3772 (see FIGS. 23C-23D) and can be secured, for example screwed, to the proximal end of the body 3703. Unsouring, for example unscrewing, the cap 3720 allows for the tether 3772 to be pulled proximally after implantation of the device 3000, to remove the tether from the delivery catheter. The tether 3772 may have the same or similar features and/or functions as other tethers or sutures described herein, for example the tether 3240, and vice versa. For clarity, the tether 3772 is not shown in FIG. 23B.

A locking mechanism 3740 includes a button 3741 that when depressed allows for axial movement of an internal shaft 3750. When released, the button 3741 is spring-loaded via a pivot arm 3744. Each arm 3744 pivots about a pin 3743. There may be a torsion spring at each pin 3743 that bias the two arms 3744 toward the shaft 3750. The shaft 3750 may be in the distal location as shown during implantation of the device 3000 and then moved proximally after implanting the device 3000 in the LAA, so that the pusher and/or delivery catheter can likewise be moved proximally prior to releasing the device 3000 from the tether 3000. This removes the "snap back" effect of removing a pusher and/or delivery catheter from contacting LAA occlusion devices right after implantation in the LAA, in which the occlusion device may move slightly due to the backing off of the pusher.

The shaft 3750 locks in with the arms 3744 via protrusions 3745 on the arm 3744, such as teeth, extending inwardly away from each arm 3744 and forming lateral grooves between adjacent protrusions 3745. Corresponding lateral protrusions 3742 on the shaft 3750 extend outwardly away from the shaft 3750. The protrusions 3742 of the shaft 3750 are received into grooves between corresponding protrusions 3745 of the arms 3744 when the shaft 3750 is in the proximal position as shown. When the shaft 3750 is advanced axially distally, the protrusions 3745 are received into grooves 3752 defined by protrusions 3751 at a proximal end of the shaft 3750.

A tether 3772, or suture, travels through the handle 3700 and wraps around a pin 3722 in a manner that incorporates a pulley-like effect so the tether 3772 only has to be pulled half the distance of the length of the catheter during removal. The need to pull a suture the entire length of the catheter during removal is one of the disadvantages of using a suture as an attachment tether. This modification makes it less burdensome and more appealing to the user.

The handle 3700 may be configured to enable an operator to easily remove the tether 3772 from a patient. Specifically, during removal, the operator pulls the end cap portion 3720 proximally while holding the body 3703 fixed relative to the patient. As the cap 3720 moves proximally away from the body 3703, the tether 3772 feeds over the pin 3722. Since the tether 3772 is fixed to the body 3703 at a tether end 3710, all of the four tether segments 3772 elongate. The tether end 3710 may be secured to the body 3703 or other components therein in a variety of suitable manners, for example screwed, bonded, wrapped, other suitable approaches, or combinations thereof. The outcome of this elongation is that the tether 3772 portions inside the patient body translate twice as far as the cap 3720 translates. This phenomena is similar to a movable pulley arrangement used in reverse. The net effect of the system is to halve the applied force and double the length of the tether 3772 pulled. This reversed movable pulley arrangement is advantageous to reduce the pulled distance and applied force required to remove the tether 3772 from the patient, so the retraction of the tether from the patient may be at least about two times or four times or more the length of retraction of the proximal control. This makes the removal less arduous and time consuming for the operator.

The system arrangement includes, in some embodiments, a pulley in the form of the pin 3722, on which the tether 3772 is wrapped. The pin moves relative to the tether end 3710. Various embodiments are possible wherein the pin 3722 moves relative to the tether end 3710. Various such embodiments result in a pulley-like effect to reduce the total motion required to remove the tether 3772 from the patient. An arrangement with the pin 3722 and tether end 3710 is effective to reduce the total tether pull distance requirement by half.

In the example embodiment depicted in FIGS. 23A-23D, the cap 3720 is threaded onto the proximal end 3734 of the body 3703. The locking mechanism 3740 is coupled to the side of the body 3703, as described. The locking mechanism 3740 may include protrusions 3745 and can actuate to lock into the notches 3752 disposed on the inner shaft 3750. The inner shaft 3750 is fastened at the distal end 3754 to the ribbed body 3760, or in some embodiments to the tether control switch 3780 (shown in FIGS. 24A-24C). The ribbed body 3760 has a ribbed region 3762 and a cylindrical portion 3764. The tether 3772 extends through a central hole disposed through both the ribbed body 3760 and the inner shaft 3750. The body 3760 may be replaced with a tether control switch, such as a switch 3780 as described herein, for example with respect to FIGS. 24A-24C.

In the depicted embodiment, the notches 3752 interface with the protrusions 3742 when the locking mechanism 3740 is in the locked position. In the locked position, the relative positions of the inner shaft 3750 and the outer body 3730 are fixed. The locking mechanism 3740 can be actuated to allow relative motion between the inner shaft 3750 and the outer body 3750, as described.

Figure 24A:
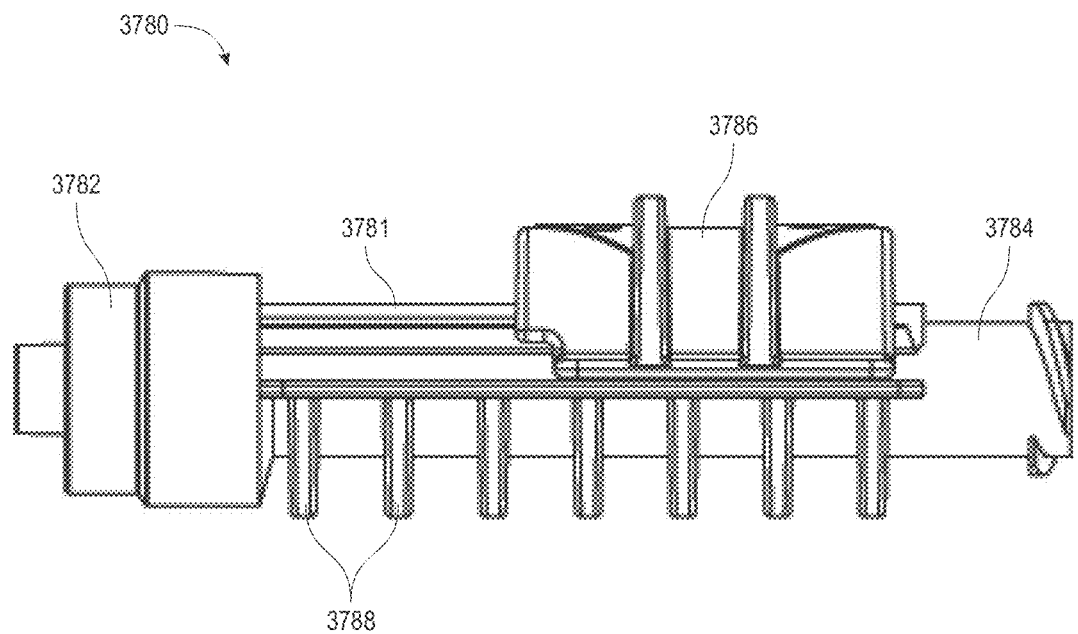
FIGS. 24A-24D are various views of an embodiment of a tether control switch or components thereof that may be used with the various LAA implant delivery handles, such as the handle of FIGS. 23A-23D, and associated devices and systems, described herein.
Figure 24B:
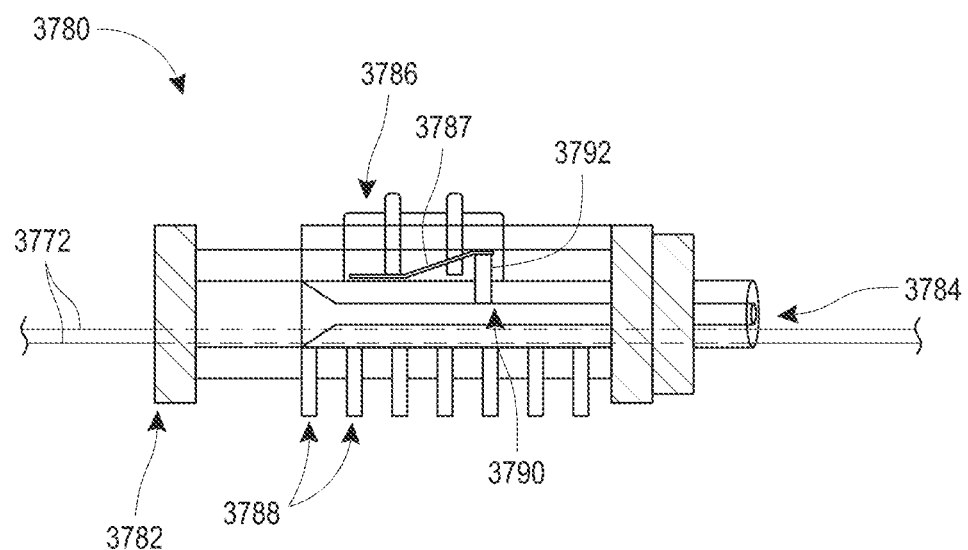
Figure 24C:
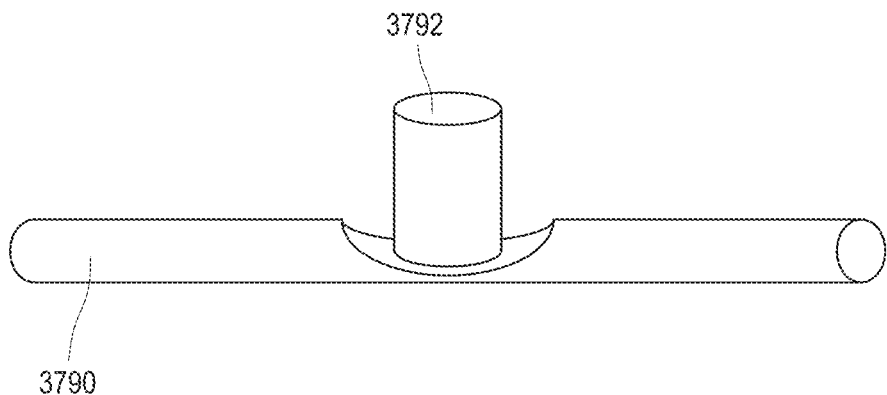
Figure 24D:
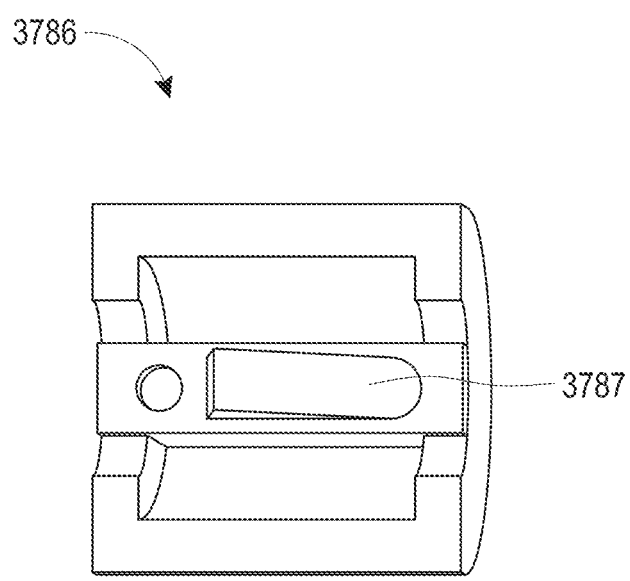

FIGS. 24A-24D are various views of an embodiment of a tether control switch 3780 that may be used with the various LAA implant delivery handles, such as the handle 3700 of FIGS. 23A-23D, and associated devices and systems, described herein. FIG. 24A is a side view, FIG. 24B is a partial side cross-section view, FIG. 24C is a partial view of some components of the switch 3780, and FIG. 24D is a bottom view of a slider 3786 used with the switch 3780.

The switch 3780 includes a body 3781 extending longitudinally from a proximal end 3784, that attaches to the delivery handle, to a distal end 3782 that receives the tether and the delivery catheter therein. A series of outwardly protruding grips 3788 extend outwardly away from the body 3781 for gripping the device. There may be seven grips 3788 as shown, or fewer or greater than seven grips 3788. The grips 3788 may be held by a user while a slider 3786 is moved axially along the body 3781.

The slider 3786 moves axially to selectively engage and disengage the tether 3772. As shown, in the proximal position (right as oriented), the slider 3786 is not engaged with the tether 3772, such that the tether can freely move through the switch 3780. When the slider 3786 is moved to the distal position (left as oriented), the slider 3786 is engaged with the tether 3772, such that the tether cannot freely move through the switch 3780. The switch 3780 includes a compression tube 3790 and pill 3792 to effectuate the engagement/disengagement of the tether 3772 via the slider 3786.

As shown in FIGS. 24B-24D, the slider 3786 has an inner ramped surface 3787 that is located farther from the longitudinal central axis of the switch 3780 at a proximal end and closer to the axis at a distal end. As the slider 3786 is moved proximally, the ramped surface 3787 applies an increasing force to the pill 3792, which then compresses the tube 3790 onto the tether 3772. The slider 3786 may be locked at the proximal and/or distal positions, for example to maintain the freedom or restriction of the movement of the tether 3772 therethrough. In some embodiments, the orientation of the ramped surface 3787 may be flipped to be in an opposite direction, such that the inner ramped surface 3787 is located farther from the longitudinal central axis of the switch 3780 at a distal end and closer to the axis at a proximal end. The tube 3790 may be formed of a foam or other compressible material. The pill 3792 may be relatively more rigid so as to transfer the force from the slider 3786 to the tube 3790. Further, with the tube 3790 compressed, fluid may be prevented from flowing through the switch 3780.

D. Dual Lumen Pusher

Figure 25A:
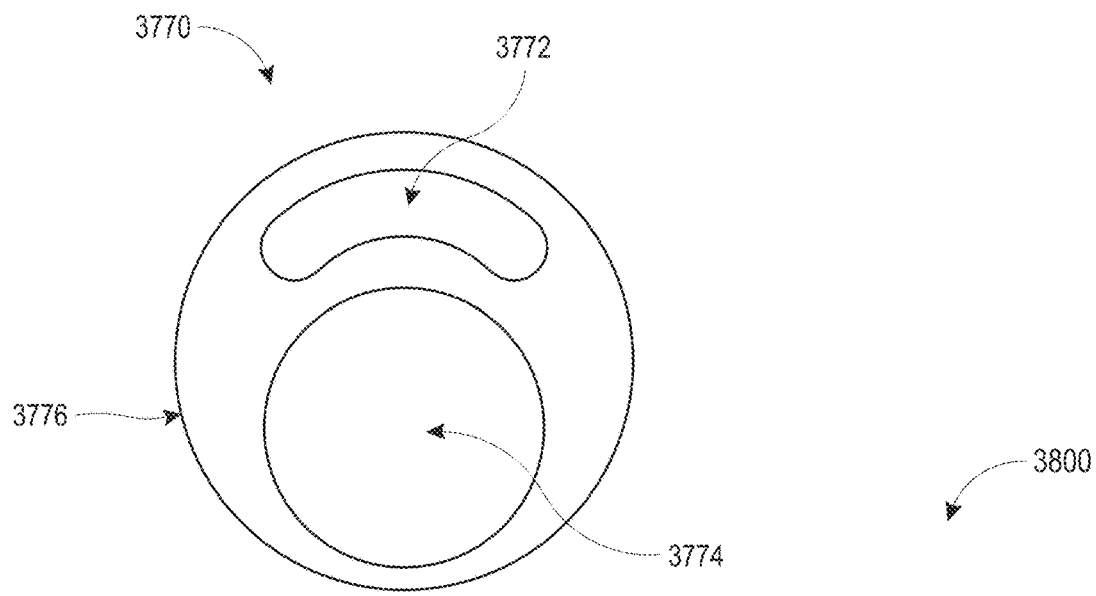
FIGS. 25A-25C show various views of various embodiments of dual lumen delivery catheter pushers that may be used with the various delivery systems and implants described herein.
Figure 25B:
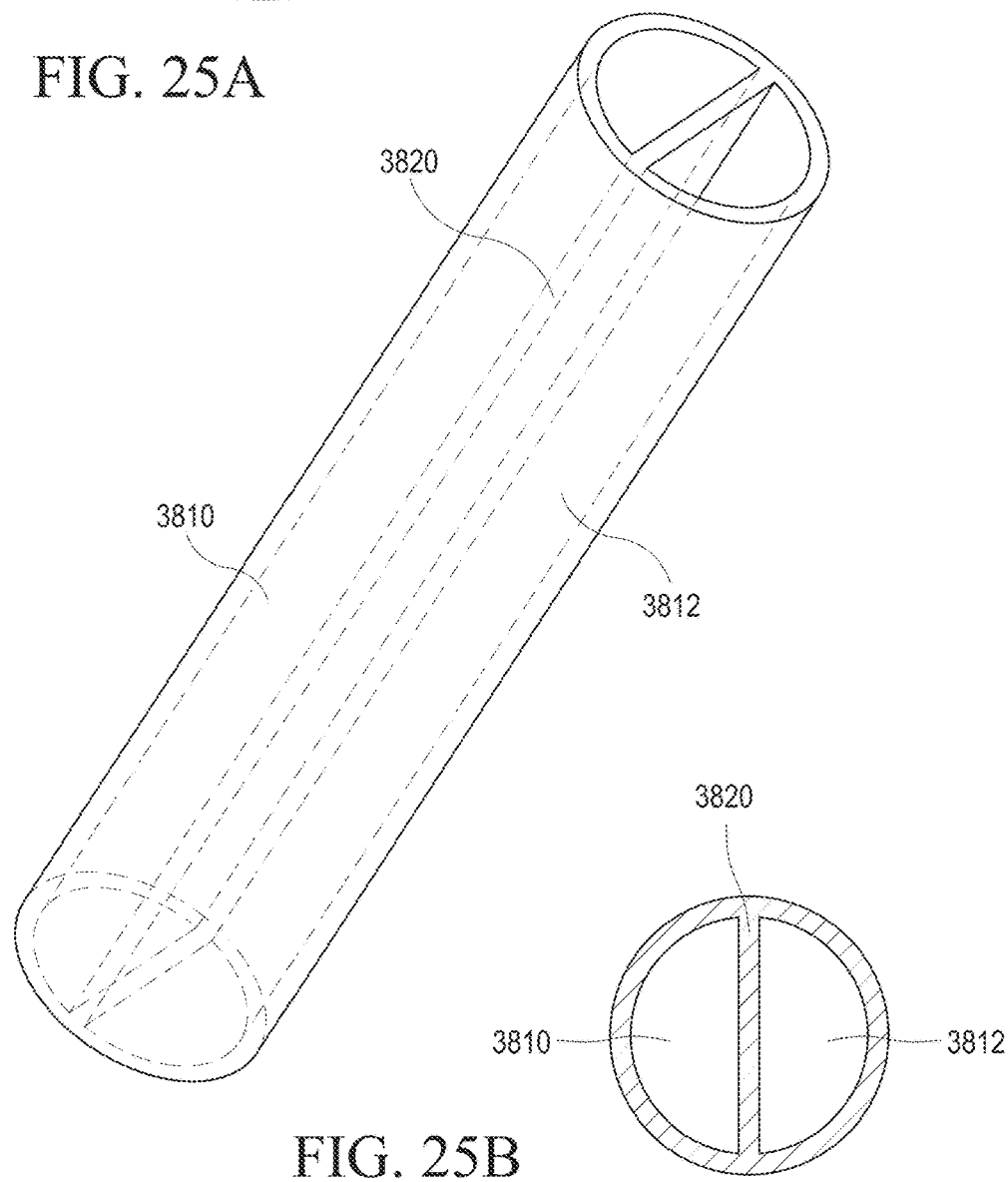
Figure 25C:
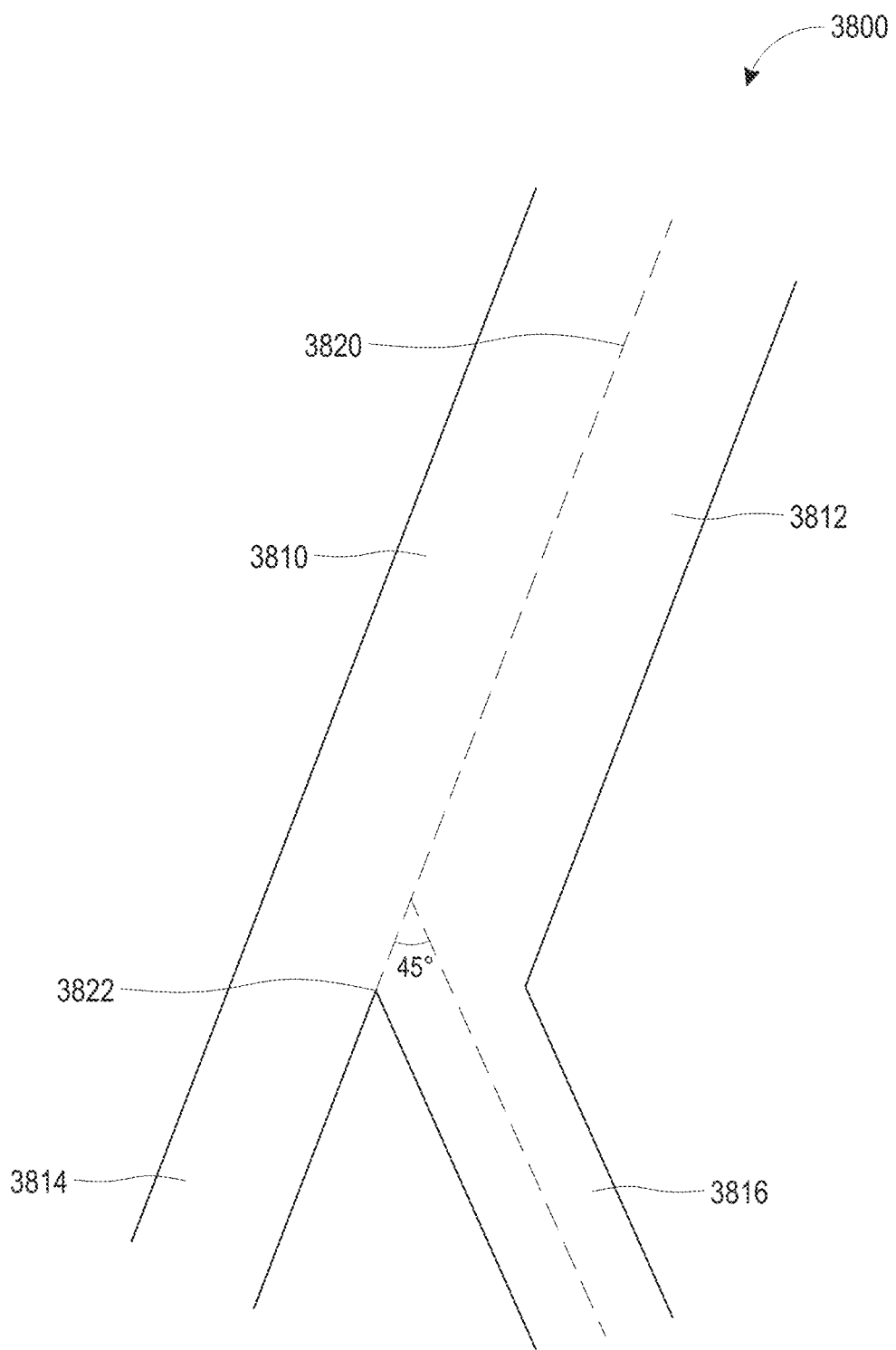

FIGS. 25A-25C depict various views of various embodiments of a dual lumen delivery catheter pusher 3770 and 3800. Any of the features of the pusher 3700 may be implemented with the pusher 3800, and vice versa. FIG. 25A is an end view of an embodiment of the delivery catheter pusher 3770 with a two lumen shaft. A first lumen 3774 is separated from a second lumen 3772 by a wall 3776 extending therebetween. The first lumen 3774 is rounded, for example cylindrical. The second lumen 3772 is crescent or moon shaped. The cross-sectional opening of the second lumen 3772 may extend angularly about a central longitudinal axis of the pusher 3770 for about 30 degrees, about 45 degrees, about 60 degrees, about 90 degrees, from about 30 degrees to about 90 degrees, from about 30 degrees to about 60 degrees, or other amounts or ranges. During implant delivery, an obturator (e.g. a solid plastic tube) is placed within the first lumen 3774 to stiffen the lumen 3774. The tether 3772 that attaches to the implant is in the second lumen 3772.

Following deployment of the implant, the clinician may remove the obturator and insert an intracardiac echo (ICE) catheter through the lumen 3772. This provides the clinician with direct access to the left atrium to visualize the implant 3000. This design is advantageous to allow the clinician to visualize the implant 3000 without the use of transesophageal echocardiography (TEE). TEE requires the use of general anesthesia. Administering general anesthesia increases risks to the patient and complicates the scheduling of the procedure.

Without the two shaft lumen, inserting an ICE catheter to visualize the implant would require a second transseptal puncture to access the left atrium. This is technically challenging and may increase the risk of leaving a residual iatrogenic atrial septal defect due to the extra catheter manipulation required with two sheaths crossing the atrial septum simultaneously. The second puncture also carries the inherent risk of cardiac perforation arising due to the use of sharp needles in the heart.

In various embodiments the shapes of the lumens and wall may vary. For example, FIG. 25B shows an embodiment of a pusher 3800 having semi-circular openings of approximately equal size. Other sizes and shapes of the lumens may be used in the pusher. The first lumen 3810 is divided from the second lumen 3812 by a wall 3820. In some embodiments the two sides could be the same size, or different sizes, the shapes could be a 'D' shape or other shapes. During implant delivery, an obturator (solid plastic tube) is placed within the first lumen 3810 to stiffen it. The tether 3772 that attaches to the implant is in the second lumen 3812.

FIG. 25C depicts the proximal end of an embodiment of a delivery catheter pusher 3800. Similar features may be implemented with the pusher 3700. The pusher 3800 has a bifurcation at the proximal end. At the bifurcation, the obturator containing lumen, or first lumen 3810, goes straight and the tether containing lumen, or second lumen is set at 45 degrees. After the bifurcation point 3822, the first lumen 3810 extends into a bifurcated first lumen 3814, and the second lumen 3812 extends into a bifurcated second lumen 3816. Delivery catheter pusher 3770 may be similarly bifurcated.

E. Hydraulic Loader

Figure 27A:
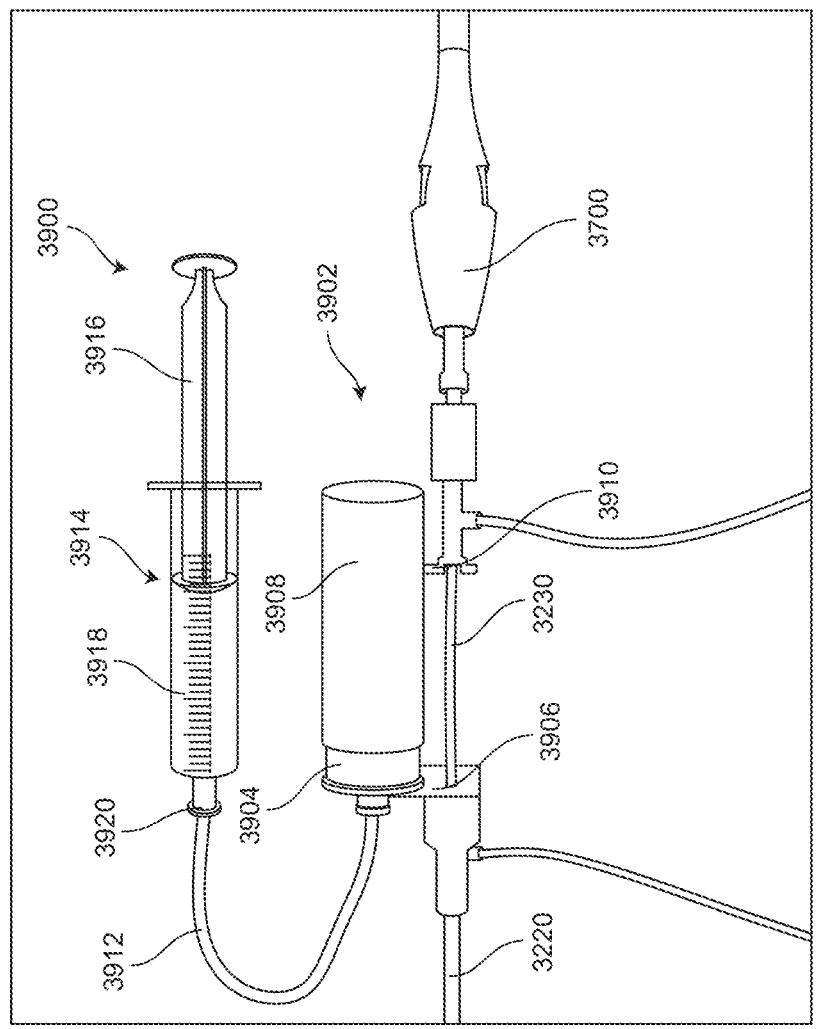
FIGS. 27A-27C are side views of a hydraulic loading system that may be used to load the various occlusion devices into a delivery catheter.
Figure 27B:
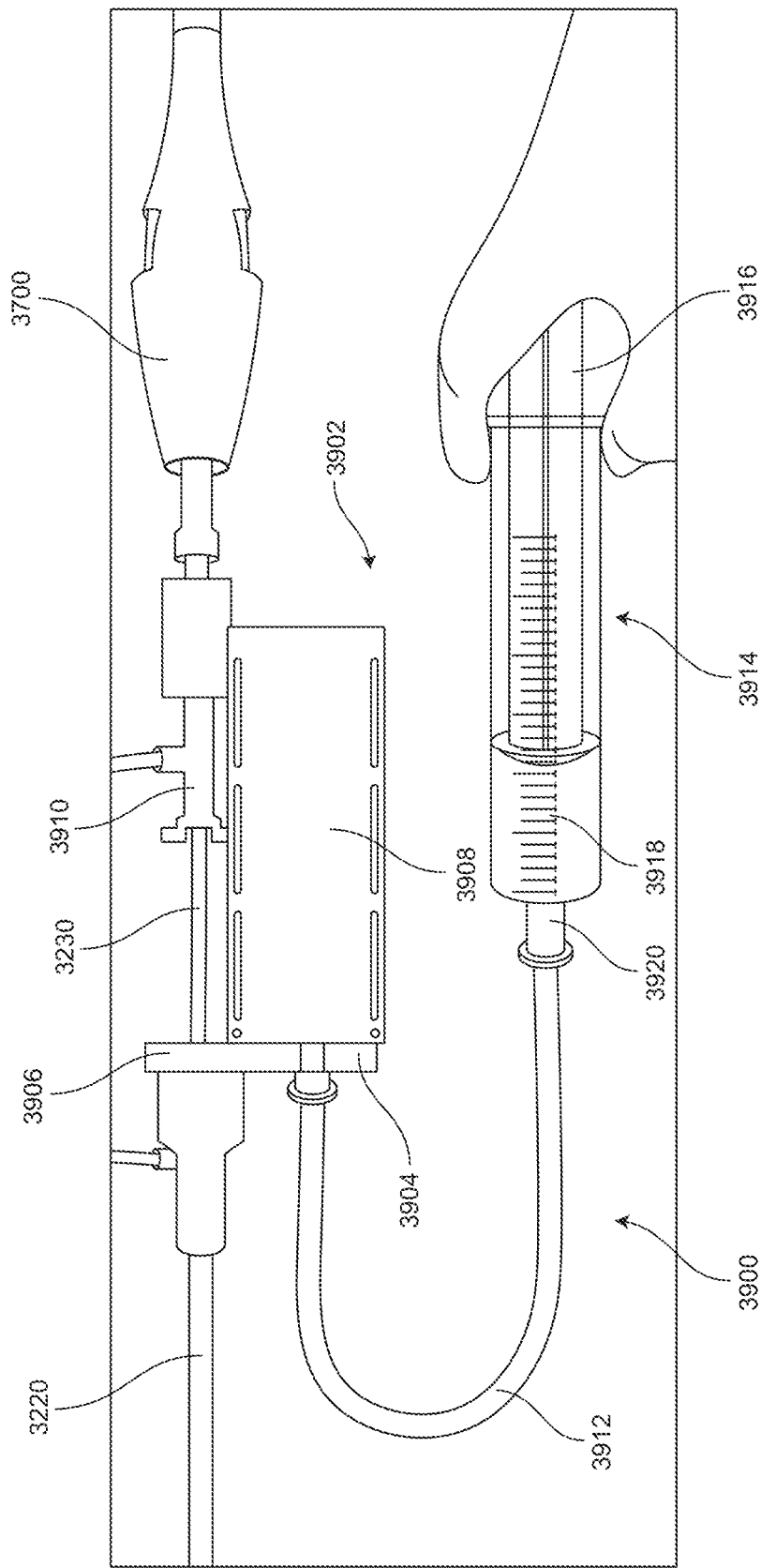
Figure 27C:
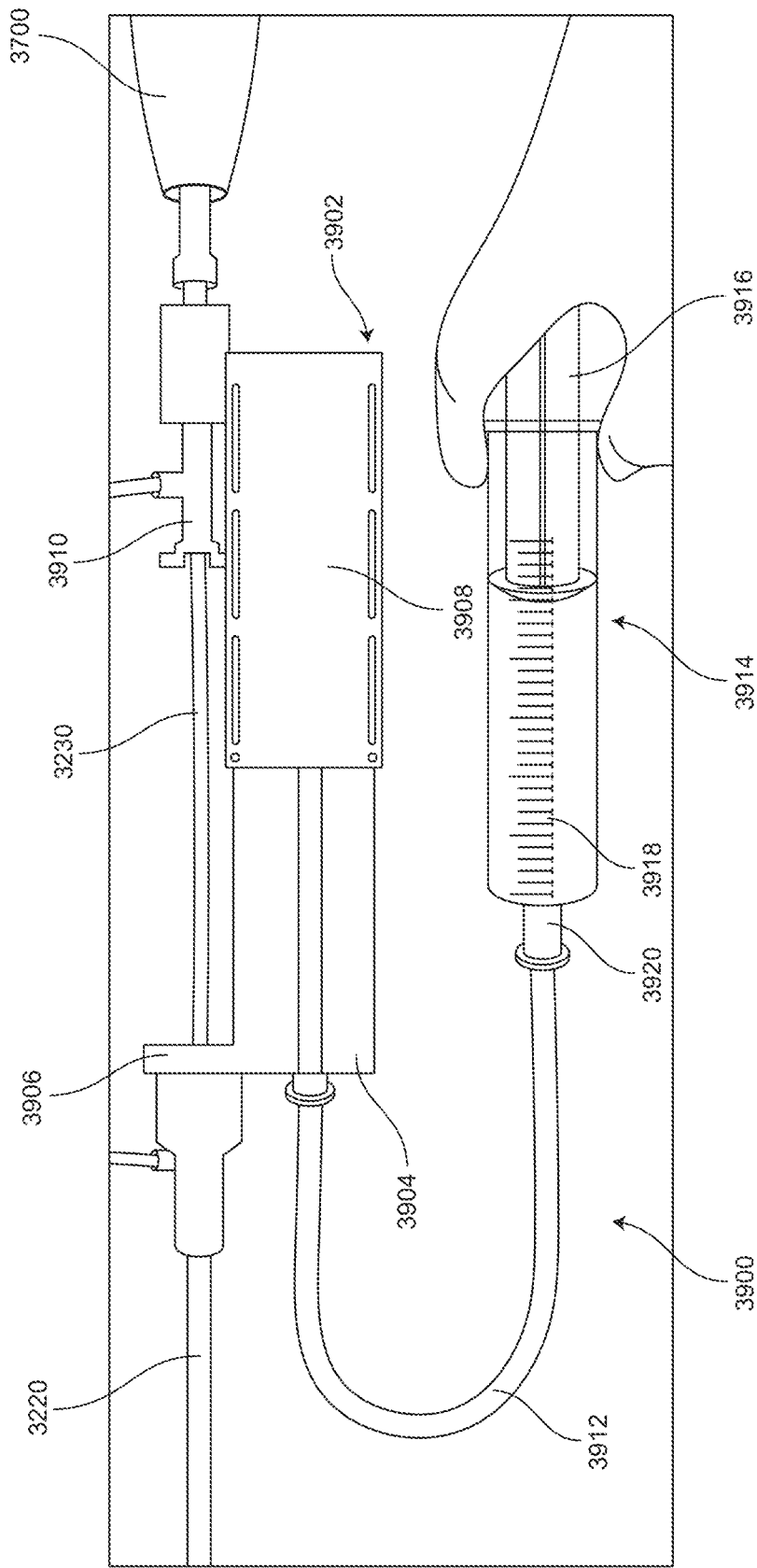

FIG. 26 is a side view of a catheter delivery system that may be used with the various occlusion devices described herein. FIGS. 27A-27C depict various views of various embodiments of a hydraulic loader 3900. FIGS. 27A-27C are side views of the hydraulic loader 3900 coupled to components of the delivery system of FIG. 26. The hydraulic loader 3900 may be used with various LAA implants and associated devices and methods described herein. For example, the hydraulic loader 3900 may be used to load the device 3000 into a delivery catheter. After loading of the device 3000 into the delivery catheter, the delivery catheter may be used with the handle 3700 to deliver and secure the device within the human body.

The hydraulic loader 3900 may couple to components of the delivery system to move portions of the delivery system. The loader 3900 may be mounted about a pusher (such as pusher 3230, pusher 3700, or pusher 3800) between a proximal end of the delivery catheter and a distal end of the handle to retract the occlusion device into the delivery catheter. As shown in FIGS. 27A-27C, a piston actuator 3902 includes a barrel 3904 having a connector 3906 coupled to the delivery catheter 3220. A plunger 3908 of the piston actuator 3902 includes a connector 3910 coupled to the pusher 3230 and abutting the distal end of the handle or components thereof. A hydraulic fluid, such as saline can be introduced into the barrel 3904 of the piston actuator 3902 to apply a force to the plunger 3908 in a proximal direction to cause the plunger 3908 to move proximally relative to the barrel 3904. Proximal movement of the plunger 3908 may cause proximal movement of the pusher 3230, the handle 3700, and/or tether 3240 relative to the delivery catheter 3220 to proximally retract the device into the delivery catheter 3220 when the connector 3906 and the connector 3910 are coupled to the delivery catheter 3220 and the pusher 3230, respectively.

FIG. 27B depicts the plunger 3908 in a first position relative to the barrel 3904, and FIG. 27C depicts the plunger 3908 in a second position relative to the barrel 3904 in which the plunger 3908 is positioned proximally relative to the first position, for example, due to the introduction of a hydraulic fluid into the barrel 3904. Fluid may be introduced into the barrel 3904 via a fluid path tube 3912 of the hydraulic loader 3900.

A syringe 3914 of the hydraulic loader 3900 may be coupled to the tube 3912 to introduce fluid thereto. A plunger 3916 of the syringe 3914 can be advanced into a barrel 3918 of the syringe 3914, for example by a user manipulating the plunger 3916, to advance fluid from the barrel 3918 through a tip 3920 of the syringe 3914 and into the tube 3912. Thus, the syringe 3914 can be operated to advance a hydraulic fluid through the tube 3912 and into the piston actuator 3902 to cause the plunger 3908 of the piston actuator 3902 to move proximally relative to the barrel 3904 of the piston actuator 3902. As described above, when coupled to the delivery system, proximal movement of the plunger 3908 relative to the barrel 3904 can cause retraction of the device into the delivery catheter 3220, for example by causing proximal movement of the pusher 3230 and/or tether 3240.

Use of the hydraulic loader 3900 can also improve control over the positioning of the device within the catheter to allow the device to be loaded at a position close to the distal end of the delivery catheter. For example, an amount of hydraulic fluid may be selected to cause the piston actuator to move a predetermined distance so as to position the device at a position close to the distal end of the delivery catheter. Additionally, or alternatively, a range of motion of the plunger 3908 of the piston actuator 3902 can be selected so that movement of the plunger 3908 to its proximal most position relative to the barrel 3904 causes the device to be retracted to a position close to the distal end of the delivery catheter.

The hydraulic loader 3900 can reduce the force needed to be applied by a user to load the delivery device into the delivery catheter, for example in comparison to application of a pulling force by the user on the pusher and/or tether. In some embodiments, this reduction of force can facilitate loading in delivery catheters of a smaller diameter, such as the smaller diameters described herein. In some embodiments, the cross-sectional areas of the plunger 3908 and the plunger 3916 can be sized so that the force imparted by the piston actuator 3902 is amplified relative to the force applied by a user to the syringe 3914. The force ($F_2$) applied by the piston actuator 3902 is related to the cross-sectional area ($A_2$) of the plunger 3908, the force ($F_1$) applied to the syringe, and the cross-sectional area ($A_1$) of the plunger 3916 as shown in Equation 1:

$$F_2 = F_1 * (A_2/A_1) \qquad \text{Equation 1:}$$

As shown in Equation 1, the force applied by the piston actuator ($F_2$) is larger than the force applied by the user to the syringe ($F_1$) when the cross-sectional area $A_2$ of the plunger 3908 is greater than the cross-sectional area $A_1$ of the plunger 3916. A ratio of the force ($F_2$) applied by the piston actuator to the force ($F_1$) applied by the user to the syringe 3914 is equivalent to a ratio of the cross-sectional area ($A_2$) of the plunger 3908 to the cross-sectional area ($A_1$) of the plunger 3916.

In some embodiments, the piston actuator 3902 is a 12 cubic centimeter (cc) syringe (or has a plunger 3908 equivalent to that of a 12 cc syringe) and the syringe 3914 is a 30 cc syringe. In some embodiments, the syringe 3914 may be a 5 cc or 10 cc or larger syringe. In some embodiments, multiple syringes 3914 can be coupled to the fluid path 3912 to supply hydraulic fluid to the piston actuator 3902 or a single syringe 3914 can be refilled and reconnected to the fluid path 3912 to supply additional hydraulic fluid to the piston actuator 3902.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A conformable left atrial appendage occlusion device, comprising:
    an expandable tubular foam body having a compressible open cell foam sidewall, a proximal, occlusive end for facing a left atrium following implantation of the device in a left atrial appendage, a distal end for facing into the left atrial appendage following implantation of the device in the left atrial appendage, and a longitudinal axis extending therethrough, the tubular foam body having a mean diameter in an unconstrained expansion; and
    a self-expandable support having a proximal end with a plurality of radially-extending recapture struts and a cylindrical tubular body extending distally from radial outer ends of the recapture struts, the support carried within the tubular foam body such that the foam sidewall provides a cushion between the support and a wall of the left atrial appendage following implantation, the cylindrical tubular body comprising a plurality of struts forming a plurality of apexes,
    wherein compression of the device from a diameter of about 35 mm to a diameter of about 20 mm along a minor axis transverse to the longitudinal axis causes no more than about a 5 mm reduction in the mean diameter.

2. The conformable left atrial appendage occlusion device of claim 1, wherein compression of the device from a diameter of about 35 mm to a diameter of about 20 mm along the minor axis transverse to the longitudinal axis causes no more than about a 2 mm reduction in the mean diameter.

3. The conformable left atrial appendage occlusion device of claim 1, wherein the plurality of apexes comprises a plurality of distally facing apexes, and the tubular foam body extends distally beyond the distally facing apexes to provide an atraumatic distal bumper.

4. The conformable left atrial appendage occlusion device of claim 1, further comprising at least one anchor.

5. The conformable left atrial appendage occlusion device of claim 1, wherein the tubular foam body can be compressed within a delivery catheter having an inside diameter of no more than about 20F and can self-expand to a diameter of at least about 35 mm when released from the delivery catheter.

6. The conformable left atrial appendage occlusion device of claim 1, wherein application of 0.10 lbs compressive force along the minor axis transverse to the longitudinal axis produces a compression of at least about 0.25 inches along the minor axis.

7. The conformable left atrial appendage occlusion device of claim 1, wherein application of 0.20 lbs compressive force along the minor axis produces a compression of at least about 0.5 inches along the minor axis.

8. The conformable left atrial appendage occlusion device of claim 1, wherein the foam sidewall has an uncompressed thickness of at least about 0.5 mm.

9. The conformable left atrial appendage occlusion device of claim 1, wherein the foam sidewall extends in a distal direction beyond a distal end of the support by at least about 2 mm in an unconstrained, expanded state.

10. The conformable left atrial appendage occlusion device of claim 1, wherein the foam sidewall comprises a reticulated, cross linked matrix having at least about 90% void content, an average pore size within a range of from about 250-500 microns, a wall thickness of at least about 2 mm, and wherein a pressure required to compress the foam sidewall to 50% strain is at least about 1 psi.

11. The conformable left atrial appendage occlusion device of claim 10, wherein the pressure required to compress the foam sidewall to 50% strain is within a range of from about 1 psi to about 2 psi.

12. The conformable left atrial appendage occlusion device of claim 1, wherein the recapture struts are configured to extend radially linearly in an unconstrained configuration.

13. A conformable left atrial appendage occlusion device, comprising:
    an expandable tubular foam body having a compressible open cell foam sidewall, a proximal, occlusive end for facing a left atrium following implantation of the device in a left atrial appendage, a distal end for facing into the left atrial appendage following implantation of the device in the left atrial appendage, and a longitudinal axis extending therethrough, the tubular foam body having a mean diameter in an unconstrained expansion; and
    a self-expandable support having a proximal end with a plurality of radially-extending recapture struts and a cylindrical tubular body extending distally from radial outer ends of the recapture struts, the support carried within the tubular foam body such that the foam sidewall provides a cushion between the support and a wall of the left atrial appendage following implantation, the cylindrical tubular body comprising a plurality of struts forming a plurality of apexes,
    wherein compression of the device from a diameter of about 35 mm to a diameter of about 25 mm along a minor axis transverse to the longitudinal axis causes an elongation of at least about 6 mm along a major axis transverse to the minor axis.

14. The conformable left atrial appendage occlusion device as in claim 13, wherein compression of the device from a diameter of about 35 mm to a diameter of about 25 mm along the minor axis causes an elongation of at least about 8 mm along the major axis.

15. The conformable left atrial appendage occlusion device of claim 13, further comprising at least one anchor.

16. The conformable left atrial appendage occlusion device of claim 13, wherein the recapture struts are configured to extend radially linearly in an unconstrained configuration.

17. A conformable left atrial appendage occlusion device, comprising:
    an expandable tubular foam body having a compressible open cell foam sidewall, a proximal, occlusive end for facing a left atrium following implantation of the device in a left atrial appendage, a distal end for facing into the left atrial appendage following implantation of the device in the left atrial appendage, and a longitudinal axis extending therethrough, the tubular foam body having a mean diameter in an unconstrained expansion; and
    a self-expandable support having a proximal end with a plurality of radially-extending recapture struts and a cylindrical tubular body extending distally from radial outer ends of the recapture struts, the support carried within the tubular foam body such that the foam sidewall provides a cushion between the support and a wall of the left atrial appendage following implantation, the cylindrical tubular body comprising a plurality of struts forming a plurality of apexes;
    wherein application of 0.10 lbs compressive force along a minor axis transverse to the longitudinal axis produces a compression of at least about 0.2 inches along the minor axis.

18. The conformable left atrial appendage occlusion device as in claim 17, wherein application of 0.20 lbs compressive force along the minor axis produces a compression of at least about 0.5 inches along the minor axis.

19. The conformable left atrial appendage occlusion device as in claim 17, wherein application of no more than about 0.30 lbs compressive force along the minor axis produces a compression of at least about 0.6 inches along the minor axis.

20. The conformable left atrial appendage occlusion device of claim 17, wherein the foam sidewall has an uncompressed thickness of at least about 0.5 mm.

21. The conformable left atrial appendage occlusion device of claim 20, wherein the foam sidewall has an uncompressed thickness of at least about 1.5 mm.

22. The conformable left atrial appendage occlusion device of claim 17, wherein the foam sidewall comprises a reticulated, cross linked matrix having at least about 90% void content, an average pore size within a range of from about 250-500 microns, and a wall thickness of at least about 2 mm, and a pressure required to compress the foam sidewall to 50% strain is at least about 1 psi.

23. The conformable left atrial appendage occlusion device of claim 22, wherein the pressure required to compress the foam sidewall to 50% strain is within a range of from about 1 psi to about 2 psi.

\* \* \* \* \*